US008680974B2

(12) United States Patent
Meiertoberens et al.

(10) Patent No.: US 8,680,974 B2
(45) Date of Patent: Mar. 25, 2014

(54) DEVICE AND METHODS FOR OPTIMIZING COMMUNICATIONS BETWEEN A MEDICAL DEVICE AND A REMOTE ELECTRONIC DEVICE

(75) Inventors: Ulf Meiertoberens, Stocksund (SE); Raymond Strickland, Indianapolis, IN (US); Harvey Buck, Jr., Indianapolis, IN (US); Michael J. Celentano, Fishers, IN (US); Peter Sabol, Columbia City, IN (US); Urs Anliker, Guemligen (CH); Thomas von Bueren, Bern (CH); Jean-Noel Fehr, Neuenburg (CH); Markus Oberli, Kirchberg (CH); Marcel Frikart, Ostermundigen (CH); Markus Jungen, Bolligen (CH)

(73) Assignees: Roche Diagnostics Operations, Inc., Indianapolis, IN (US); Roche Diagnostics International Ltd., Steinhausen (CH)

(*) Notice: Subject to any disclaimer, the term of this patent is extended or adjusted under 35 U.S.C. 154(b) by 1093 days.

(21) Appl. No.: 12/646,752

(22) Filed: Dec. 23, 2009

(65) Prior Publication Data

US 2011/0063094 A1 Mar. 17, 2011

Related U.S. Application Data

(63) Continuation of application No. PCT/US2008/066248, filed on Jun. 9, 2009.

(60) Provisional application No. 61/130,855, filed on Jun. 4, 2008, provisional application No. 60/937,933, filed on Jun. 29, 2007, provisional application No. 60/937,779, filed on Jun. 29, 2007.

(51) Int. Cl.
*G05B 11/01* (2006.01)
*G08B 21/00* (2006.01)
*C12Q 1/68* (2006.01)

(52) U.S. Cl.
USPC ......... 340/12.5; 340/686.4; 340/618; 422/50; 422/63

(58) Field of Classification Search
USPC .................. 340/12.5, 686.4, 618; 422/50, 63
See application file for complete search history.

(56) References Cited

U.S. PATENT DOCUMENTS 4,146,029 A 3/1979 Ellinwood, Jr.
(Continued)

FOREIGN PATENT DOCUMENTS

EP 0079405 A1 5/1983
(Continued)

OTHER PUBLICATIONS

The Bluetooth Forum: "Bluetooth security", Internet citation [online], Feb. 22, 2001. XP002171382. http://www.bluetooth.com/developer/specifiction/specification.asp.
(Continued)

*Primary Examiner* — Steven Lim
*Assistant Examiner* — Omeed Alizada
(74) *Attorney, Agent, or Firm* — Roche Diagnostics Operations, Inc.

(57) ABSTRACT

An electronic device may communicate wirelessly with another electronic device. The electronic device may include a first processor configured to control only wireless communications with the another device but not operations associated only with the electronic device, a second processor configured to control the operations associated only with the electronic device but not the wireless communications with the another device, and a memory device connected between the first and second processors. The first and second processors may each be configured to exchange information with the memory device separately and independently of the exchange of information by the other of the first and second processors with the memory device.

78 Claims, 25 Drawing Sheets

(56) References Cited

U.S. PATENT DOCUMENTS

| | | | |
|---|---|---|---|
| 5,291,609 | A | 3/1994 | Herz |
| 5,364,346 | A | 11/1994 | Schrezenmeir |
| 5,748,103 | A | 5/1998 | Flach et al. |
| 5,997,475 | A | 12/1999 | Bortz |
| 6,289,421 | B1 | 9/2001 | Ali et al. |
| 6,668,196 | B1 | 12/2003 | Villegas et al. |
| 6,909,439 | B1 | 6/2005 | Amro et al. |
| 2001/0044731 | A1 | 11/2001 | Coffman et al. |
| 2004/0024840 | A1 | 2/2004 | Levine et al. |
| 2004/0078416 | A1 | 4/2004 | Kawasaki et al. |
| 2004/0248840 | A1 | 12/2004 | Hansen et al. |
| 2005/0091577 | A1 | 4/2005 | Torres et al. |
| 2005/0162395 | A1 | 7/2005 | Unruh |
| 2006/0047192 | A1 | 3/2006 | Hellwig et al. |
| 2006/0173406 | A1 | 8/2006 | Hayes et al. |
| 2006/0217061 | A1 | 9/2006 | Steele et al. |
| 2007/0109325 | A1 | 5/2007 | Eveleigh |
| 2007/0142767 | A1 | 6/2007 | Frikart et al. |

FOREIGN PATENT DOCUMENTS

| | | | |
|---|---|---|---|
| EP | 0249720 | A2 | 12/1987 |
| EP | 0290683 | A2 | 11/1988 |
| EP | 1759726 | A2 | 3/2007 |
| EP | 1788501 | A1 | 5/2007 |
| EP | 1795116 | A1 | 6/2007 |
| WO | 00/48112 | A2 | 8/2000 |
| WO | 2004/099898 | A2 | 11/2004 |
| WO | 2006/032653 | A2 | 3/2006 |
| WO | 2006/046015 | A1 | 5/2006 |
| WO | 2006/108304 | A1 | 10/2006 |

OTHER PUBLICATIONS

Gehrmann, Christian, "Bluetooth Security White Paper, Bluetooth SIG", Bluetooth Doc, Apr. 19, 2002, pp. 1-46. XP003010085.

Levy, M., et al., "Fifo Memories Supply the Glue for High-Speed Systems", EDN Eleectrical Design News, Reed Business Information, Highlands Ranch, Co, US, vol. 42, No. 6, Mar. 14, 1997, pp. 65, 66, 68 and 70. XP 000695233.

Hastings, C., et al., "Future Trends in Fifo Architectures", Wescon Technical Papers, Western Periodicals Co., North Hollywood, CA, USA, vol. 36, Nov. 17, 1992, pp. 174-178. XP 000350089.

Rasid, M. F. A., et al., "Bluetooth Telemedicine Processor for Multichannel Biomedical Signal Transmission via Mobile Cellular Netowrks", IEEE Transactions on Information Technology in Biomedicine, IEEE Service Center, Los Alamitos, CA, USA, vol. 9, No. 1, Mar. 1, 2005, pp. 35-43. XP 011127538.

International Search Report and Written Opinion mailed Jul. 24, 2008 from PCT/US2008/066247.

International Search Report and Written Opinion mailed Oct. 30, 2008 from PCT/US2008/066288.

International Search Report and Written Opinion mailed Dec. 22, 2008 from PCT/US2008/066267.

International Search Report and Written Opinion mailed Jan. 9, 2009 from PCT/US2008/066248.

International Search Report and Written Opinion mailed Dec. 22, 2008 from PCT/US2008/066299.

International Search Report and Written Opinion mailed Jan. 14, 2009 from PCT/US2008/066331.

International Search Report and Written Opinion mailed Jan. 14, 2009 from PCT/US2008/066262.

DEVICE AND METHODS FOR OPTIMIZING COMMUNICATIONS BETWEEN A MEDICAL DEVICE AND A REMOTE ELECTRONIC DEVICE

REFERENCE

This application is a continuation of PCT/US2008/066248 filed Jun. 9, 2009 which is based on and claims priority to U.S. Provisional Patent Application Ser. No. 60/937,779, filed Jun. 29, 2007, U.S. Provisional Patent Application Ser. No. 60/937,933, filed Jun. 29, 2007, and U.S. Provisional Patent Application Ser. No. 61/130,855, entitled DEVICE AND METHODS FOR OPTIMIZING COMMUNICATIONS BETWEEN AN ELECTRONIC DEVICE AND A MEDICAL DEVICE, filed Jun. 4, 2008. All disclosures identified in this paragraph are hereby incorporated by reference.

FIELD

This disclosure relates generally to electronic devices for wirelessly communicating with one or more other electronic devices, and more specifically to hand held devices configured to communicate with a medical device.

BACKGROUND

Electronic devices for wirelessly communicating with at least one other electronic device are known. It is desirable in at least one of the electronic device and the at least one other electronic device to maintain separate control over telemetry system operations and all other device operations.

SUMMARY

The present invention may comprise one or more of the features recited in the attached claims, and/or one or more of the following features and combinations thereof. An electronic device for communicating wirelessly with another electronic device may comprise a first processor configured to control only wireless communications with the another device but not operations associated only with the electronic device, a second processor configured to control the operations associated only with the electronic device but not the wireless communications with the another device and a memory device connected between the first and second processors. Each of the first and second processors is configured to exchange information with the memory device separately and independently of the exchange of information by the other of the first and second processors with the memory device.

A first one of a synchronous and an asynchronous interface may be electrically connected between the first processor and the memory device. The first processor may be configured to send information wirelessly received from another electronic device to the memory device via the first one of the synchronous and asynchronous interface, and to retrieve information to be communicated wirelessly to the another electronic device from the memory device via the first one of the synchronous and the asynchronous interface.

A second one of a synchronous and an asynchronous interface may be electrically connected between the second processor and the memory device. The second processor may be configured to retrieve from the memory device via the second one of the synchronous and asynchronous interface the information wirelessly received from the another electric device and sent to the memory device by the first processor, and to send to the memory device via the second one of the synchronous and asynchronous interface the information to be communicated wirelessly to the another electronic device by the first processor.

The memory device may comprise an outbound buffer that is configured to store therein the information sent to the memory device by the second processor and that is to be communicated wirelessly to the another electronic device by the first processor. The outbound buffer may be in data communication with the first and second ones of the synchronous and asynchronous interfaces.

The memory device may comprise an inbound buffer that is configured to store therein the information wirelessly received from the another electric device and sent to the memory device by the first processor and that is to be retrieved from the memory device by the second processor. The inbound buffer may be in data communication with the first and second ones of the synchronous and asynchronous interfaces. The first processor may be configured to incorporate the information retrieved from the outbound buffer into a wireless communications protocol structure, and to then wirelessly transmit the incorporated information to the another electronic device using the wireless communication protocol. The wireless communication protocol may be a radio frequency communication protocol. Alternatively or additionally, the first processor may be configured to wirelessly receive information incorporated into a wireless communication protocol structure from the another electronic device, to isolate the information from the wireless communication protocol structure and to then send the isolated information to the inbound buffer of the memory device. The wireless communication protocol may again be a radio frequency communication protocol. The second processor may be configured to send the information to the memory device by requesting, asynchronously with respect to operation of the first processor, the state of the outbound buffer of the memory device and to send the information to the memory device only if the memory device indicates that the outbound buffer is not full, and to otherwise wait for a time period before again requesting, asynchronously with respect to operation of the first processor, the state of the outbound data buffer of the memory device. Alternatively or additionally, the second processor may be configured to retrieve from the memory device the information wirelessly received from the another electric device and sent to the memory device by the first processor by periodically, and asynchronously with respect to operation of the first processor, requesting the state of the inbound buffer of the memory device, the second processor configured to retrieve the information from the inbound buffer of the memory device only if the memory device indicates that the inbound buffer contains information, and to otherwise continue to periodically, and asynchronously with respect to operation of the second processor, request the state of the inbound data buffer.

The first one of the synchronous and asynchronous interface may be an asynchronous interface that may include a clear to send (CTS) signal line. The first processor may be configured to activate the CTS signal line whenever the first processor is requesting data and otherwise deactivate the CTS signal line. The first processor may be configured to request the information to be communicated wirelessly to the another electronic device from the memory device by periodically, and asynchronously with respect to operation of the second processor and operation of the memory device, activating the CTS signal line and retrieving the information to be wirelessly communicated to the another electronic device from the outbound buffer only if the outbound buffer contains data, and to otherwise continue to periodically, and asynchronously with respect to operation of the second, processor and operation of the memory device, activate the CTS signal line. The asynchronous interface may also include a request to send (RTS) signal line. The memory device may be configured to activate the RTS signal line whenever the inbound buffer is not full and otherwise deactivate the RTS signal line. The first processor may be configured to send the information wirelessly received from the another electric device to the memory device by periodically, and asynchronously with respect to operation of the second processor and operation of the memory device, monitoring the RTS signal line and sending the information wirelessly received from the another electronic device to the inbound buffer of the memory device only if the RTS signal line is activated, and to otherwise continue to periodically, and asynchronously with respect to operation of the second processor and operation of the memory device, monitor the RTS signal line.

The electronic device may further comprise one or more batteries, a first power supply configured to produce a first supply voltage derived from the one or more batteries and to provide the first supply voltage to the first second processor and to the memory unit, and a second power supply configured to produce a second supply voltage derived from the one or more batteries and to provide the second supply voltage to the first processor. The memory device may comprise a third processor.

The electronic device may further comprise an on/off switch. The memory device may be configured to be responsive to an on signal produced by the on/off switch to en able the second power supply to produce the second supply voltage, and to an off signal produced by the on/off switch to command orderly shutdown of the first processor and to then disable the second power supply such that the second power supply no longer produces the second supply voltage.

Alternatively or additionally, the electronic device may further comprise a test element receiving port configured to receive a test element, electronic circuitry configured to detect insertion of the test element into the test element receiving port and to produce a corresponding strip insert signal, and a fourth processor configured to analyze a liquid sample provided on the test element to determine a concentration of an analyte in the liquid sample. The fourth processor may be configured to be responsive to the strip insert signal to provide a strip insertion message to the second processor, monitored by the memory device. The memory device may be configured to be responsive to the strip insertion message to command orderly shutdown of the first processor and to then disable the second power supply such that the second power supply no longer produces the second supply voltage. The fourth processor may be configured to provide a test complete message to the second processor, monitored by the memory device, when the concentration of the analyte is determined by the fourth processor. The memory device may be configured to be responsive to the test complete message to enable the second power supply such that the second power supply produces the second supply voltage.

Alternatively or additionally, the electronic device may further comprise a plurality of user activated buttons or keys. If the first power supply is producing the first supply voltage and the second power supply is producing the second supply voltage, the memory device may be responsive to one of a simultaneous activation of a predefined combination of two or more of the plurality of user activated buttons or keys, activation of a predefined sequence of two or more of the plurality of user activated buttons or keys and a dedicated one of the plurality of user activated buttons or keys to command orderly shutdown of the first processor and to then disable the second power supply such that the second power supply no longer produces the second supply voltage.

Alternatively or additionally, the electronic device may further comprise a plurality of user activated buttons or keys. If the first power supply is producing the first supply voltage and the second power supply is disabled so that it is not producing the second supply voltage, the memory device may be responsive to simultaneous activation of a predefined combination of two or more of the plurality of user activated buttons or keys to enable the second supply voltage so that it produces the second supply voltage.

Alternatively or additionally, the electronic device may further comprise an on/off switch. The first power supply may be enabled by an on signal produced by the on/off switch to produce the first supply voltage, and may be disabled by an off signal produced by the on/off switch such that the first power supply does not produce the first supply voltage. The electronic device may further comprise a display unit. The second processor may be configured, when the first power supply is enabled, to control the display unit to display an indication that a wireless connection between the electronic device and another electronic device is not established.

Alternatively or additionally, the electronic device may further comprise a voltage sense line electrically connected between the second power supply and the second processor. The voltage sense line may carry a sense voltage that is indicative of the supply voltage produced by the second power supply. The second processor may be configured to be responsive to the sense voltage to store, asynchronously with respect to operation of the first processor, an acknowledgement response command in the memory device when the sense voltage indicates that the second power supply has been enabled to produce the second supply voltage after having been disabled such that the second power supply did not produce the second supply voltage. The first processor may be configured to retrieve, asynchronously with respect to operation of the second processor, the acknowledgment response command from the memory device, and to wirelessly transmit the acknowledgement transmit command. The first processor may be configured, if the another electronic device wirelessly transmits an acknowledgement response in response to receipt of the acknowledgement response command and the transmitted acknowledgement response is received by the first processor, to isolate the acknowledgement response from a wireless communication protocol structure used by the another electronic device to wirelessly transmit the acknowledgment response, and to then store the acknowledgement response in the memory unit asynchronously with respect to operation of the memory unit and operation of the second processor. The electronic device may further comprise a display unit. The second processor may be configured to, asynchronously with respect to operation of the first processor, retrieve the acknowledgement response from the memory unit and to then control the display unit to display an indication that a wireless connection exists between the electronic device and the another electronic device. The second processor may be configured to periodically store the acknowledgement response command in the memory device asynchronously with respect to operation of the first processor, to then periodically check the memory device, asynchronously with respect to operation of the first processor, and to continue to control the display unit to display the indication that the wireless connection exists between the electronic device and the another electronic device as long as the second processor retrieves the acknowledgement response from the memory unit within a predefined time period following storage of the acknowledgement response command in the memory device. The second processor may be configured to control the display unit to display the indication that the wireless connection does not exist between the electronic device and the another electronic device if second processor does not retrieves the acknowledgement response from the memory unit within the predefined time period following storage of the acknowledgement response command in the memo device.

Alternatively or additionally, the electronic device may further comprise a display unit, and a voltage sense line electrically connected between the second power supply and the second processor. The voltage sense line may carry a sense voltage that is indicative of the supply voltage produced by the second power supply. The second processor may be configured to be responsive to the sense voltage to control the display unit to display an indication that the second processor is producing the second supply voltage if the sense voltage indicates that the second processor is producing the second supply voltage.

Alternatively or additionally, the electronic device may further comprise a display unit, and a voltage sense line electrically connected between the second power supply and the second processor. The voltage sense line may carry a sense voltage that is indicative of the supply voltage produced by the second power supply. The second processor may be configured to be responsive to the sense voltage to control the display unit to display an indication that the second processor is not producing the second supply voltage if the sense voltage indicates that the second processor is not producing the second supply voltage.

Alternatively or additionally, the electronic device may further comprise an on/off switch, a display unit, and a fourth processor configured to analyze a liquid sample provided on a test element to determine a concentration of an analyte in the liquid sample. The fourth processor may be configured to provide a test complete message to the second processor when the concentration of the analyte is determined by the fourth processor. The second power supply may be disabled such that it does not produce the second supply voltage when the fourth processor is determining the concentration of the analyte in the liquid sample. The second power supply may be configured to be responsive to an on signal produced by the on/off switch to become enabled and produce the second supply voltage. The second processor may be configured to be responsive to the test complete message produced by the fourth processor to control the display unit to display a message that instructs the user to active the on/off switch to produce the on signal in order to communication wirelessly with the another electronic device.

Alternatively or additionally, the memory device comprises an outbound buffer that is configured to store therein information sent to the memory device by the second processor that is to be communicated wirelessly to another electronic device by the first processor. The outbound buffer may be in data communication with the first and second processors. The memory device may be configured to monitor a status of the outbound buffer and to control operation of the second power supply based on the status of the outbound buffer. The memory device may comprise a timer circuit. The memory device may be configured to reset the timer circuit each time the second processor stores information in the outbound buffer of the memory device. The memory device may be configured to maintain the second power supply enabled such that the second power supply produces the second supply voltage as long as the memory device resets the timer circuit when a predefined time period elapses since last resetting the timer circuit. The memory device may be configured to disable the second power supply such that the second power supply does not produce the second supply voltage if the memory device does not reset the timer circuit before the predefined time period elapses since last resetting the timer circuit. The memory device may be configured to reset the timer circuit when second processor stores information in the outbound buffer of the memory device while the second power supply is disabled. The memory device may be configured to enable the second power supply such that the second power supply produces the second supply voltage when the timer circuit is reset while the second power supply is disabled. The electronic device may further comprise a test element receiving port configured to receive a test element, electronic circuitry configured to detect insertion of the test element into the test element receiving port and to produce a corresponding strip insert signal, and a fourth processor configured to analyze a liquid sample provided on the test element to determine a concentration of an analyte in the liquid sample. The fourth processor may be configured to be responsive to the strip insert signal to provide a strip insertion message to the second processor. The second processor may be configured to cease storing information in the outbound buffer of the memory device when the fourth processor produces the strip insert message so that the memory device does not reset the timer circuit before the predefined time period elapses since last resetting the timer circuit and the memory device then disables the second power supply such that the second power supply does not produce the second supply voltage. The fourth processor may be configured to provide a test complete message to the second processor when the concentration of the analyte is determined by the fourth processor. The second processor may be configured to resume storing information in the outbound buffer of the memory device when the fourth processor produces the test complete message so that the memory device resets the timer circuit and the memory device then enables the second power supply such that the second power supply produces the second supply voltage. The electronic device may further comprise a test element receiving port configured to receive a test element, and a fourth processor configured to analyze a liquid sample provided on the test element to determine a concentration of an analyte in the liquid sample. The fourth processor may be configured to be responsive to a request to disable the second power supply to provide a corresponding message to the second processor. The second processor may be configured to cease storing information in the outbound buffer of the memory device when the fourth processor produces the corresponding message so that the memory device does not reset the timer circuit before the predefined time period elapses since last resetting the timer circuit and the memory device then disables the second power supply such that the second power supply does not produce the second supply voltage.

Alternatively or additionally, the second power supply may be always enabled such that the second power supply always produces the second supply voltage. The first processor may be configured to be responsive to a number of different events to transition into, and out of, a number of different low power states. The first processor may further comprise a timer circuit. The first processor may be configured to remain in a fully powered awake state as long as a first predefined time period does not elapse since last resetting the timer circuit. The memory device may comprise an outbound buffet that is configured to store therein information sent to the memory device by the second processor that is to be communicated wirelessly to another electronic device by the first processor. The outbound buffer may be in data communication with the first and second processors. The first processor may be configured to periodically check a status of the outbound buffer and to reset the timer circuit only if the outbound buffer contains information to be wirelessly communicated to the another electronic device. The first processor may be configured to transition to a first low power state if the first predefined time period elapses since last resetting the tinier circuit, wherein the first processor consumes less electrical power in the first low power state than when in the fully powered awake state. The first processor may be configured to transition to a second low power state, in which the first processor consumes less electrical power than when in the first low power state, if a second predefined time period elapses since last resetting the timer circuit, the second predefined time period being greater than the first predefined time period. The first processor may be configured to transition to successively lower power states, in which the first processor consumes successively less power than in the previous low power state, as the time period that elapses since resetting the timer circuit successively increases beyond the first predefined time period. The first processor may be configured in a lowest power state only to periodically wake up to check the status of the outbound buffer of the memory device, and to wake up to the fully powered awake state if the outbound buffer of the memory device has information stored therein. The first processor may be otherwise configured to transition back to the lowest power state. The electronic device may further comprise an on/off switch. The first processor may be configured to transition from any of the number of different low power states to a fully powered awake state when the on/off switch is switched to an on position. The first processor may be configured to transition from the fully powered awake state and any of the number of different low power states to a lowest power sleep state when the on/off switch is switched to an off position. The memory device may have a sleep state and an awake state. The memory device may be configured to transition from the sleep state of the memory device to the awake state of the memory device when the on/off switch is switched to the on position. The electronic device may further comprise a test element receiving port configured to receive a test element, electronic circuitry configured to detect insertion of the test element into the test element receiving port and to produce a corresponding strip insert signal, and a fourth processor configured to analyze a liquid sample provided on the test element to determine a concentration of an analyte in the liquid sample. The fourth processor may be configured to be responsive to the strip insert signal to provide a corresponding strip insert message to the second processor. The second processor may be configured to cease storing information in the outbound buffer of the memory device when the fourth processor produces the strip insert message so that the first processor then successively transitions to lower power states as successively longer time periods elapse since last resetting the timer circuit. The fourth processor may be configured to provide a test complete message when the fourth processor has determined the concentration of an analyte in the liquid sample. The second processor may be configured to resume storing information in the outbound buffer of the memory device when the fourth processor produces the test complete message so that the first processor then transitions to the fully powered awake state to service the information stored in the outbound buffer of the memory device. The electronic device may further comprise a plurality of user activated buttons or keys. The first processor may be configured to transition from any of the number of different low power states to a fully powered awake state upon detection of one of a simultaneous activation of a predefined combination of two or more of the plurality of user activated buttons or keys, activation of a predefined sequence of two or more of the plurality of user activated buttons or keys and a dedicated one of the plurality of user activated buttons or keys. Alternatively or additionally, the first processor may be configured to transition from the fully powered awake state and any of the number of different low power states to an un-powered off state upon detection of one of a simultaneous activation of a predefined combination of two or more of the plurality of user activated buttons or keys, activation of a predefined sequence of two or more of the plurality of user activated buttons or keys and a dedicated one of the plurality of user activated buttons or keys.

Alternatively or additionally, the electronic device may further comprise a clock circuit having a programming input that is electrically connected to the second processor and an output that is electrically connected to the memory device. The clock circuit may be programmable via the second processor with at least one automatic on time or reminder, and the clock circuit is configured to produce a trigger signal upon occurrence of the at least one automatic on time or reminder. The memory device may be responsive to the trigger signal, when the second power supply is disabled, to enable the second power supply such that the second power supply produces the second supply voltage.

Alternatively or additionally, the electronic device may further comprise a test element receiving port configured to receive a test element, and a fourth processor that is electrically connected to the second processor and that is configured to analyze a liquid sample provided on the test element to determine a concentration of an analyte in the liquid sample. The fourth processor may be configured to provide a value of the concentration of the analyte in the liquid sample to the second processor. An electronic switch may be configured to produce a first signal upon detection of insertion of the test element into the test element receiving port and to produce a second signal upon detection of removal of the test element from the test element receiving port. The electronic switch may have an output that is electrically connected to the fourth processor and to the memory device such that the first and second signals produced by the switch are provided to the fourth processor and to the memory device. The memory device may be configured to be responsive to the first signal produced by the electronic switch to command orderly shutdown of the first processor and to then disable the second power supply such that the second power supply does not produce the second supply voltage. The memory device may be configured to be responsive to the second signal produced by the electronic switch, if the second power supply is disabled, to enable the second power supply such that the second power supply produces the second supply voltage.

Alternatively or additionally, the electronic device may further comprise a test element receiving port configured to receive a test element, and a switch configured to produce a first signal upon detection of insertion of the test element into the test element receiving port and to produce a second signal upon detection of removal of the test element from the test element receiving port. The switch may have an output that is electrically connected only to the memory device such that the first and second signals produced by the switch are provided to the memory device. The memory device may be configured to be responsive to the first signal produced by the switch to command orderly shutdown of the first processor and to then disable the second power supply such that the second power supply does not produce the second supply voltage. The memory device may be configured to be responsive to the second signal produced by the switch, if the second power supply is disabled, to enable the second power supply such that the second power supply produces the second supply voltage.

Alternatively or additionally, the electronic device may further comprise a current sensing circuit having at least one input that is electrically connected to the first power supply and an output that is electrically connected to the second power supply. The current sensing circuit may be configured to produce a control signal having a first state and a second state based on a magnitude of a supply current produced by the first power supply. The first state of the control signal produced by the current sensing circuit may disable the second power supply such that the second power supply does not produce the second supply voltage and the second state of the control signal produced by the current sensing circuit may enable the second power supply such that the second power supply produces the second supply voltage. The current sensing circuit may be configured to produce the second state of the control signal when the second processor is fully activated for operation such that the magnitude of the supply current produced by the first power supply is greater than when the second processor is not fully activated for operation. The second processor may include a timer circuit that the second processor resets periodically when the second processor is actively operating. The second processor may be configured to transition to a low power sleep state if the second processor is inactive for a predefined time period following a last reset of the timer circuit. The current sensing circuit may be configured to produce the first state of the control signal when the second processor transitions to the low power sleep state such that the magnitude of the supply current produced by the first power supply is greater than when the second processor is actively operating. The electronic device may further comprise a test element receiving port configured to receive a test element, electronic circuitry, and a fourth processor electrically connected to the electronic circuitry and to the second processor. The first power supply may provide the first supply voltage to the electronic circuitry and to the fourth processor. The electronic circuitry and the fourth processor may each be normally in a low power sleep state such that the magnitude of the supply current produced by the first power supply is less than when the electronic circuitry and the fourth processor are both actively operating. The current sensing circuit may normally produce the second state of the control signal, such that the second power supply is normally enabled and producing the second supply voltage, when the electronic circuitry and the fourth processor are each in the low power sleep states. The electronic circuitry may be configured to be responsive to insertion of the test element into the test element receiving port to transition from the low power sleep state thereof to an actively operating state and produce a corresponding strip insert signal. The fourth processor may be configured to be responsive to the strip insert signal to transition from the low power operating state thereof to an actively operating state and analyze a liquid sample provided on the test element to determine a concentration of an analyte in the liquid sample. The magnitude of the supply current produced by the first power supply when the electronic circuitry and the fourth processor are both actively operating may be greater than when the electronic circuitry and the fourth processor are in their low power sleep states. The current sensing circuit may be configured to transition the control signal from the first state thereof to the second state thereof when the electronic circuitry and the fourth processor each transition from the low power sleep state to the actively operating state. The electronic circuitry and the fourth processor may each be configured to transition from the actively operating state to the low power sleep state after the fourth processor determines the concentration of the analyte in the liquid sample. The current sensing circuit may be configured to transition the control signal from the second state thereof to the first state thereof when the electronic circuitry and the fourth processor each transition from the actively operating state to the low power sleep state after the fourth processor determines the concentration of the analyte in the liquid sample. The electronic circuitry may comprise a timer circuit that is programmed with at least one automatic on time or reminder. The clock circuit may be configured to produce a trigger signal upon occurrence of the at least one automatic on time or reminder. The electronic circuitry may be configured to be responsive to the trigger signal to transition from the low power operating state thereof to an actively operating state and to pass the trigger signal to the fourth processor. The fourth processor may be configured to be responsive to the trigger signal to transition from the low power operating state thereof to an actively operating state and to pass the trigger signal to the second processor. The magnitude of the supply current produced by the first power supply when the electronic circuitry and the fourth processor are both actively operating may be greater than when the electronic circuitry and the fourth processor are in their low power sleep states. The current sensing circuit may be configured to transition the control signal from the first state thereof to the second state thereof when the electronic circuitry and the fourth processor each transition from the low power sleep state to the actively operating state.

Alternatively or additionally, the electronic device may further comprise a current sensing circuit having at least one input that is electrically connected to the first power supply and an output that is electrically connected to the memory device. The current sensing circuit may be configured to produce a control signal having a first state and a second state based on a magnitude of a supply current produced by the first power supply. The memory device may be responsive to the first state of the control signal produced by the current sensing circuit to disable the second power supply such that the second power supply does not produce the second supply voltage, and to the second state of the control signal produced by the current sensing circuit to enable the second power supply such that the second power supply produces the second supply voltage. The current sensing circuit may be configured to produce the second state of the control signal when the second processor is fully activated for operation such that the magnitude of the supply current produced by the first power supply is greater than when the second processor is not fully activated for operation. The second processor may include a timer circuit that the second processor resets periodically when the second processor is actively operating. The second processor may be configured to transition to a low power sleep state if the second processor is inactive for a predefined time period following a last reset of the timer circuit. The current sensing circuit may be configured to produce the first state of the control signal when the second processor transitions to the low power sleep state such that the magnitude of the supply current produced by the first power supply is greater than when the second processor is actively operating. The electronic device may further comprise a test element receiving port configured to receive a test element, electronic circuitry, and a fourth processor electrically connected to the electronic circuitry and to the second processor. The first power supply may provide the first supply voltage to the electronic circuitry and to the fourth processor. The electronic circuitry and the fourth processor may each be normally in a low power sleep state such that the magnitude of the supply current produced by the first power supply is less than when the electronic circuitry and the fourth processor are both actively operating. The current sensing circuit may normally produce the second state of the control signal, such that the second power supply is normally enabled and producing the second supply voltage, when the electronic circuitry and the fourth processor are each in the low power sleep states. The electronic circuitry may be configured to be responsive to insertion of the test element into the test element receiving port to transition from the low power sleep state thereof to an actively operating state and produce a corresponding strip insert signal. The fourth processor may be configured to be responsive to the strip insert signal to transition from the low power operating state thereof to an actively operating state and analyze a liquid sample provided on the test element to determine a concentration of an analyte in the liquid sample. The magnitude of the supply current produced by the first power supply when the electronic circuitry and the fourth processor are both actively operating may be greater than when the electronic circuitry and the fourth processor are in their low power sleep states. The current sensing circuit may be configured to transition the control signal from the first state thereof to the second state thereof when the electronic circuitry and the fourth processor each transition from the low power sleep state to the actively operating state. The electronic circuitry and the fourth processor may each be configured to transition from the actively operating state to the low power sleep state after the fourth processor determines the concentration of the analyte in the liquid sample. The current sensing circuit may be configured to transition the control signal from the second state thereof to the first state thereof when the electronic circuitry and the fourth processor each transition from the actively operating state to the low power sleep state after the fourth processor determines the concentration of the analyte in the liquid sample. The electronic circuitry may comprise a timer circuit that is programmed with at least one automatic on time or reminder. The clock circuit may be configured to produce a trigger signal upon occurrence of the at least one automatic on time or reminder. The electronic circuitry may be configured to be responsive to the trigger signal to transition from the low power operating state thereof to an actively operating state and to pass the trigger signal to the fourth processor. The fourth processor may be configured to be responsive to the trigger signal to transition from the low power operating state thereof to an actively operating state and to pass the trigger signal to the second processor. The magnitude of the supply current produced by the first power supply when the electronic circuitry and the fourth processor are both actively operating may be greater than when the electronic circuitry and the fourth processor are in their low power sleep states. The current sensing circuit may be configured to transition the control signal from the first state thereof to the second state thereof when the electronic circuitry and the fourth processor each transition from the low power sleep state to the actively operating state.

If a wireless connection between the electronic device and the another electronic device is terminated or lost and the second processor sends information to the outbound buffer, one of the first processor and the second processor may be configured to clear the outbound buffer after a predefined number of failed attempts by the first processor to reestablish a wireless connection between the electronic device and the another electronic device. The first processor may be configured to transition to successively lower power states, in which the first processor consumes successively less power than in the previous low power state, as the time period that elapses since resetting the timer circuit successively increases beyond the first predefined time period following the predefined number of failed attempts by the first processor to reestablish a wireless connection between the electronic device and the another electronic device. The first processor may be configured in a lowest power state only to periodically wake up to check the status of the outbound buffer of the memory device, and to wake up to the fully powered awake state if the outbound buffer of the memory device has information stored therein. The first processor may be otherwise configured to transition back to the lowest power state. The first processor may be configured in the lowest power state to produce a power supply control signal if the time period that elapses since resetting the timer circuit reaches a predefined time out value that is greater than the time period for which the first processor enters the lowest power sleep state. The second power supply may be configured to become disabled such that the second power supply does not produce the second supply voltage when the first processor produces the power supply control signal. The electronic device may further comprise a plurality of user activated buttons or keys. The second power supply may be configured to be responsive to one of a simultaneous activation of a predefined combination of two or more of the plurality of user activated buttons or keys, activation of a predefined sequence of two or more of the plurality of user activated buttons or keys and a dedicated one of the plurality of user activated buttons or keys to become enabled such that the second power supply produces the second supply voltage. The first processor may be configured to enter the lowest power sleep state when the second power supply is via the one of the predefined combination of two or more of the plurality of user activated buttons or keys, activation of a predefined sequence of two or more of the plurality of user activated buttons or keys and a dedicated one of the plurality of user activated buttons or keys.

An electronic device for communicating wirelessly with another electronic device may comprise a first processor that controls only wireless communications with the another device and excluding operations associated only with the electronic device, a second processor that controls the operations associated only with the electronic device and excluding the wireless communications with the another device, and a memory device connected between the first and second processors. The first and second processors may each operate autonomously with respect to each other and each exchange information with the memory device independently of each other.

An electronic device for communicating wirelessly with another electronic device may comprise a first processor that controls only wireless communications with the another device and excluding operations associated only with the electronic device, a second processor that controls the operations associated only with the electronic device and excluding the wireless communications with the another device, and a memory device connected between the first and second processors. The first and second processors may each operate independently of each other and may each operate asynchronously with respect to each other when exchanging information with the memory device.

An electronic device for communicating wirelessly with another electronic device may comprise a first processor configured to control only wireless communications with the another device but not operations associated only with the electronic device, a second processor configured to control the operations associated only with the electronic device but not the wireless communications with the another device, a memory device electrically connected to the first and second processors, and a clock circuit that is separate and independent from the first and second processors and that produces at least one timing signal used independently by the first processor and the second processor to control exchange of the information between the first and second processors and the memory device.

DETAILED DESCRIPTION

For the purposes of promoting an understanding of the principles of the invention, reference will now be made to a number of illustrative embodiments shown in the attached drawings and specific language will be used to describe the same.

The following co-pending patent applications are incorporated herein by reference: PCT Patent Application No. PCT/US2008/066288, entitled APPARATUS AND METHOD FOR REMOTELY CONTROLLING AN AMBULATORY MEDICAL DEVICE; PCT Patent Application No. PCT/US2008/066262, entitled COMBINATION COMMUNICATION DEVICE AND MEDICAL DEVICE FOR COMMUNICATING WIRELESSLY WITH A REMOTE MEDICAL DEVICE; PCT Patent Application No, PCT/US2008066331, entitled METHOD AND APPARATUS FOR DETERMINING AND DELIVERING A DRUG BOLUS; PCT Patent Application No. PCT/US2008/066267, entitled LIQUID INFUSION PUMP; PCT Patent Application No. PCT/US2008/066299, entitled USER INTERFACE FEATURES FOR AN ELECTRONIC DEVICE; and, PCT Patent Application No. PCT/US2008/066247, entitled METHOD FOR PAIRING AND AUTHENTICATING ONE OR MORE MEDICAL DEVICES AND ONE OR MORE REMOTE ELECTRONIC DEVICES.

Figure 1:
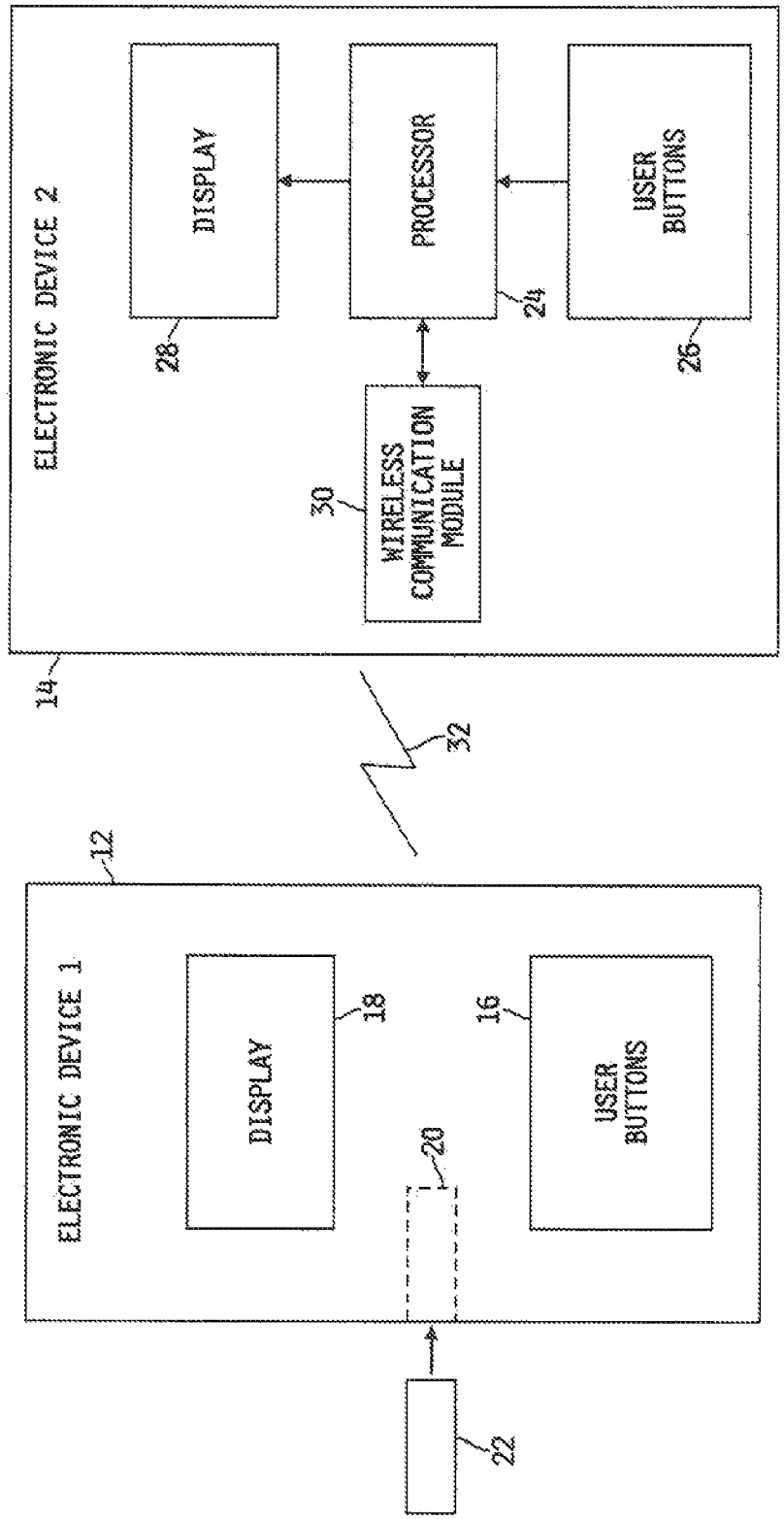
FIG. 1 shows a block diagram of one illustrative embodiment of a wireless communication system including an electronic device for determining an analyte concentration of a liquid sample and for wirelessly communicating with another electronic device.

Referring now to FIG. 1, a block diagram of one illustrative embodiment of an electronic device 12 for determining an analyte concentration of a liquid sample and for wirelessly communicating with another electronic device 14 is shown. Together, the electronic devices 12 and 14 define a wireless communication system 10.

The electronic device 12 has a housing through which a user button section 16 is received. In one embodiment, the user button section 16 defines a number of user buttons, keys or switches that may be manually manipulated by a user to accomplish one or more functions associated with the electronic device 12. A visual display unit 18 is carried by the housing of the electronic device 12, and in one embodiment the visual display unit 18 is provided in the form of a conventional liquid crystal display (LCD), although this disclosure contemplates using other conventional display units. Examples include, but are not limited to, plasma displays, light emitting diode (LED) based displays, vacuum fluorescent (VF) displays, and the like. In any case, the visual display unit 18 is controlled by the electronic device 12 to display information to a user of the device 12. In alternative embodiments, the user button section 16 may be or include one or more touch sensitive buttons. In this embodiment, one or more touch sensitive buttons may, but need not, form part of the display unit 18.

The electronic device 12 further includes a test element receiving port 20 that is configured to receive therein a test element 22. In one embodiment, the test element 22 is provided in the form of a conventional test strip defining a liquid receiving portion thereon. Alternatively, the test element 22 may be provided in the form of a conventional rigid or semi-rigid carrier defining a test portion thereon. In any case, the test element 22 is configured to receive a liquid sample on the liquid receiving portion. The test element 22 may then be inserted into the test element receiving port 20 containing an analyte determination facility including electronic circuitry configured to analyze the liquid sample in a conventional manner to determine the concentration of an analyte contained in the sample. In one embodiment, for example, the analyte determination facility may include a conventional electro-chemical sensor, and the corresponding electronic circuitry may be configured to determine the concentration of the analyte by commencing and monitoring a known electro-chemical reaction between the electro-chemical sensor and the liquid sample. Alternatively, the analyte determination facility may include conventional photometric sensing circuitry, and the corresponding electronic circuitry may be configured to determine the concentration of the analyte via conventional photometric techniques. In any case, the liquid sample may be, for example, blood and the analyte may be, for example, blood glucose. It will be understood, however, that the liquid sample may be urine or another bodily fluid, or any solution containing an analyte of unknown concentration.

The electronic device 14 includes a conventional processor 24 that is electrically connected to a wireless communication module 30. The wireless communication module 30 is configured to communicate wirelessly with a similar wireless communication module of the electronic device 12 via a wireless communication link 32 in a conventional manner. In one embodiment, as will be illustrated throughout this disclosure, the wireless communication module 30 and the wireless communication module of the electronic device 12 are both conventional BlueTooth® modules configured to wirelessly communicate according to a conventional BlueTooth® communication protocol. It will be understood, however, that the wireless communication module 30 and the wireless communication module of the electronic device 12 may alternatively be configured to wirelessly communicate according to one or more other conventional communication protocols.

The electronic device 14 may, but need not, further include a user button section 26 having a number of user selectable buttons, keys or switches that are electrically connected to the processor 24. The electronic device 14 may, but need not, further include a visual display unit 28 that is electrically connected to the processor 24. The visual display unit 28 may be, for example, a conventional liquid crystal display (LCD), plasma displays, light emitting diode (LED) based display, vacuum fluorescent (VF) display, or the like. In embodiments that include the visual display unit 28, it is controlled by the processor 24 to display information to a user of the device 14.

In one illustrative embodiment, the electronic device 14 is an ambulatory medical device. Examples of the electronic device 14 in this embodiment include, but are not limited to, an implantable medication delivery pump or a non-implantable medication delivery pump, such as a drug infusion pump, an implantable or non-implantable body condition sensor or sensor system, and the like. In embodiments in which the electronic device 14 is a medication delivery pump, the medication delivered by such a pump may include, but should not be limited to, insulin or other conventional blood glucose modifying drug. In alternative embodiments, the electronic device 14 may be or include a conventional personal, laptop or notebook computer, personal data assistant, or other conventional electronic device capable of wireless communication.

Figure 2A:
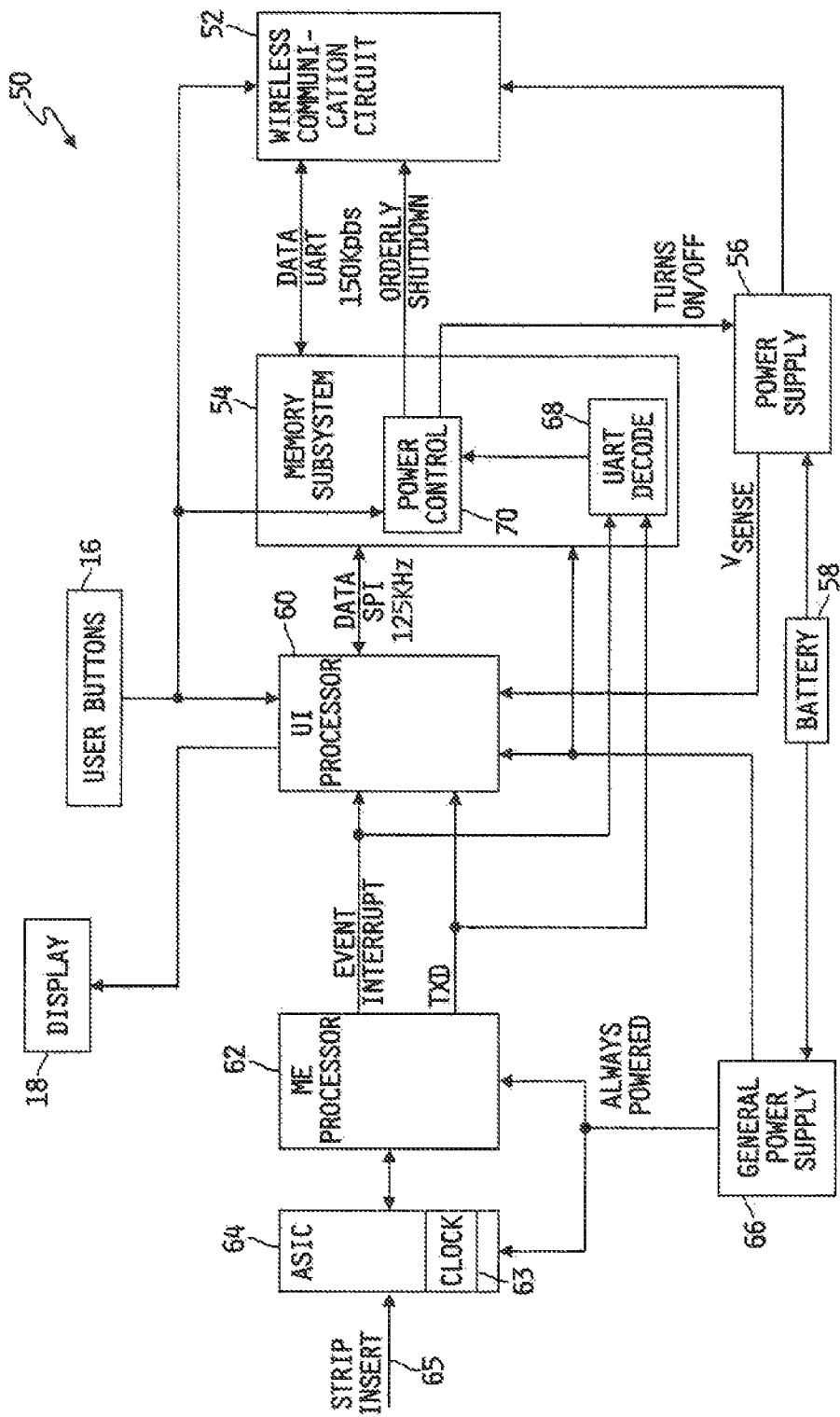
FIG. 2A shows a block diagram schematic of one illustrative embodiment of an electronic circuit that is carried by, and that controls, one of the electronic devices of FIG. 1.

Referring now to FIG. 2A, a block diagram schematic is shown of one illustrative embodiment of an electronic circuit 50 that is carried by, and that controls, the electronic device 12 of FIG. 1. In the illustrated embodiment, the electronic circuit 50 includes four modules with separate and distinct functional responsibilities. For example, the electronic circuit 50 includes a User Interface (UI) processor 60 that is the main controller of the electronic device 12. In addition to processing all aspects of the user interfaces 16, 18, it is the origination and destination of all data communicated from and to the electronic device 14. As will be described in greater detail herein, the UI processor 60 has no control over operation of the wireless communication circuit of the device 12. The UI processor 60 operates according to a UI clock signal that is generated internally to the UI processor 60. In one illustrative embodiment, the UI processor 60 is a UPD70F3719GC 32-bit microcontroller that is commercially available from NEC Electronics America of Santa Clara, Calif., although this disclosure contemplates other implementations of the UI processor 60.

The electronic circuit 50 further includes a wireless communication circuit 52 that is responsible for the control of all wireless communications with one or more electronic devices but that does not control any other operations associated with the electronic device 12. The wireless communication circuit 52 operates from a clock signal that is generated internally to the wireless communication circuit 52 and that is not synchronized to the UI clock signal from which the UI processor 60 operates. Operation of the wireless communication circuit 52 is therefore asynchronous with respect to the operation of the UI processor 60. In one illustrative embodiment, the wireless communication circuit 52 provided in the form of a conventional BlueTooth® telemetry module that includes a conventional processor and conventional wireless communication hardware. In this embodiment, the wireless communication circuit 52 is responsible for the control of all wireless communications with one or more external devices, such as the electronic device 14, via a conventional BlueTooth® communications protocol. In one illustrative embodiment, the wireless communication circuit 52 is a BC419143B BlueCore™ 4-Flash Plug-n-Go™ single chip BlueTooth® radio and baseband integrated circuit for BlueTooth® 2.4 GHz systems that is commercially available from CSR of Richardson, Tex., although this disclosure contemplates other implementations of the wireless communication circuit 52.

The electronic circuit 50 further includes a memory subsystem 54 that temporarily stores data moving between the UI processor 60 and the wireless communication circuit 52. In some embodiments, the memory subsystem 54 does not control other circuitry, and in some such embodiments the memory subsystem 54 may be provided in the form of a conventional memory device. In other embodiments in which the memory subsystem 54 does or does not control other circuitry, the memory subsystem 54 may be provided in the form of a conventional processor that is configured to operate as a Dual-Port RAM (DPR) processor. In such embodiments, the DPR processor 54 operates from a clock signal that is separate from the UI clock signal from which the UI processor 60 operates. In one embodiment, such a DPR processor 54 is a MC9S08GT16A 8-bit microcontroller unit that is commercially available from Freescale Semiconductor, Inc. of Austin, Tex., although this disclosure contemplates other implementations of the memory subsystem 54 that is provided in the form of a conventional processor configured as a DPR processor. In the embodiment illustrated in FIG. 2A, the memory subsystem 54 is DPR processor that controls operation of a power supply 56 that supplies an operating voltage to the wireless communication circuit 52.

The electronic circuit 50 further includes a Measurement Engine (ME) processor 62 that is responsible for controlling analyte concentration measurements of liquid samples contained on test elements 22, calculating analyte concentration levels of the samples, e.g., blood glucose concentration values, and reporting the results to the UI processor 60. The ME processor 62 operates from a clock signal that is separate from the UI clock signal from which the UI processor 60 operates. The ME processor 62 is electrically connected to the UI processor 60 via an Event Interrupt line and a TXD (data transmission) line. In one illustrative embodiment, the ME processor 62 is a MSP430T2AIPEG mixed-signal microcontroller unit that is commercially available from Texas Instruments, Inc. of Dallas, Tex., although this disclosure contemplates other implementations of the ME processor 62.

The electronic circuit 50 further includes an application specific integrated circuit (ASIC) 64 that includes circuitry responsible for detecting insertion of test elements 22 into the test element receiving port 20 and for providing such information to the ME processor 62. In one illustrative embodiment, for example, the test element receiving port 20 includes one or more micro-switches that provide a strip insert signal 65 to the ASIC 64 upon insertion of a test element 22 into the test element receiving port 20. In this embodiment, the ASIC 64 is operable to detect the strip insert signal 65, and to provide such information to the ME processor 62. The ASIC 64 also includes a clock circuit 63 that is programmable for a number of different functions. For example, the clock circuit 63 may be programmed to generate a signal to automatically turn on the circuit 50 and the device 12 at one or more programmable times. As another example, the clock circuit 63 may be programmed to generate a signal corresponding to one or more reminders. Other examples will occur to those skilled in the art, and such other examples are contemplated by this disclosure, in any case, the signal generated by the clock circuit 63 is provided to the ME processor 62, and the ME processor 62 is responsive to the receipt of this signal to power up from a sleep state if the ME processor 62 is in such a sleep state, and to produce an event interrupt signal on the Event Interrupt line. The event interrupt signal is received by the UI processor 60, which then powers up from a sleep state if the UI processor 60 is in such a sleep state, and/or generates an audible or visible reminder corresponding to any reminder time programmed in the clock circuit 63. In the embodiment illustrated in FIG. 2A, the ME processor 62 also generates a signal on the TXD line, to which the DPR processor 54 is responsive to activate, or turn on, the Power Supply 56 as will be described in detail hereinafter.

The electronic circuit 50 further includes a General Power Supply 66 that provides a supply voltage to the ASIC 64, the ME processor 62, the UI processor 60 and the memory subsystem 54 on a continuous basis. The supply voltage is derived from one or more rechargeable or non-rechargeable batteries (BATTERY) 58. In one illustrative embodiment, the General Power Supply 66 provides an "operating mode" supply voltage to the processors 54, 60 and 62 and to the ASIC 64 during normal operation of the electronic device 12, and also provides a "sleep mode" supply voltage to these processors when the electronic device 12 is powered down.

The Power Supply 56 provides a supply voltage to the wireless communication circuit 52 that is also derived from the one or more rechargeable or non-rechargeable batteries (BATTERY) 58. In the embodiment illustrated in FIG. 2A, the operational status ("on" and "off") of the Power Supply 56 is controlled by the DPR processor 54 based on user key presses, i.e., user activations of user buttons 16, and also based on the operational status of the test element receiving port 22. Although not shown in FIG. 2A, the electronic circuit 50 includes an additional battery that is used to operate a real-time clock contained in the UI processor 60.

The display 18 is controlled by the UI processor 60 to display information to the user. Illustratively, the display 18 includes a back light (not shown), and the test element receiving port 20 includes a port light (not shown). Both the display back light and the port light are illustratively activated and deactivated simultaneously and manually via a particular one or combination of user key presses. They are likewise deactivated either manually via one or a combination of user key presses or automatically by the UI processor 60 after a time out period following activation, in some alternate embodiments, the display backlight and the port light are separately activated, and in other alternate embodiments the port light is omitted, in any case, the UI processor 60 also controls operation of the General Power Supply 66 during power up and power down of the electronic device 12. In the illustrated embodiment, the UI processor 60 additionally monitors the operational status (e.g., "on" or "off") of the power supply 56 by monitoring the output voltage of this power supply via an output voltage sense line, $V_{SENSE}$.

Figure 2B:
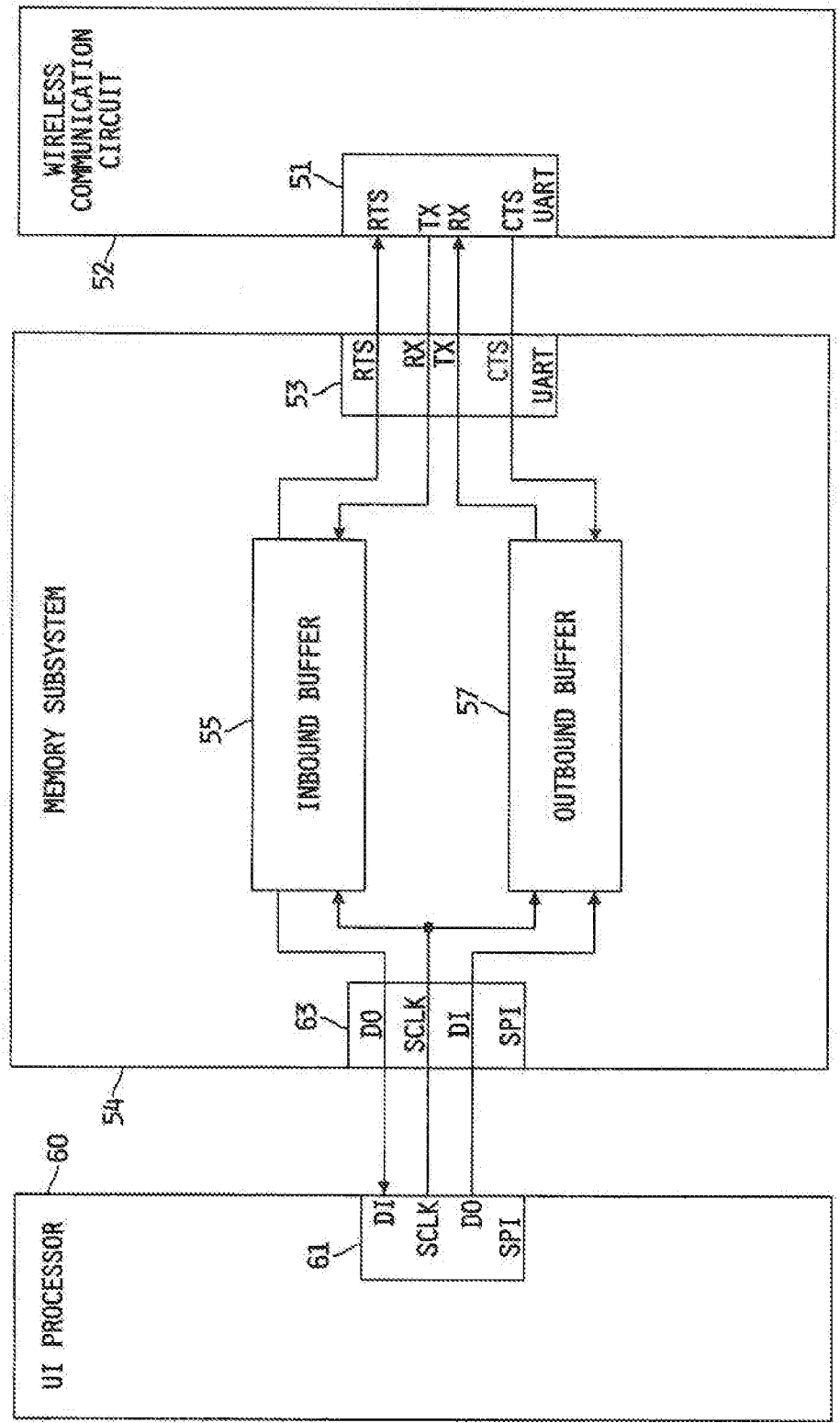
FIG. 2B shows a block diagram schematic of some of the details of one illustrative embodiment of the DPR processor of FIG. 2A including electrical connections to the UI processor and BT processor.

The memory subsystem 54 acts as an independent repository of data moving between the UI processor 60 and the wireless communication circuit 52. Referring to FIG. 2B, a block diagram of some of the details of the memory subsystem 54, illustratively implemented in the form of a DPR processor, are shown along with electrical connections to the UI processor 60 and the wireless communication circuit 52. In the illustrated embodiment, one of the dual ports of the DPR processor 54 is a serial peripheral interface (SPI) port 63 that is electrically connected solely to a serial peripheral interface port 61 of the UT processor 60 via a synchronous interface. The synchronous interface operates from a serial clock signal, SCLK, (e.g., 125 kHz) that is derived from the UI clock signal. Transfer of inbound and outbound data between the SPI port 61 of the UI processor 60 and the SPI port 63 of the DPR processor 54 is controlled by the UI processor 60 using the serial clock signal, SCLK, which is derived from the UI clock signal to synchronize data transfer between the two processors 60, 54.

The other of the dual ports of the DPR processor 54 is a universal asynchronous receiver/transmitter (UART) port 53 that is electrically connected solely to a UART port 51 of the wireless communication circuit 52 via an asynchronous interface. Transfer of inbound and outbound data between the UART port 51 of the wireless communication circuit 52 and the UART port 53 of the DPR processor 54 (e.g., at 150 kbps) is controlled by the wireless communication circuit 52, and takes place asynchronously with respect to the transfer of inbound and outbound data between the SPI port 61 of the UI processor 60 and the DPR processor 54.

The DPR processor 54 has an inbound data buffer 55 and an outbound data buffer 57 that are each accessible by the SPI and UART ports 63 and 53 respectively of the DPR processor 54. The UART port 53 of the DPR processor 54 includes conventional clear to send (CTS) and ready to send (RTS) lines. The CTS line is monitored by the DPR processor 54 and the RTS line is monitored by the wireless communication circuit 52. The DPR processor 54 deactivates the UART RTS line whenever the inbound data buffer 55 is full, and otherwise activates the UART RTS line. The wireless communication circuit 52 activates the UART CTS line whenever the UART port 51 of the wireless communication circuit 52 is requesting data, and otherwise deactivates the UART CTS line.

When data is to be sent by the UI processor 60 to an external device or system, e.g., the electronic device 14, the UI processor 60 first requests the state of the outbound data buffer 57 of the DPR processor 54. If the DPR processor 54 answers that its outbound data buffer 57 is "not full," the UI processor 60 transfers the data to the outbound data buffer 57 of the DPR processor 54 via the data out (DO) line of the SPI port 61. If the DPR processor 54 instead answers that the outbound data buffer 57 is "full," the UI processor 60 waits for a time interval and then repeats the process of requesting the state of the outbound data buffer 57, etc.

Periodically with respect to the clock signal of the wireless communication circuit 52 and asynchronously with respect to the SCLK signal, the wireless communication circuit 52 requests data from the DPR processor 54 by activating the UART CTS line of the DPR processor 54. As long as the outbound data buffer 57 of the DPR processor 54 is empty, the wireless communication circuit 52 continues to periodically activate the UART CTS line. If the UART CTS line is active and the outbound data buffer 57 of the DPR processor 54 is not empty, the wireless communication circuit 52 retrieves the data from the outbound data buffer 57 of the DPR processor 54 via the RX line of the UART port 51. The DPR processor 54 transfers the data stored in its outbound data buffer 57 to its UART port 53 in a first received to last received order until the outbound data buffer 57 has been emptied or until the wireless communication circuit 52 deactivates the UART CTS line. In the embodiment illustrated in FIGS. 2A and 2B, the wireless communication circuit 52 then incorporates the data retrieved from the outbound data buffer 57 of the DPR processor 54, via the data UART, into to the wireless communication protocol structure, e.g., BlueTooth® communication protocol structure, and wirelessly transmits the incorporated data via conventional wireless signal transmission circuitry of the wireless communication circuit 52. The wireless communication circuit 52 does not process, interpret or alter the contents of the data retrieved from the outbound data buffer 57 of the DPR processor 54, nor does it make any decisions or execute any steps based an the contents of the data. Rather, the wireless communication circuit 52 treats all such data the same, regardless of its contents, by incorporating the data into a predefined wireless communication protocol structure, e.g., BlueTooth® protocol structure, and then wirelessly transmitting the incorporated data using the predefined wireless communication protocol.

Inbound, wireless signal transmissions from external devices or systems, e.g., the electronic device 14, are received by the wireless communication circuit 52 via conventional wireless signal receiving circuitry of the wireless communication circuit 52. The wireless communication circuit 52 first isolates the inbound data from the wireless communication protocol structure, e.g., BlueTooth® protocol structure, and then checks the status of the UART RTS line of the DPR processor 54. If the RTS line is activated, indicating that the inbound data buffer 55 of the DPR processor 54 is not full, the wireless communication circuit 52 sends the isolated data to the UART port 53 of the DPR processor 54. The DPR processor 54 then places the data received at the UART port 53 into the inbound data buffer 55 of the DPR processor 54, if the UART RTS line is deactivated, indicating that the inbound data buffer 55 of the DPR processor 54 is full, the wireless communication processor 52 waits for a time interval before rechecking the state of the UART RTS line.

Periodically, and asynchronously with respect to the operation of the wireless communication circuit 52, the UI processor 60 requests the state of the inbound data buffer 55 of the DPR processor 54 via the data in (DI) line of the SPI port 61. As long as the DPR processor 54 answers that the inbound data buffer 55 is empty, the UI processor 60 continues to periodically request the state of the inbound data buffer 55. If the DPR processor 54 answers that the inbound data buffer 55 of the DPR processor 54 contains data, the UI processor 60 retrieves the data from the inbound data buffer 55 of the DPR processor 54 via data in (DI) line of the SPI port 61, and then processes the data according to its contents. "Checking" the inbound and/or outbound data buffer 55, 57 of the DPR processor 54 by the wireless communication circuit 54 and/or UI processor 60, as this term may be used hereinafter, will generally refer to the process just described in the preceding several paragraphs.

While FIG. 2B, and several other figures of this disclosure, illustrates an embodiment in which the interface between the UI processor 60 and the memory subsystem 54 is a synchronous interface and the interface between the wireless communication circuit 54 and the memory subsystem 54 is an asynchronous interface, this disclosure contemplates alternative embodiments in which the interface between the UI processor 60 and the memory subsystem 54 is an asynchronous interface and the interface between the wireless communication circuit 52 and the memory subsystem 54 is a synchronous interface or in which both interfaces are asynchronous or synchronous interfaces. In the latter case, the UI processor 60 and the wireless communication circuit 52 will operate according to separate, independently operating and non-synchronized clock signals. In any case, the UI microprocessor 60 operates at all times independently and asynchronously with respect to the operation of the wireless communication circuit 52, and the wireless communication circuit 52 likewise operates independently and asynchronously with respect to the operation of the UI microprocessor 60.

Illustratively, the electronic devices 12 and 14 may be paired according to a pairing process that establishes secure communications between the electronic device 12 and a particular electronic device 14. Illustratively, this process may be carried out to initially establish wireless communications between the electronic device 12 and a particular electronic device 14, and then again if the electronic device 12 is to be paired with a different electronic device 14. In one illustrative embodiment, the electronic device 12 may only be paired with a single electronic device 14 at a time, although this disclosure contemplates other embodiments in which the electronic device 12 may be paired with any number of electronic devices 14 and/or in which the electronic device 14 may be paired with any number of electronic devices 12. In any case, further details relating to one illustrative pairing and authentication process are provided in co-pending PCT Patent Application No. PCT/US2008/066247, entitled METHOD FOR PAIRING AND AUTHENTICATING ONE OR MORE MEDICAL DEVICES AND ONE OR MORE REMOTE ELECTRONIC DEVICES, the disclosure of which has been incorporated herein by reference.

In the embodiment illustrated in FIG. 2A, operation of the Power Supply 56 is controlled by the DPR processor 54. Illustratively, the DPR processor 54 has a power control module 70 that is responsive to a number of different events to control an electronic switch (not shown) in the Power Supply 56 to correspondingly enable or disable operation of, i.e., turn on and off, the Power Supply 56. In the embodiment illustrated in FIG. 2A, events which the DPR processor 54 uses to control the operational status of the BT Power Supply 56 include, but need not be limited to, user press(es) of one or a combination of the user buttons 16, insertion of a test element 22 into the test element receiving port 20, completion of an analysis of fluid deposited on a test element 22 and manual power up/down of the electronic device 12.

An ON/OFF button of the electronic device 12 (not shown explicitly, but forming part of the user buttons 16) is an input to both the UI processor 60 and to the DPR processor 54. When the device 12 is powered off and the user presses the ON/OFF button, the corresponding ON signal presented to the DPR processor 54 causes the power control module 70 of the DPR processor 54 to output a "power up" signal that controls the electronic switch in the Power Supply 56 to enable or turn on the Power Supply 56. When enabled or turned on, the Power Supply 56 provides a supply voltage to the wireless communication circuit 52. When the Power Supply 56 is enabled or turned on and the user presses the ON/OFF button of the device 12, the corresponding OFF signal presented to the DPR processor 54 causes the power control module 70 of the DPR processor 54 to output an "orderly shutdown" signal that is received by the wireless communication circuit 52. The wireless communication circuit 52 is responsive to the "orderly shutdown" signal to undergo a conventional orderly shutdown process. After a fixed delay time following production of the "orderly shutdown signal," the power control module 70 of the DPR processor 54 produces a "power down" signal that controls the electronic switch in the Power Supply 56 to disable, e.g., turn off, the Power Supply 56. When disabled or turned off the Power Supply 56 does not provide the supply voltage to the wireless communication circuit 52.

The test element receiving port 20 of the electronic device 12 is monitored by the ME processor 62. When the strip insert signal 65 detected, the ME processor 62 produces a corresponding "strip insertion" message on the TXD line that is received by the UI processor 60 and that is also received by a UART decode logic block 68 of the DPR processor 54. The ME processor 62 also produces an event signal on the event interrupt line in response to detection of the strip insert signal 65. The "strip insertion" message is processed by the UART decode logic block 68 to produce a trigger signal, which is provided to the power control module 70 of the DPR processor 54. The power control module 70 processes the trigger signal received from the UART decode logic block 68 to produce the "orderly shutdown" signal and also the "power down" signal, as described above. The "orderly shutdown" signal causes the wireless communication circuit 52 to undergo the orderly shutdown process described above, and the "power down" signal is received by the Power Supply 56. The Power Supply 56 is responsive to the "power down" signal to power down, i.e., turn off. The power control module 70 and the UART decode logic block 68 of the DPR processor 54 are configured such that the strip insertion message produced by the ME processor 62 on the TXD line overrides, and has priority over, the ON/OFF signal described above. Thus, detection of a strip insertion event will dictate the operational status of the wireless communication circuit 52 and of the Power Supply 56 regardless of the state of the ON/OFF key.

When an analyte concentration value is determined by the ME processor 62 following insertion of a test element 22 into the test element receiver port 20, the ME processor 62 produces a corresponding "test complete" message on the TXD line. When the "test complete" message is received by the UART decode logic block 68 of the DPR processor 54, the power control module 70 of the DPR processor 54 outputs a "power up" signal, which is received by the Power Supply 56. The Power supply 56 is responsive to the "power up" signal to power up, i.e., turn on. The UI processor 60 is electrically connected to the Power Supply 56 via a $V_{SENSE}$ line, and the voltage of the $V_{SENSE}$ line is a low-current mirror voltage of the supply voltage provided by the Power Supply 56 to the wireless communication circuit 52. The UI processor 60 monitors the state of the Power supply 56 by monitoring the $V_{SENSE}$ line, and when the UI processor 60 detects that the Power Supply 56 has been enabled, i.e., has powered up, the UI processor 60 attempts to make a wireless connection with the electronic device 14 as will be described in greater detail below.

The electronic device 12 is also configured to permit a user to manually disable the Power Supply 56. A combination of two or more user activated keys or buttons 16 on the electronic device 12 that provide corresponding signals to both the DPR processor 54 and the UI processor 60 are illustratively used to accomplish a manual shut down of the Power Supply 56. When the electronic device 12 is on, when the Power supply 56 is enabled to provide its supply voltage to the wireless communication circuit 52, and when the user presses a predefined combination of two or more of the buttons or keys 16 at the same time, the DPR processor 54 is responsive to the combination of key presses to control power down of the Power Supply 56 after an orderly shutdown of the wireless communication circuit 52 as described above. Conversely, when the electronic device 12 is on, when the Power Supply 56 is disabled, and when the user presses the predefined combination of buttons or keys 16 at the same time, the DPR processor 54 is responsive to the combination of key presses to power up the Power Supply 56 and the wireless communication circuit 52 as described above. The UI processor 60 and the wireless communication circuit 52 independently store this information in non-volatile memory.

The UI processor 60 controls the display 18 of the electronic device 12 to indicate the connection status of the wireless communication circuit 52 relative to the wireless telemetry system of the electronic device 14. Upon power up of the electronic device 12, and also following enablement of the Power Supply 56 after being disabled as described above, the UI processor 60 controls the display 18 to display a flashing (or fixed) icon to indicate that a wireless connection is not established between the electronic device 12 and the electronic device 14. The UI processor 60 independently controls the display 18 in this manner without any information provided by the wireless communication circuit 52. The UT processor 60 then places data into the data buffer of the outbound port of the DPR processor 54, as described above, wherein the data in this case includes a command to transmit an acknowledgement response back to the electronic device 12. The wireless communication circuit 52 then transmits this data as described above. If the electronic device 14 is within range, the electronic device 14 receives the command and responds by transmitting an acknowledgement signal. If the acknowledgement signal is received by the electronic device 12, the wireless communication circuit 52 is operable as described above to isolate the data from the wireless communication protocol structure and place the data in the data buffer of the inbound port of the DPR processor 54. The UI processor 60 then retrieves the data from the inbound port of the DPR processor 54, processes the data and determines that it contains the requested acknowledgement response, and controls the display 18 in accordance with the acknowledgement response to display a fixed (or flashing) icon to indicate that a wireless connection is established between the electronic devices 12 and 14. The electronic device 12 periodically transmits a wireless connection status request to the electronic device 14 in the above fashion at regular intervals. As long as the electronic device 14 responds as just described, the UI processor 60 controls the display 18 to display the fixed (or flashing) icon to indicate that a wireless connection exists between the electronic devices 12 and 14. If the UI processor 60 does not receive such a response within a predefined time period following storage of the acknowledgement response command in the DPR processor 54, the UI processor 60 controls the display 18 to display a flashing (or fixed) icon indicating that the wireless connection between the electronic devices 12 and 14 does not exist or no longer exists.

As described above, the UI processor 60 monitors the state of the Power supply 56 via the $V_{SENSE}$ line. When the UI processor 60 determines from the $V_{SENSE}$ signal that the Power Supply 56 is enabled, i.e., turned on, the UI processor 60 controls the display 18 to display a fixed or flashing icon that is indicative of the On or enabled state of the Power Supply 56. When the UI processor 60 determines from the $V_{SENSE}$ signal that the Power Supply 56 is disabled, the UI processor 60 controls the display 18 to display an indicator that is indicative of the Off or disabled state of the Power Supply 56. In one illustrative embodiment, the UI processor 60 controls the display 18 to indicate that the Power Supply 56 is disabled by displaying a flashing or icon, although it will be understood that the UI processor 60 may control the display 18 in an alternate fashion to indicate that the Power Supply 56 is disabled.

Figure 3:
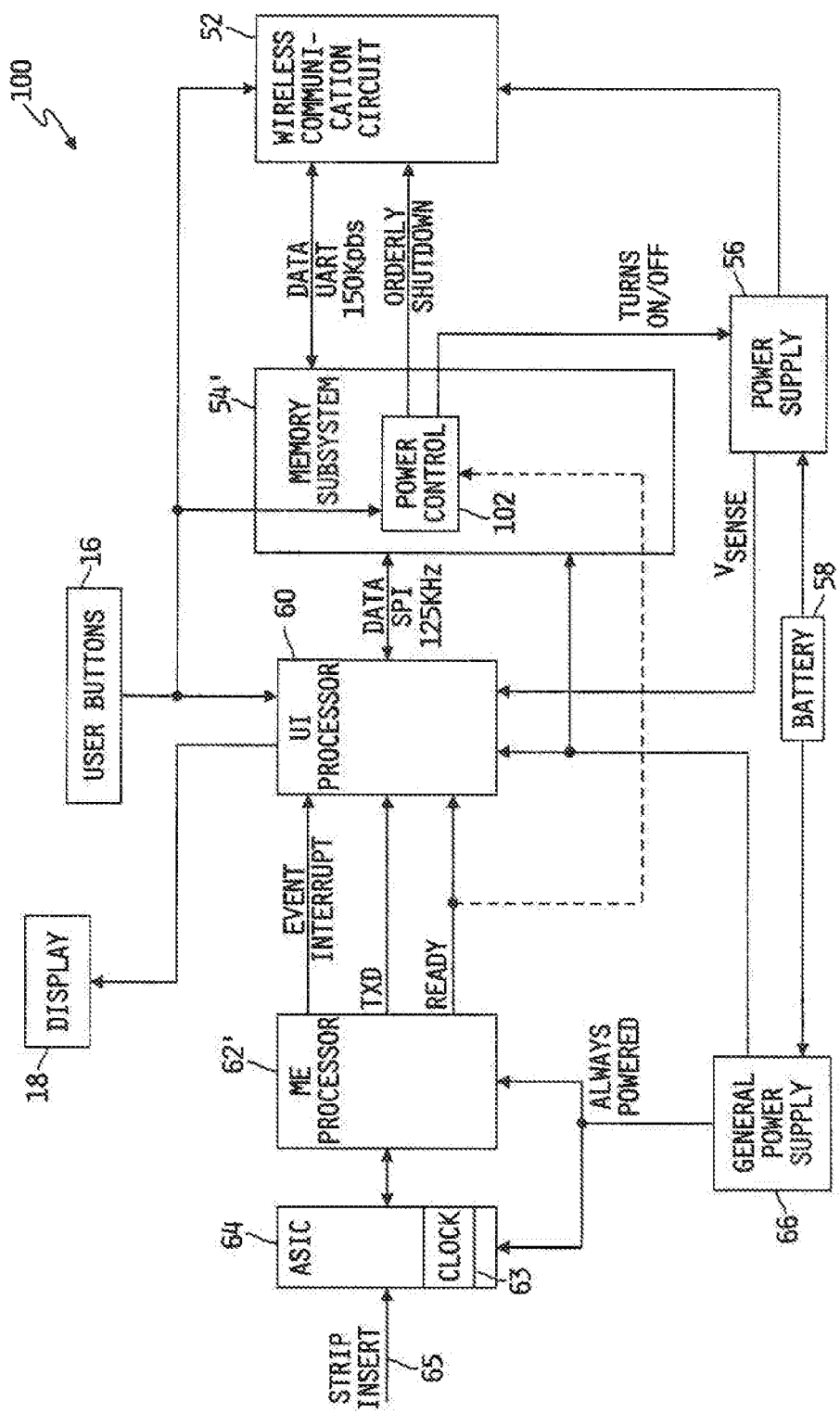
FIG. 3 shows a block diagram schematic of another illustrative embodiment of an electronic circuit that is carried by, and that controls, one of the electronic devices of FIG. 1.

Referring now to FIG. 3, a block diagram schematic of another illustrative embodiment 100 of the electronic circuit that is carried by, and that controls, the electronic device 12 of FIG. 1 is shown. The electronic circuit 100 is identical in much of its structure and operation to the electronic circuit 50 illustrated in FIGS. 2A and 2B, and described hereinabove. Like numbers are used in FIG. 3 to identify like components in FIGS. 2A and 2B, and descriptions of these like components and functions will not be repeated here for brevity. The electronic circuit 100 differs from the electronic circuit 50 in that the ME processor 62' in this embodiment has an additional output line, Ready, that is electrically connected to the UT processor 60 and also to the memory subsystem 54' which, in the embodiment illustrated in FIG. 3, is illustratively provided in the form of a DPR processor. In this embodiment, however, the DPR processor 54' is different from the DPR processor 54 of FIG. 2A in that the UART decode logic is omitted from the DPR processor 54' which instead, includes only a power control logic block 102. The Event Interrupt and TXD lines of the ME processor 62' connect only to the UI processor 60, and the Ready line of the ME processor 62' may or may not connect directly to the power control module 102 as indicated by dashed-line representation in FIG. 3.

In one illustrative embodiment of the electronic circuit 100, the Ready line is directly connected to the power control module 102. In this embodiment, any event, e.g., those described above, that is determined by the ASIC 64 to require power up of the power supply 56 is notified to the ME processor 62' which produces a corresponding event signal on the Ready line. The power control module 102 is responsive to the Ready signal to activate, i.e., turn on, the Power supply 56 as described hereinabove, and the UI processor 60 is responsive to the Ready signal to control the display 18 to indicate the operational statuses of the wireless communication circuit 52 and Power Supply 56.

In another illustrative embodiment of the electronic circuit 100, the Ready line is not connected to the power control module 102 of the DPR processor 54', but rather only to the UI processor 60. In this embodiment, as with the previous embodiment, any event, e.g., those described above, that is determined by the ASIC 64 to require power up of the power supply 56 is notified to the ME processor 62', and the ME processor 62' produces a corresponding event signal on the Ready line. Only the UI processor 60 receives the Ready signal in this embodiment, and when the UI processor 60 wakes up, it is responsive to the Ready signal to display a message on the display 18 that instructs the user of the device 12 to press the ON button (part of the user buttons 16) if the user wishes to communicate wirelessly with the electronic device 14 (see FIG. 1). If/when the user presses the ON button, the power control module 102 of the DPR processor 54' is responsive to the corresponding ON signal produced by the user buttons 16 to activate, i.e., turn on, the Power supply 56 as described hereinabove. Thus, the ME processor 62' does not directly control activation of the Power Supply 56 in this embodiment. Rather, the user must manually activate the Power Supply 56 in this embodiment by pressing the ON button.

Figure 4:
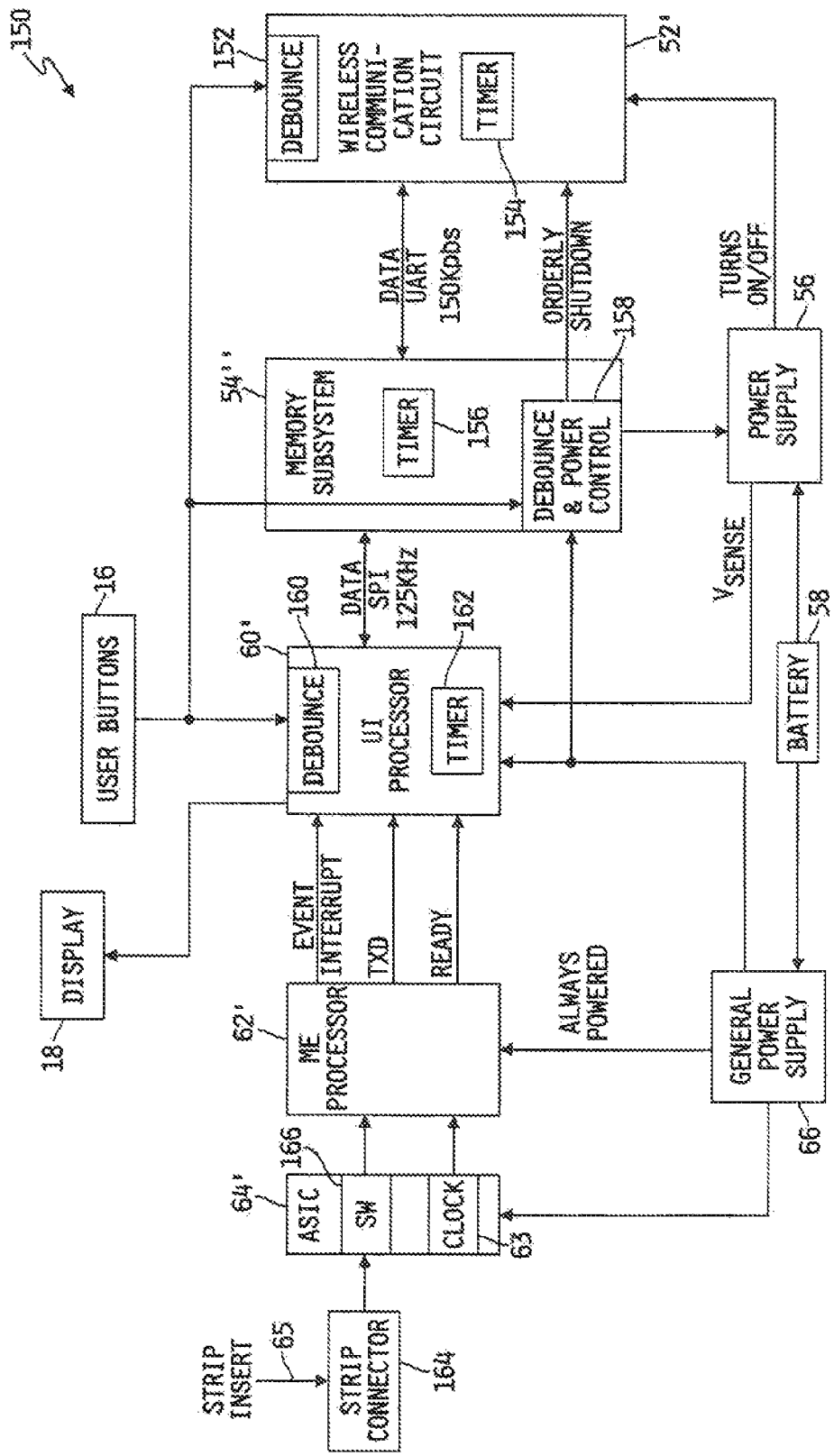
FIG. 4 shows a block diagram schematic of yet another illustrative embodiment of an electronic circuit that is carried by, and that controls, one of the electronic devices of FIG. 1.

Referring now to FIG. 4, a block diagram schematic of another illustrative embodiment 150 of the electronic circuit that is carried by, and that controls, the electronic device 12 of FIG. 1 is shown. The electronic circuit 150 is identical in some of its structure and operation to the electronic circuits 50 and 100 illustrated in FIGS. 2A, 2B and 3 and described hereinabove. Like numbers are used in FIG. 4 to identify like components in FIGS. 2A, 2B and 3, and descriptions of these like components and functions will not be repeated here for brevity. The electronic circuit 150 differs from the electronic circuit 50 in that the wireless communication circuit 52' in this embodiment includes debounce circuitry that acts a an interface between the user buttons 16 and the wireless communication circuit 52'. The debounce circuitry is conventional in that it reduces the sensitivity of the wireless communication circuit 52' to spurious switching events associated with the user buttons 16, thereby increasing the likelihood that only actual button presses are detected by the wireless communication circuit 52'. The wireless communication circuit 52' further includes in this embodiment a conventional timer circuit 154. The memory subsystem 54" in this embodiment is again illustratively provided in the form of a DPR processor that differs from the DPR processor 54' of FIG. 3 in that the power control module 158 includes conventional debounce circuitry, and the DPR processor 54" further includes a conventional timer circuit 156. The UI processor 60' in this embodiment likewise differs from the UI processor 60 of FIGS. 2 and 3 in that it includes conventional debounce circuitry 160 and a conventional timer circuit 162. The ASIC 64' in this embodiment differs from the ASIC 64 of FIGS. 2 and 3 in that it contains an electronic switch 166 that is electrically connected between a strip connector 164 and the ME processor 62'. The strip connector 164 represents an interface connector between the ASIC 64' and the strip insert signal 65. The strip connector 164 may also be included in the embodiments illustrated in FIGS. 2 and 3. In this embodiment, the Ready line is electrically connected only between the ME processor 62' and the UI processor 60'.

During information exchange between the electronic devices 12 and 14 in accordance with one embodiment of the electronic circuit 150, the UI processor 60' is operable to periodically, e.g., every 100 milliseconds, transfer query data to the outbound data buffer 57 of the DPR processor 54" and to reset its timer circuit 162. The wireless communication circuit 52' asynchronously retrieves the data from the outbound data buffer 57 of the DPR processor 54" and transmits the data to the electronic device 14 as described above. The electronic device 14 is then responsive to receipt of the query packet to immediately transmit an acknowledgement signal back to the electronic device 12. The acknowledgement signal is received by the wireless communication circuit 52', and the wireless communication circuit 52' unpacks the data from the wireless communication protocol as described above and stores the data in the inbound data buffer 55 of the DPR processor 54". The UI processor 60' then retrieves the data from the inbound data buffer 55 of the DPR processor 54", asynchronously with respect to the operation of the wireless communication circuit 52', and processes the data to determine that it contains acknowledgement response data from the electronic device 14. As long as the acknowledgement data is received by the UI processor 60' before the next scheduled transfer of query data to the outbound data buffer 57 of the DPR processor 54", the UI processor 60' resets its timer circuit 162 when transferring the next query data to the DPR processor 54". However, if acknowledgement data is not received by the UI processor 60' before the next scheduled transfer of query data to the outbound data buffer 57 of the DPR processor 54", the UI processor 60' transfers the next query data to the outbound data buffer 57 of the DPR processor 54" without resetting its timer circuit 162. If no acknowledgement data is received by the UI processor 60' within a predefined or programmed time period, e.g., 1-2 minutes, since last resetting the timer circuit 162, the timer circuit 162 times out and the UI processor 60' stops transferring query data to the outbound data buffer 57 of the DPR processor 54".

In this embodiment, the DPR processor 54" is operable to monitor the status of its outbound data buffer 57, and to control the state of the Power Supply 56 based on this status. The DPR processor 54" resets its timer circuit 156 each time that query data is stored in its outbound data buffer 57 by the UI processor 60'. As long as data gets stored in the outbound data buffer 57 before a predefined or programmed time period, e.g., 200 milliseconds, elapses since last resetting the timer circuit 156, the DPR processor 54" will continue to reset its timer circuit 156 and the power control module 158 of the DPR processor 54" will maintain the Power Supply 56 in its enabled, e.g., on, state. If no data gets stored in the outbound data buffer 57 before the predefined or programmed time period elapses after resetting the timer circuit 156, the power control module 158 deactivates, i.e., turns off, the Power Supply 56. If/when the UI processor 60' thereafter stores data in the outbound data buffer 57 of the DPR processor 54", such as when the device 12 powers up (and upon the occurrence of other events), the DPR processor 54" resets its timer circuit 156 and the power control module 158 activates, i.e., turns on, the Power Supply 56.

When strip insert is detected, the ME processor 62' notifies the UI processor 60' of this event via the Event interrupt, TXD and/or Ready line. The UI processor 60' is responsive to the strip insert notification to cease sending query data to the outbound data buffer 57 of the DPR processor 54". The DPR processor 54" then deactivates, i.e., turns off, the Power Supply 56 when the DPR processor 54" does not reset the timer circuit 156 after the predefined time period, e.g., 200 milliseconds, elapses since last resetting the timer circuit 156 as just described. When the analyte measurement test is complete, the UI processor 60' resumes sending query data to the outbound data buffer 57 of the DPR processor 54", and the DPR processor 54" is responsive to the data in its outbound data buffer 57 to reset the timer circuit 156 as described above. Resetting of the timer circuit 156 as just described then causes the DPR processor 54" to re-enable, i.e., turn on, the Power Supply 56. Thus, the DPR processor 54" turns off the Power Supply 56, thereby deactivating the wireless communication circuit 52', for the duration of every analyte measurement event, and then turns on the Power Supply 56, thereby reactivating the wireless communication circuit 52', when the analyte measurement event is complete.

In this embodiment, as with the embodiment of FIG. 3, any event, e.g., those described above, that is determined by the ASIC 64 to require power up of the power supply 56 is notified to the ME processor 62', and the ME processor 62' produces a corresponding event signal on the Event Interrupt, TXD and/or Ready line. Only the UI processor 60' receives these signals, and the UI processor 60' is responsive to any such signals that require communications with the medical device 14' to begin periodically sending query data to the outbound data buffer 57 of the DPR processor 54". This then causes the DPR processor 54" to activate, i.e., turn on, the Power Supply 56 as described above.

In an alternate embodiment of the electronic circuit 150 of FIG. 4, the Power Supply 56 is activated and deactivated, i.e., turned on and off, by the debounce and power control module 158 of the DPR processor 54" pursuant to user presses of one or more of the user buttons 16. In this embodiment, for example, the debounce and power control module 158 is responsive to user press of the On button to turn on the Power Supply 56 when the device 12 is off, and to turn off the Power Supply 56 when the device 12 is on. The debounce and power control module 158 is further responsive to a predefined sequence or combination of button presses, or to a dedicated button, to turn on or off the Power Supply 56 when the device 12 is on. Illustratively, the dedicated button may be part of the user buttons 16, or may be remotely located on the device 12, e.g., in a well in which the one or more batteries 58 is/are located.

In this alternate embodiment, detection of a strip insert does not directly result in turning on or off the Power Supply 56. If the Power Supply 56 is on when the strip insert is detected, the Power Supply 56 may remain on throughout the duration of the analyte determination test. If, on the other hand, the remainder of the circuit 150 is powered up from an off state in response to detection of the strip insert signal, the Power Supply 56 may remain off for the duration of the analyte determination test. When power to the wireless communication circuit 52' is necessary for transmission of information to the electronic device 14, such as pursuant to a reminder or automatic on, or pursuant to a data transfer initiated by the UI processor 60', the UI processor 60' controls the display 18 to display instructions to the user to manually, i.e., via a predefined sequence or combination of the user buttons 16, turn on the Power Supply 56.

As with the previous embodiment described above, the debounce and power control module 158 of the DPR processor 54" may turn off the Power Supply 56 after a predefined time period elapses without some type of information being stored in the outbound data buffer 57 of the DPR processor 54" by the UI processor 60'. Alternatively, the wireless communication circuit 52' may be configured to monitor the outbound data buffer 57 of the DPR processor 54", and to reset its timer circuit 154 only if information is found therein. If the timer circuit 154 times out because no information is found in the outbound data buffer 57 of the DPR processor 54" after a predefined or programmed time period, the wireless communication circuit 52' may transition to a low power sleep state or to successively lower power sleep states as will be described in greater detail hereinafter with respect to FIG. 5.

Figure 5:
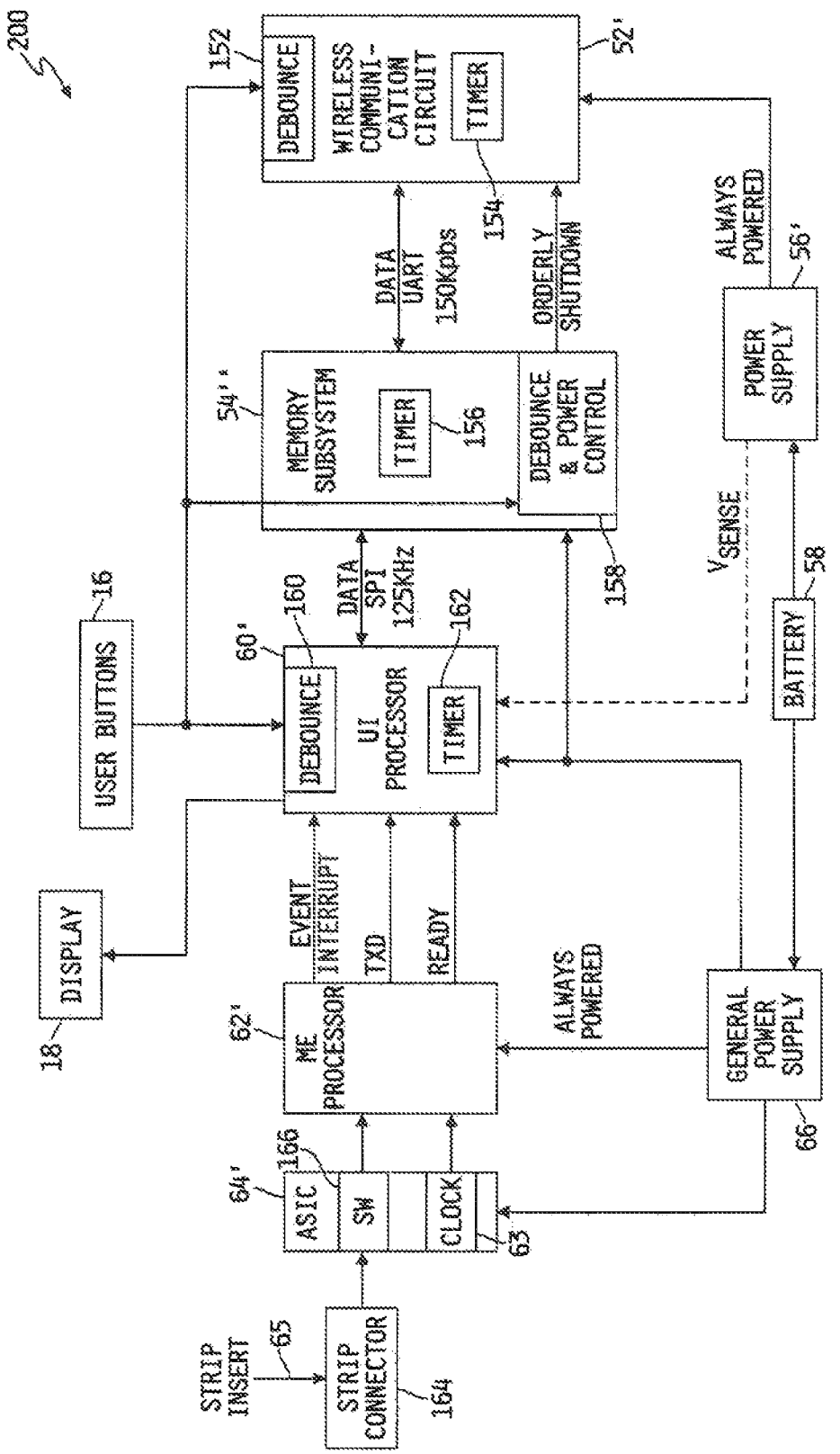
FIG. 5 shows a block diagram schematic of still another illustrative embodiment of an electronic circuit that is carried by, and that controls, one of the electronic devices of FIG. 1.

Referring now to FIG. 5, a block diagram schematic of another illustrative embodiment 200 of the electronic circuit that is carried by, and that controls, the electronic device 12 of FIG. 1 is shown. The electronic circuit 200 is identical in much of its structure and operation to the electronic circuit 150 illustrated in FIG. 4 and described hereinabove. Like numbers are used in FIG. 5 to identify components in common with FIG. 4, and descriptions of these common components and functions will not be repeated here for brevity. The electronic circuit 200 differs from the electronic circuit 150 in that the debounce and power control module 158 of the memory subsystem 54", which is provided in this embodiment in the form of a DPR processor, is not electrically connected to the Power Supply 56', and is instead connected only to the wireless communication circuit 52'. Wireless signals containing query data are periodically sent, as described above, by the device 12 to the device 14, and the device 14 responds to the query data by sending acknowledgement signals back to the device 12. The device 14 ceases to send acknowledgement signals back to the device 12 after a predefined or programmed time period, e.g., 2 minutes, has passed without receiving a wireless signal containing query data. In the embodiment of FIG. 5, the $V_{SENSE}$ line may or may not be connected between the Power Supply 56' and the UI processor 60', and the $V_{SENSE}$ line is therefore represented as a dashed line in FIG. 5.

In one embodiment of the electronic circuit 200, the wireless communication circuit 52' is always powered by the Power Supply 56', and the wireless communication circuit 52' is responsive to a number of different events to transition itself into, and out of, any of a plurality of different low power states. For example, when in a fully powered "awake" state, the wireless communication circuit 52' is operable to periodically, e.g., every 100-200 milliseconds, check the outbound data buffer 57 of the DPR processor 54" as described above. Each time the wireless communication circuit 52' finds data in the outbound data buffer 57 of the DPR processor 54", the wireless communication circuit 52' resets the timer circuit 154, incorporates the data according to the predetermined wireless communication protocol structure, and wirelessly transmits the corresponding signal to the device 14. The wireless communication circuit 52' transitions to a first low power state if it fails to find data in the outbound data buffer 57 of the DPR processor 54" when a first predefined time period elapses since last resetting the timer circuit 154. Thereafter, the wireless communication circuit 52' transitions to successively lower power states as successively longer time periods elapse since last resetting the timer circuit 154, but the wireless communication circuit 52' never turns completely off.

The number of different power states generally range between full (100%) power and a lowest power "deep sleep" state. When in the lowest power "deep sleep" state, the wireless communication circuit 52' periodically, e.g., every 400 milliseconds, wakes up to a "UART only" state, in which the wireless communication circuit 52' has sufficient power to check the status of the outbound data buffer 57 of the DPR processor 54" via the data UART line. If the outbound data buffer 57 of the DPR processor 54" has data stored therein, the wireless communication circuit 52' wakes up to a full power state to service the data. If on the other hand, the outbound data buffer 57 of the DPR processor 54" has no data, stored therein, the wireless communication circuit 52' transitions back to the lowest power "deep sleep" state.

The wireless communication circuit 52' transitions itself between lower power states and the fully powered state in response to a number of different events and mechanisms. For example, the wireless communication circuit 52' directly monitors activity of the user buttons 16 via the debounce circuitry 152, and when the wireless communication circuit 52' detects user press of the ON button, the wireless communication circuit 52' transitions itself from any of the lower power states to the full power state. Thus, in the lowest power "deep sleep" state, the wireless communication circuit 52' must be capable of monitoring at least the ON button of the user buttons 16. The DPR processor 54" is likewise operable to monitor activity of the user buttons 16, and to transition itself from a sleep state to a full power state upon detection of a user press of the ON button. Similarly, when the wireless communication circuit 52' detects user press of the OFF button, the wireless communication circuit 52' transitions itself from any of the power states to the lowest power "deep sleep" state.

As another example, when the device 12 is off and the clock circuit 63 in the ASIC sends a signal to the ME processor 62' to automatically power up the device 12, the ME processor 62' sends an automatic power up signal to the UI processor 60' via the Event interrupt, TXD and/or Ready lines as described above. When the UI processor 60' powers up, it begins periodically storing query data in the outbound data buffer 57 of the DPR processor 54" as described previously. The wireless communication circuit 52', which is in the lowest power "deep sleep" state at this point, periodically, e.g., every 400 milliseconds, transitions to the "UART only" power state and checks the outbound data buffer 57 of the PR processor 54". When the wireless communication circuit 52' finds data in the outbound data buffer 57 of the DPR processor 54", the wireless communication circuit 52' transitions to the full power state to service the data.

The UI processor 60' is operable to cease storing query data in the outbound data buffer 57 of the DPR processor 54" upon detection of a strip insert as described above. When the timer circuit 154 of the wireless communication circuit 52' reaches its first timer value after the wireless communication circuit 52' fails to find data in the outbound data buffer 57 of the DPR processor 54", the wireless communication circuit 52' begins transitioning to lower power states as described above. When the UI processor 60' then resumes storing query data in the outbound data buffer 57 of the DPR processor 54" after the analyte measurement test is complete, the wireless communication circuit 52' wakes up to full power to service the data. This may take as long as, e.g., 400 milliseconds if the wireless communication circuit 52' has just entered the lowest power "deep sleep" state when data is stored in the outbound data buffer 57 of the DPR processor 54".

In this embodiment of the electronic circuit 200, the $V_{SENSE}$ line is omitted, and the UI processor 60' is operable to control the Power Supply On/Off status indicator on the display 18 in accordance with user button activity, as described above, and also in accordance with whether or not the UI processor 60' is periodically storing query data in the outbound data buffer 57 of the DPR processor 54". Thus, if the UI processor 60' ceases storing query data in the outbound data buffer 57 of the DPR processor 54", the UI processor 60' turns off the Power Supply On/Off status indicator on the display 18 when the wireless communication circuit 52' begins to power down, e.g., 400 milliseconds after storing the last query data in the outbound data buffer 57 of the DPR processor 54". Similarly, when the UI processor 60' resumes periodically storing query data in the outbound data buffer 57 of the DPR processor 54", the UI processor 60' turns on the Power Supply On/Off status indicator on the display 18 when the wireless communication circuit 52' has transitioned to full power, e.g., 400 milliseconds after storing the first query data in the outbound data buffer 57 of the DPR processor 54".

In an alternate embodiment of the electronic circuit 200, the electronic circuit 200 is operable as just described with a few exceptions. A first exception is that, in this alternate embodiment, the wireless communication circuit 52' is responsive to a predefined combination of presses, simultaneous or otherwise, of two or more of the user buttons 16 to power itself completely off from any of its full or reduced power states. The wireless communication circuit 52' is responsive to the same predefined combination of two or more user button presses to power up to full (100%) power from its completely off state and from any of its reduced power states. In the alternate embodiment of the electronic circuit 200, the $V_{SENSE}$ line is connected between the Power Supply 56' and the UI processor 60'. In this embodiment, the UI processor 60' is operable to control the Power Supply On/Off indicator on the display 18 in accordance with the $V_{SENSE}$ signal as described above.

Figure 6:
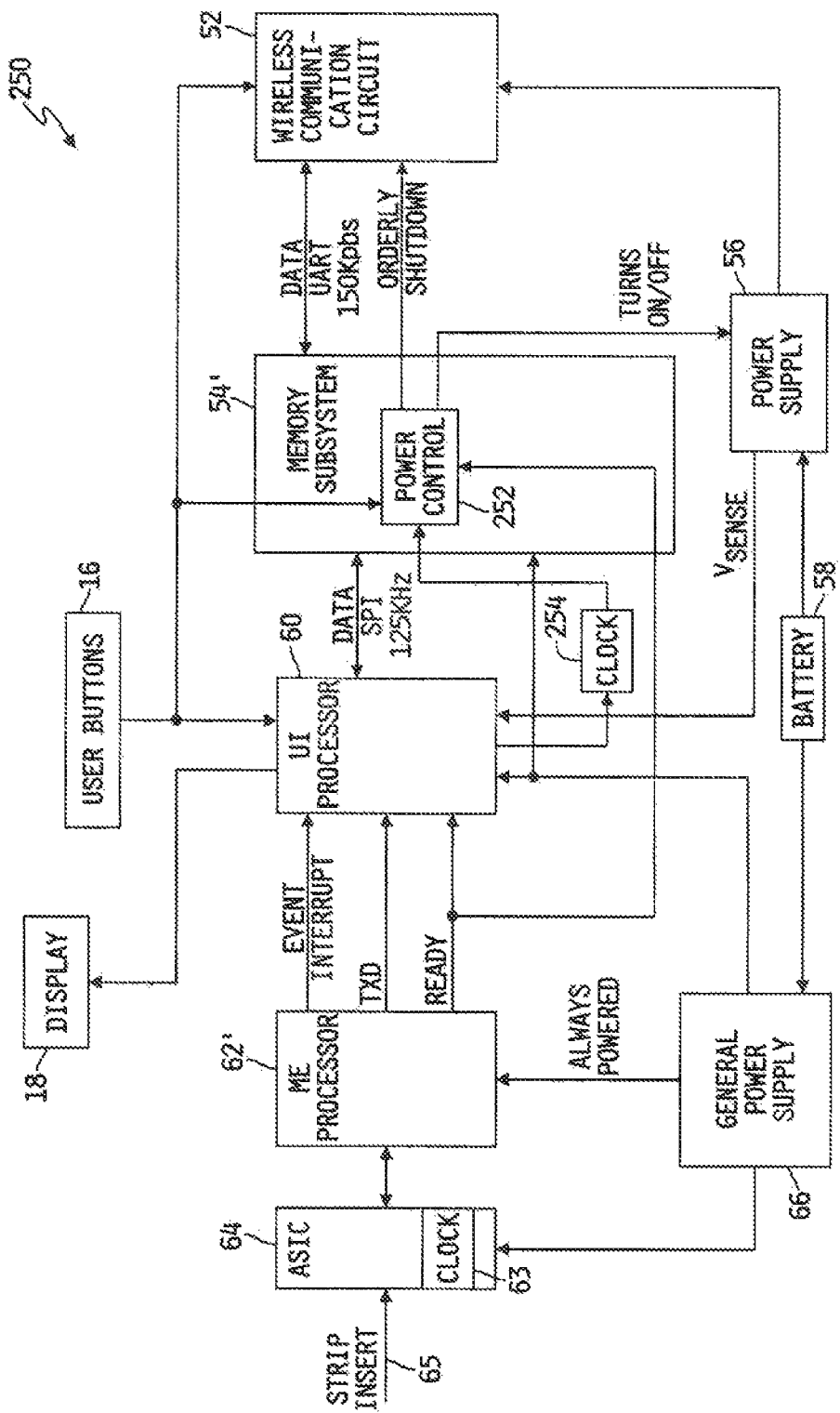
FIG. 6 shows a block diagram schematic of a further illustrative embodiment of an electronic circuit that is carried by, and that controls, one of the electronic devices of FIG. 1.

Referring now to FIG. 6, a block diagram schematic of another illustrative embodiment 250 of the electronic circuit that is carried by, and that controls, the electronic device 12 of FIG. 1 is shown. The electronic circuit 250 is identical in much of its structure and operation to the electronic circuit 100 illustrated in FIG. 3 and described hereinabove. Like numbers are used in FIG. 6 to identify components in common with FIG. 3, and descriptions of these common components and functions will not be repeated here for brevity. The electronic circuit 250 differs from the electronic circuit 100 in that an independent clock circuit 254 is electrically connected between the UI processor 60 and a power control module 252 of the memory subsystem 54', which is provided, in this embodiment, in the form of a DPR processor. As with one embodiment of the electronic circuit 100, the Ready line in the electronic circuit 250 is electrically connected between the ME processor 62' and the power control module 252 of the DPR processor 54'.

In the embodiment illustrated in FIG. 6, reminder and automatic on times that are programmed into the clock circuit 63 of the ASIC are also programmed into the clock circuit 254. Programming of the reminder and automatic on times in the clock circuit 254 occurs via the UI processor 60. Otherwise, the clock circuit 254 is an independently operating circuit. When the programmed reminder or automatic on times are triggered by the clock circuits 63 and 254, the corresponding trigger signal generated by the clock circuit 63 in the ASIC 64 is passed by the ME processor 62' only to the UI processor 60. The corresponding trigger signal generated by the clock circuit 254 is passed only the power control module 252 in the DPR processor 54', which turns on the Power Supply 56 as described hereinabove. When strip insert is detected, in contrast, the strip insert trigger signal generated by the ASIC 64 is passed via the ME processor 62' to the UI processor 60 and to the power control module 252 via the Ready line. The UI processor 60 and the power control module 252 act on the strip insert trigger signal as described hereinabove with respect to FIG. 3.

Figure 7:
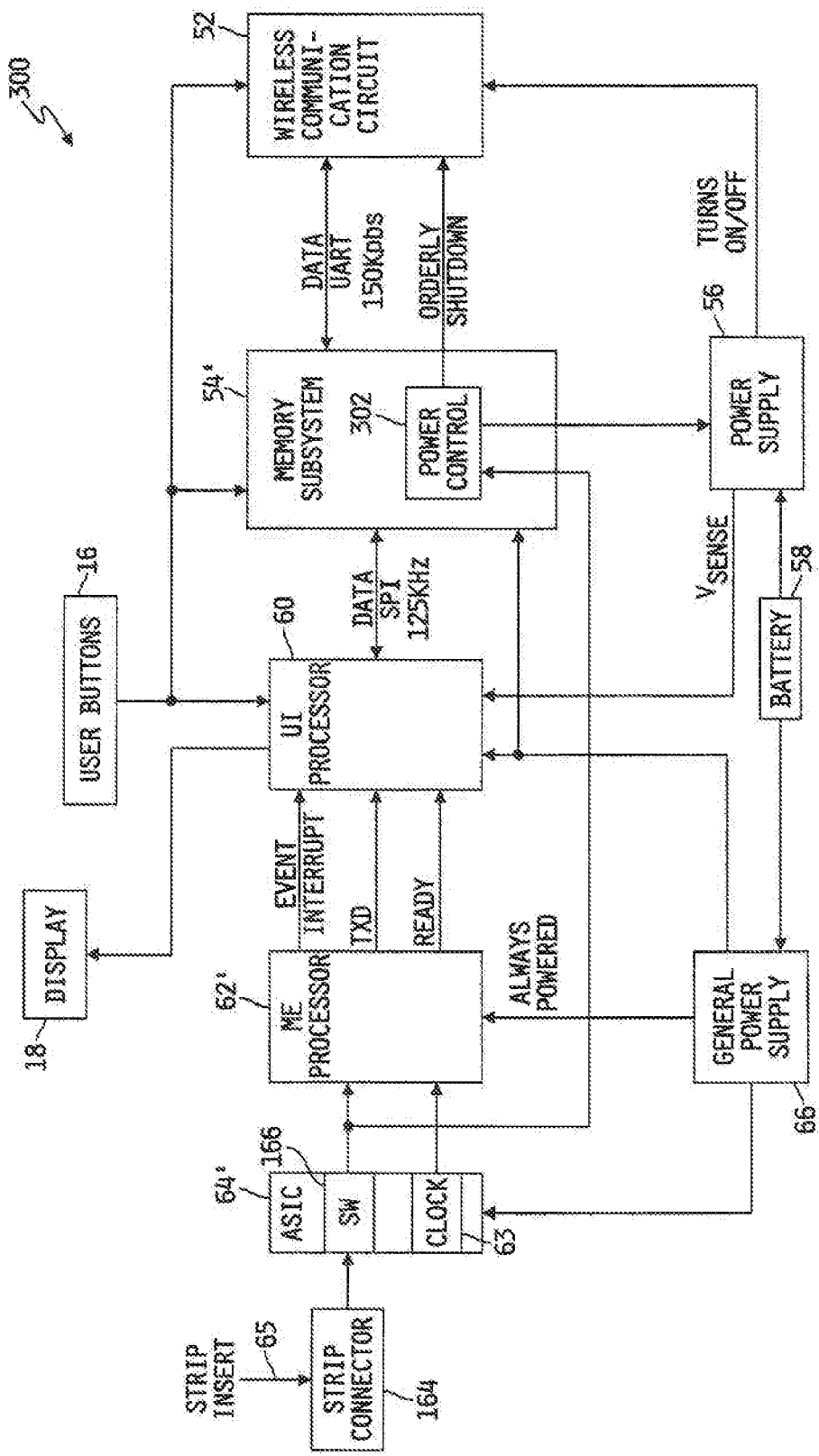
FIG. 7 shows a block diagram schematic of yet a further illustrative embodiment of an electronic circuit that is carried by, and that controls, one of the electronic devices of FIG. 1.

Referring now to FIG. 7, a block diagram schematic of another illustrative embodiment 300 of the electronic circuit that is carried by, and that controls, the electronic device 12 of FIG. 1 is shown. The electronic circuit 300 is identical in much of its structure and operation to the electronic circuit 100 illustrated in FIG. 3 and described hereinabove. Like numbers are used in FIG. 7 to identify components in common with FIG. 3, and descriptions of these common components and functions will not be repeated here for brevity. The electronic circuit 300 differs from the electronic circuit 100 in that the ASIC 64', including the electronic switch 166, and the strip connector 164 of FIGS. 4 and 5 are included in the electronic circuit 300. The signal line connected between the electronic switch 166 and the ME processor 62' is, in this embodiment, electrically connected to a power control module 302 of the memory subsystem 54', which is again provided in the form of a DPR processor. As with one embodiment of the electronic circuit 100, the Ready line in the electronic circuit 250 between the ME processor 62' and the power control module 302 of the DPR processor 54' is omitted.

When strip insert is detected, the electronic switch 166 in the ASIC changes produces a first signal that is passed by the electronic switch 166 to the ME processor 62', which notifies the UI processor 60' of this strip insert event via the Event interrupt, TX and/or Ready line. The first signal produced by the electronic switch 166 when insertion of a test element 22 into the test element receiving port 20 of the electronic device 12 is detected is also passed to the power control module 302 of the DPR processor 54', which then deactivates, i.e., turns off, the Power Supply 56. When the analyte measurement test is complete and the user removes the test element 22 from the test element receiving port 20, the electronic switch 166 changes state and produces a second signal that is indicative of detection of removal of the test element 22 from the test element receiving port 20. The power control module 302 of the DPR processor 54' is responsive to the change in the state of the switch 166 and production of the switch 166 of the second signal to reactivate, i.e., turn on, the Power Supply 56 if the Power Supply 56 is has not already been reactivated via another mechanism, e.g., by user press of one or a combination of the user buttons 16.

Figure 8:
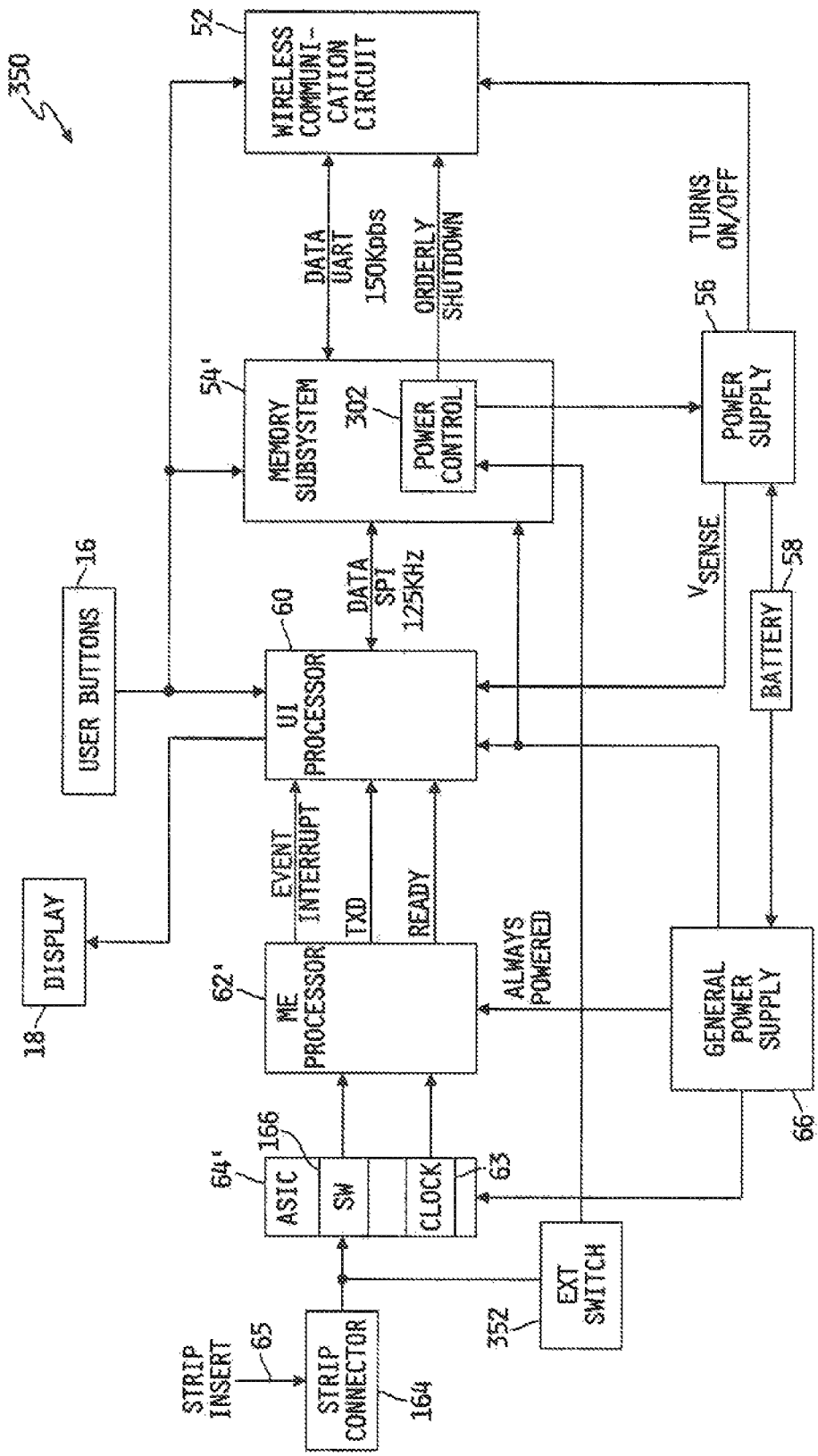
FIG. 8 shows a block diagram schematic of still a further illustrative embodiment of an electronic circuit that is carried by, and that controls, one of the electronic devices of FIG. 1.

Referring now to FIG. 8, a block diagram schematic of another illustrative embodiment 350 of the electronic circuit that is carried by, and that controls, the electronic device 12 of FIG. 1 is shown. The electronic circuit 350 is identical in most of its structure and operation to the electronic circuit 300 illustrated in FIG. 7 and described hereinabove. Like numbers are used in FIG. 8 to identify components in common with FIG. 7, and descriptions of these common components and functions will not be repeated here for brevity. The electronic circuit 350 differs from the electronic circuit 300 in that the signal line connected between the strip connector 164 and the electronic switch 166 of the ASIC 64' is, in this embodiment, also electrically connected to one terminal of an electrical, mechanical or optical switch 352 that is external to the ASIC 64' and to all other circuits forming the electronic circuit 350. Another terminal of the switch 352 is connected to the power control circuit 302 of the memory subsystem 54' which is yet again illustratively provided in the form of a DPR processor.

When strip insert is detected, the state of the switch 352 changes from a first state to a second state, and the second state causes the power control module 302 of the DPR processor 54' to deactivate, i.e., turn off, the Power Supply 56. When the analyte measurement test is complete and the user removes the test element 22 from the test element receiving port 20, the state of the switch 352 changes back to the first state. The power control module 302 of the DPR processor 54' is responsive to the first state of the switch 352 to reactivate, i.e., turn on, the Power Supply 56 if the Power Supply 56 has not already been reactivated via another mechanism, e.g., by user press of one or a combination of the user buttons 16.

Figure 9:
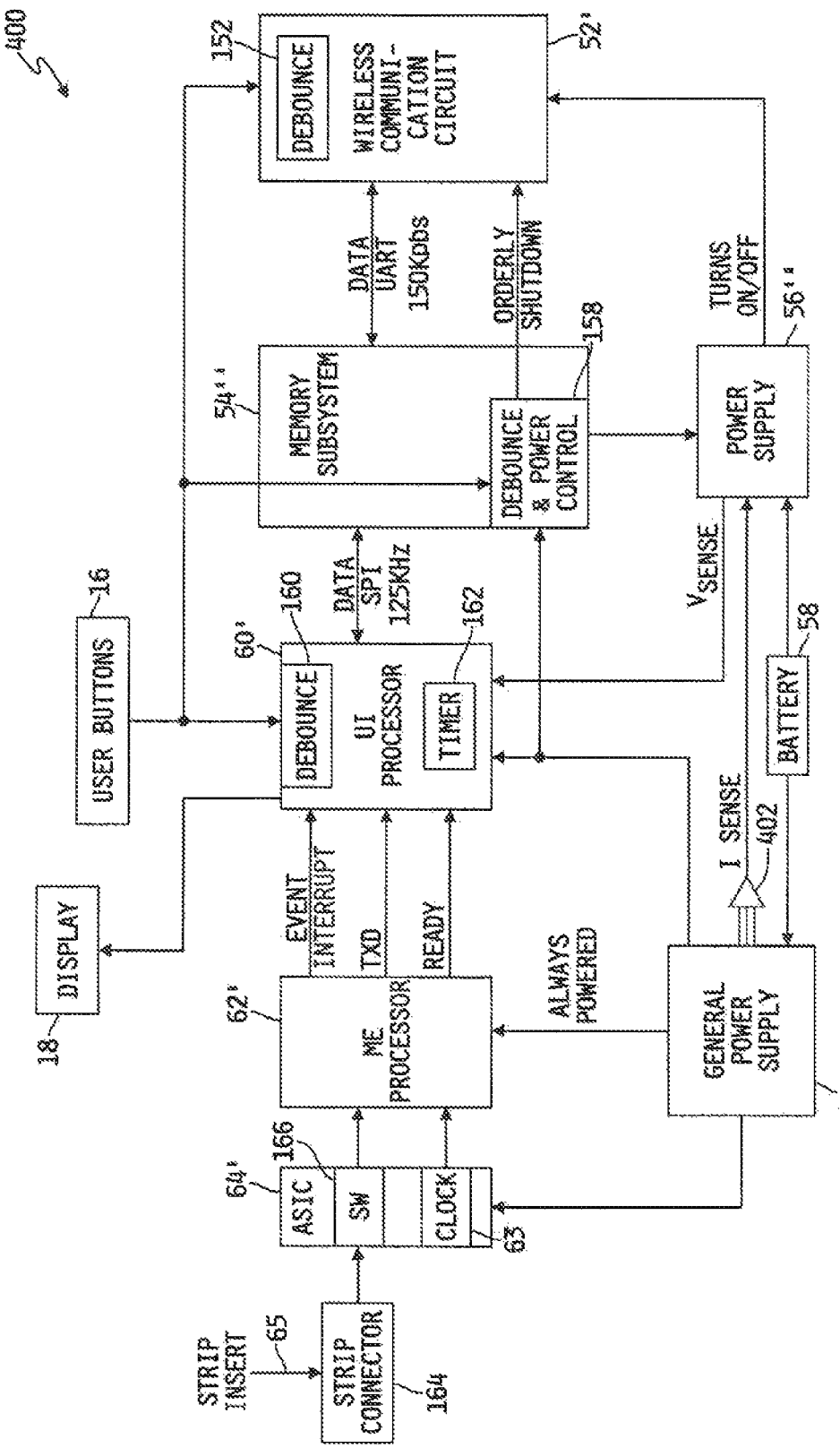
FIG. 9 is a block diagram schematic of yet another illustrative embodiment of an electronic circuit that is carried by, and that controls, one of the electronic devices of FIG. 1.

Referring now to FIG. 9, a block diagram schematic of another illustrative embodiment 400 of the electronic circuit that is carried by, and that controls, the electronic device 12 of FIG. 1 is shown. The electronic circuit 400 is identical in much of its structure and operation to the electronic circuit 150 illustrated in FIG. 4 and described hereinabove. Like numbers are used in FIG. 9 to identify components in common with FIG. 4, and descriptions of these common components and functions will not be repeated here for brevity. The electronic circuit 400 differs from the electronic circuit 150 in that a current sensing circuit 402 has at least one input that is electrically connected to the General Power Supply 66' and an output that is electrically connected to the Power Supply 56". The current sensing circuit 402 is configured to detect the supply current produced by the general power supply 66' and drawn by each of the ASIC 64', the ME processor 62' and the UI processor 60', and to supply a control signal having a first state and a second state based on the magnitude of the supply current produced by the General Power Supply 66' to the Power Supply 56". The first state of the control signal produced by the current sensing circuit 402 disables the Power Supply 56" such that the Power Supply 56" does not produce the supply voltage for the wireless communication circuit 52, and the second state of the control signal produced by the current sensing circuit 402 enables the Power Supply 56" such that the Power Supply 56" produces the supply voltage for the wireless communication circuit 52.

Generally, the current sensing circuit 402 is operable to enable and disable the Power Supply 56" based on the magnitude of the supply current produced by the General Power Supply 66'. For example, when the UI processor 60' turns on, i.e., is fully activated for operation, pursuant to power up of the device 12 for example, the magnitude of the supply current produced by the General Power Supply 66' is greater than when the UI processor 60' is not fully activated. This condition causes the current sensing circuit 402 to force the control signal to the second state which, in turn, causes the Power Supply 56" to turn on. The UI processor 60' is configured to periodically reset the timer circuit 162 as long as the UI processor 60' is actively operating, i.e., executing instructions and/or controlling some aspect of the electronic device 12. As long as the UI processor 60' continues to reset the timer circuit 162 before a predefined time period elapses since last resetting the timer circuit 162, the UI processor 60' is considered to be actively operating. The timer circuit 162 is programmed to produce a trigger signal if the UI processor 60' is inactive or idle, i.e., not executing instructions and/or actively controlling some aspect of the electronic device 12 for longer than the predefined time period since last resetting the timer circuit 162, e.g., 2 minutes. In this case, the UI processor 60' is configured to be responsive to the trigger signal produced by the timer circuit 162 to transition from the actively operating state to a low power sleep state in which the magnitude of the supply current produced by the General Power Supply 66' is less that when the UI processor 60' is actively operating. This condition causes the current sensing circuit 402 to force the control signal to the first state which, in turn, causes the Power Supply 56" to turn off.

The ME processor 62' and the ASIC 64' are each normally in a low power sleep state, and each transitions from the low power sleep mode to an actively operating state, i.e., a full-power operational state, when a test element 22 is detected as being inserted into the test element receiving port 20 and also upon detection of an automatic on or reminder event by the clock circuit 63 of the ASIC 64'. When the ME processor 62' and the ASIC 64' are each in the low power sleep state, the magnitude of the supply current produced by the General Power Supply 66' is less than when the ME processor 62' and the ASIC 64' are actively operating. This condition causes the current sensing circuit 402 to force the control signal to the second state which, in turn, causes the Power Supply 56" to turn on. Under normal conditions, i.e., when a test element 22 is not detected as being inserted into the test element receiving port 20 and when no automatic on or reminder events are produced by the clock circuit 63 of the ASIC 64' such that the ASIC 64' and the ME processor 62' are in the low power sleep states, the Power Supply 56" is therefore on and providing its supply voltage to the wireless communication circuit 52'.

When the ASIC 64' detects insertion of a test element 22 into the test element receiving port 20, the ASIC 64' transitions from its low power sleep state to its full power actively operating state where it then produces a strip insertion signal that is provided to the ME processor 62'. The strip insertion signal provided to the ME processor 62' causes the ME processor 62' to transition from its low power sleep state to its full power actively operating state to service the test element by analyzing the liquid sample provided on the test element 22 to determine the concentration of the analyte present in the liquid sample. When the ASIC 64' and the ME processor 62' transition from their low power sleep states to their full power actively operating states, the magnitude of the supply current produced by the General Power Supply 66' becomes greater than when the ME processor 62' and the ASIC 64' are in their low power sleep states. This condition causes the current sensing circuit 402 to force the control signal to the first state which, in turn, causes the Power Supply 56" to turn off. After the ME processor 62' determines the concentration of the analyte in the liquid sample provided on the test sample 22, the ME processor 62' and the ASIC 64' each transition from their full power actively operating states back to their low power sleep states. This condition causes the current sensing circuit 402 to force the control signal back to the second state which, in turn, causes the Power Supply 56" to turn back on.

The clock circuit 63 of the ASIC 64' is configured to produce a trigger signal upon occurrence of a programmed automatic on time or reminder, and the ASIC 64' is configured to be responsive to the trigger signal to transition from its low power sleep state to its full power actively operating state where it then passes the trigger signal to the ME processor 62'. This causes the ME processor 62' to transition from its low power sleep state to its full power actively operating state, and to then pass the trigger signal to the UI processor 60'. When the ASIC 64' and the ME processor 62' transition from their low power sleep states to their full power actively operating states in response to the automatic on or reminder signal produced by the clock circuit 63, the magnitude of the supply current produced by the General Power Supply 66' becomes greater than when the ME processor 62' and the ASIC 64' are in their low power sleep states. This condition causes the current sensing circuit 402 to force the control signal to the first state which, in turn, causes the Power Supply 56" to turn off.

Figure 10:
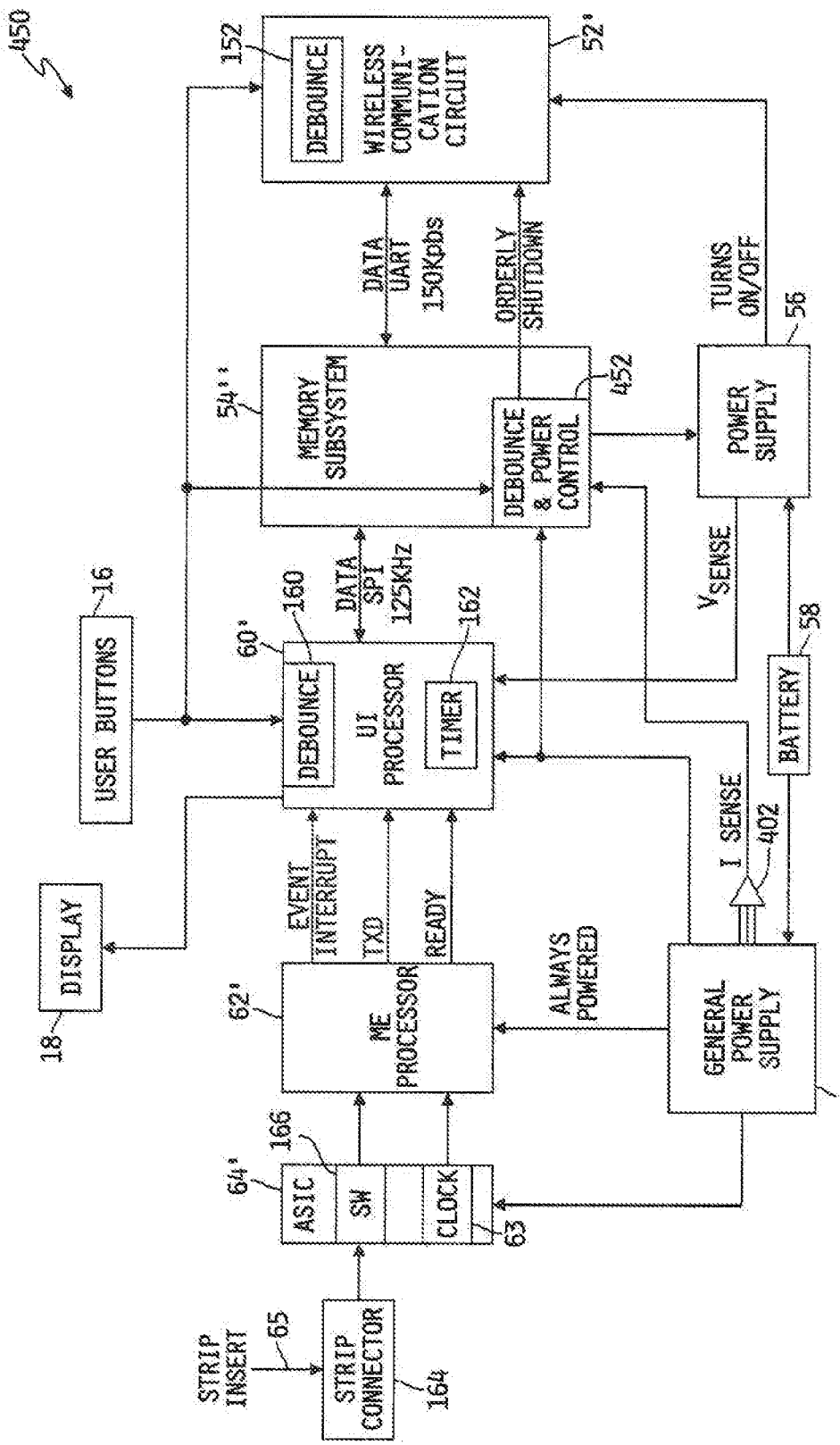
FIG. 10 is a block diagram schematic of still another illustrative embodiment of an electronic circuit that is carried by, and that controls, one of the electronic devices of FIG. 1.

Referring now to FIG. 10, a block diagram schematic of another illustrative embodiment 450 of the electronic circuit that is carried by, and that controls, the electronic device 12 of FIG. 1 is shown. The electronic circuit 450 is identical in much of its structure and operation to the electronic circuit 400 illustrated in FIG. 9 and described hereinabove. Like numbers are used in FIG. 10 to identify components in common with FIG. 9, and descriptions of these common components and functions will not be repeated here for brevity. The electronic circuit 450 differs from the electronic circuit 400 in that a current sensing circuit 402 is electrically connected between the General Power Supply 66' and the debounce and power control module 452 of the memory subsystem 54", which is yet again provided in the form of a DPR processor (rather than between the General Power Supply 66' and the Power Supply 56). The current sensing circuit 402 detects the supply current drawn by each of the ASIC 64', the ME processor 62' and the UI processor 60' as before, and supplies a first control signal to the debounce and power control module 452 of the DPR processor 54". The debounce and power control module 452 is responsive to the first control signal to produce a second control signal that causes the Power Supply 56" to turn on and off based on the supply currents drawn by ASIC 64', ME processor 62' and the UI processor 60', in keeping with the example of FIG. 9, when the first control signal is forced by the current sensing circuit 402 to a first state, the debounce and power control module 452 likewise forces the second control signal to a first state, which causes the Power Supply 56" to turn off, and when the control circuit 402 forces the first control signal to a second, opposite state, the debounce power control module 452 likewise forces the second control signal to a second, opposite state, which causes the Power Supply 56" to turn on. In the electronic circuit 450 of FIG. 10, the Power Supply 56 is turned on and off in response to the power states of the ASIC 64', the ME processor 62' and the UI processor 60', in response to detection of a strip insert event, in response to an automatic on or reminder event and in response to an automatic off event, identically as described with respect to FIG. 9, except that the debounce and power control module 452 has direct control over the Power Supply 56 rather than the current sensing circuit 452 having direct control over the Power Supply 56 as just described.

Figure 11:
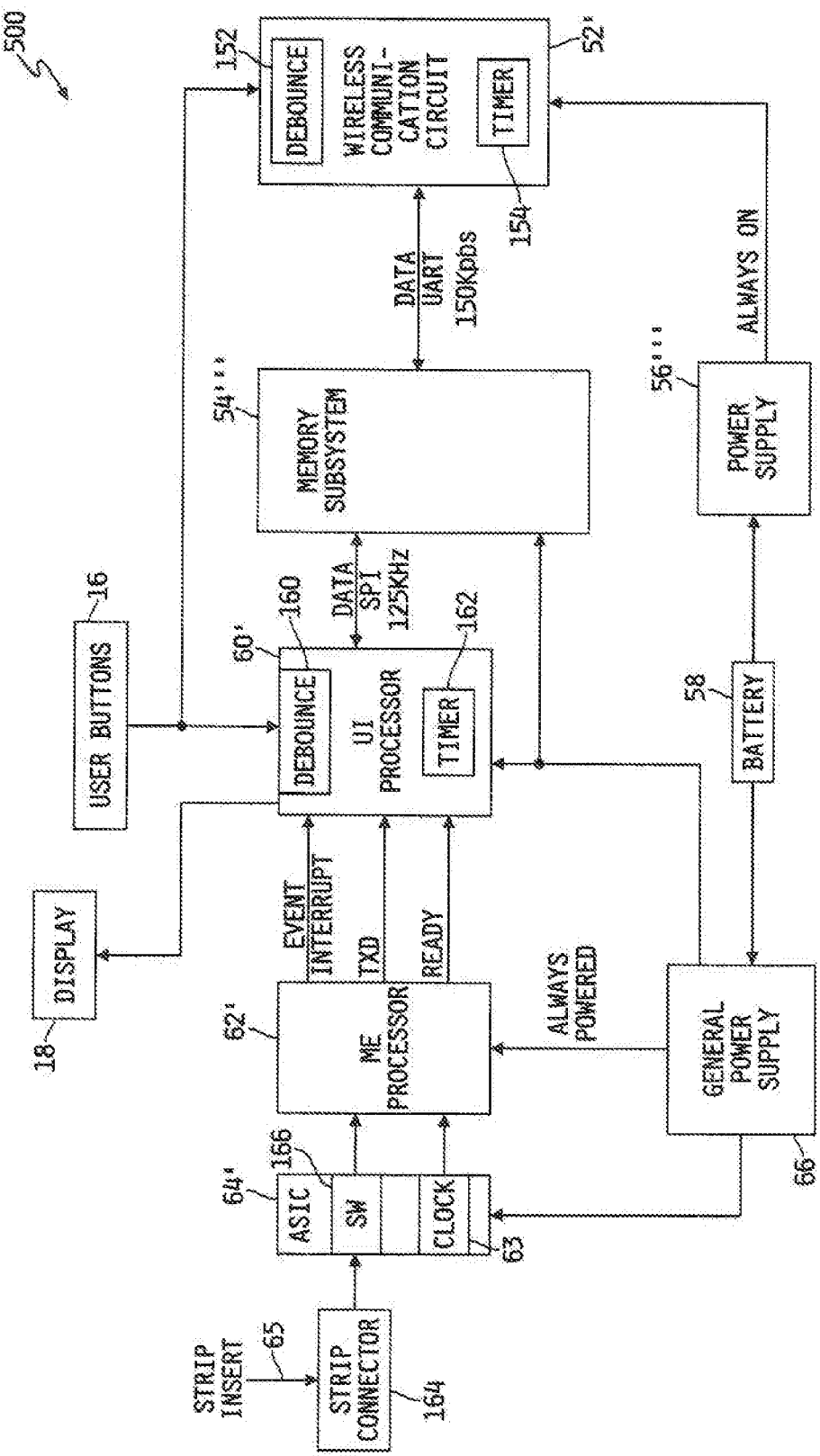
FIG. 11 is a block diagram schematic of yet a further illustrative embodiment of an electronic circuit that is carried by, and that controls, one of the electronic devices of FIG. 1.

Referring now to FIG. 11, a block diagram schematic of another illustrative embodiment 500 of the electronic circuit that is carried by, and that controls, the electronic device 12 of FIG. 1 is shown. The electronic circuit 500 is identical in much of its structure and operation to the electronic circuits 150 and 200 illustrated in FIGS. 4 and 5 and described hereinabove. Like numbers are used in FIG. 11 to identify components in common with FIGS. 4 and 5, and descriptions of these common components and functions will not be repeated here for brevity. The electronic circuit 500 differs from the electronic circuits 150 and 200 in that the memory subsystem 54''' does not include a power control module and is not electrically connected to the Power Supply 56''' The Power Supply 56''' is, in this embodiment, always turned on at full power and, as in one embodiment of the electronic circuit 200, the $V_{SENSE}$ line between the Power Supply 56''' and the UI processor 60' is omitted. The memory subsystem 54''' also does not include a debounce circuit, and is not electrically connected to any of the user buttons 16. In the electronic circuit 500, the memory subsystem 54''' does not control any other circuit, and acts only as a repository for information moving between the UI processor 60' and the electronic device 14. In this embodiment, the memory subsystem 54''' is illustratively provided in the form of a DPR processor, but may alternatively be provided in the form of a conventional memory unit.

When a wireless connection is established between the devices 12 and 14, the UI processor 60' is operable, as long as this connection is to be maintained, to periodically store query data in the outbound data buffer 57 of the memory subsystem 54'''. The query data is then sent to the device 14, and return "acknowledgement" signals are sent back by the device 14 to the device 12 to maintain the wireless connection, all as described above with respect to the operation of the electronic circuit 150 of FIG. 4. In the electronic circuit 500, the UI processor 60' always has knowledge of the desired state of operation of the electronic circuit 500 from various predefined or programmed ones or combinations of user presses of the user buttons 16. Accordingly, the UT processor 60' always has knowledge of when a wireless connection should and should not be established between the electronic devices 12 and 14.

The wireless communication circuit 52' in the electronic circuit 500 is always powered by the Power Supply 56''', and the wireless communication circuit 52' is responsive to a number of different events to transition itself into, and out of, any of a plurality of different low power states as described above with respect to the electronic circuit 200 of FIG. 5. For example, when in a fully powered "awake" state with a wireless connection established between the electronic devices 12 and 14, the wireless communication circuit 52' is operable to periodically, e.g., every 100-200 milliseconds, check the outbound data buffer 57 of the memory subsystem 54''' as described above. Each time the wireless communication circuit 52' finds data in the outbound data buffer 57 of the memory subsystem 54''', the wireless communication circuit 52' resets the timer circuit 154, packs the data according to the predetermined wireless communication protocol, and wirelessly transmits a corresponding signal to the device 14.

When a wireless connection is established between the electronic devices 12 and 14, and the UI processor 60' determines that the wireless connection should be terminated, the UI processor 60' stores connection termination data in the outbound data buffer 57 of the memory subsystem 54'''. When the wireless communication circuit 52' thereafter finds data in the outbound data buffer 57 of the memory subsystem 52', asynchronously with respect to the operation of the UI processor 60', the wireless communication circuit 52' incorporates the data into to the predetermined wireless communication protocol and transmits a corresponding via its wireless communication circuitry, e.g., RF transmission circuitry, to the electronic device 14. The electronic device 14 then wirelessly sends a signal containing a predefined connection termination response back to the device 12. Subsequently, the processor of the medical device 14 instructs the wireless communication module 30 to orderly terminate communications or connections with the wireless communications circuit 52' that may be specific to the predetermined wireless protocol. When the wireless connection is terminated in this manner, the wireless communication circuit 52' is operable to check the outbound data buffer 57 of the memory subsystem 54'''. If no data resides in the outbound data buffer 57 of the memory subsystem 54''', the wireless communication circuit 52' successively enters lower power sleep states or modes as described above. If, however, the wireless communication circuit 52' finds data in the outbound data buffer 57 of the memory subsystem 54''', the wireless communication circuit 52' attempts to establish a wireless connection with the wireless communication module 30 of the electronic device 14 in a manner that is consistent with the predetermined wireless communication protocol. If, after a predefined or programmed number of attempts and/or elapsed time, no wireless connection can be established, the wireless communication circuit 52' clears the outbound data buffer 57 of the memory subsystem 54'''. Alternatively, the UI processor 60' may clear the outbound data buffer 57 of the memory subsystem 54''' if it determines that data exists in the outbound data buffer 57 of the memory subsystem 54''' after some time period has elapsed since storing the wireless communication message in the outbound data buffer 57 of the memory subsystem 54''' or after some time period has elapsed after determining, based on failure to receive acknowledgement signals from the device 14, that a wireless connection between the devices 12 and 14 no longer exists. In any case, with the outbound data buffer 57 of the memory subsystem 54''' empty, the wireless communication circuit 52' successively enters lower power sleep states or modes as described above.

When the wireless connection is terminated in this manner, the wireless communication circuit 52' is operable to check the outbound data buffer 57 of the memory subsystem 54'''. If no data resides in the outbound data buffer 57 of the memory subsystem. 54''', the wireless communication circuit 52' successively enters lower power sleep states or modes as described above. If, however, the wireless communication circuit 52' finds data in the outbound data buffer 57 of the memory subsystem 54''', the wireless communication circuit 52' attempts to establish a wireless connection with the wireless communication module 30 of the electronic device 14 as described hereinabove. If, after a predefined or programmed number of attempts and/or elapsed time, no wireless connection can be established, the wireless communication circuit 52' clears the outbound data buffer 57 of the memory subsystem 54'''. Alternatively, the UI processor 60' may clear the outbound data buffer 57 of the memory subsystem, 54''' if it determines that data exists in the outbound data buffer 57 of the memory subsystem. 54''' after some time period has elapsed since storing the data in the outbound data buffer 57 of the memory subsystem 54''' or after some time period has elapsed after determining, based on failure to receive acknowledgement signals from the device 14, that a wireless connection between the devices 12 and 14 no longer exists. In any case, with the outbound data buffer 57 of the memory subsystem 54''' empty, the wireless communication circuit 52' successively enters lower power sleep states or modes as described above.

In the event of a lost wireless connection between the devices 12 and 14, the wireless communication circuit 52' is operable to turn off its wireless transmission circuitry and to transition to a first low power state if it fails to find data in the outbound data buffer 57 of the memory subsystem 54" when the timer circuit 154 reaches a first timer value. Because the wireless connection is lost, the UI processor 60' will no longer receive acknowledgement signals from the electronic device 14 and will therefore cease to store data in the outbound data buffer 57 of the memory subsystem 54'''. However, data may reside within the outbound data buffer 57 of the memory subsystem 54''' when the wireless connection is lost. In this case, after a predefined or programmed number of attempts and/or after a predefined or programmed elapsed time, no wireless connection can be established with the device 14, the wireless communication circuit 52' clears the outbound data buffer 57 of the memory subsystem 54'''. Alternatively, the UI processor 60' may clear the outbound data buffer 57 of the memory subsystem 54''' if it determines that data exists in the outbound data buffer 57 of the memory subsystem 54''' after some time period has elapsed since storing the last data in the outbound data buffer 57 of the memory subsystem 54''' or after some time period has elapsed after determining, based on failure to receive acknowledgement signals from the device 14, that a wireless connection between the devices 12 and 14 no longer exists. In any case, with the outbound data buffer 57 of the memory subsystem 54''' empty, the wireless communication circuit 52' successively enters lower power sleep states or modes as described above.

When in the lowest power "deep sleep" state, the wireless communication circuit 52' periodically, e.g., every 400 milliseconds, wakes up to a "UART only" state, in which the wireless communication circuit 52' has sufficient power to check the outbound data buffer 57 of the memory subsystem 54''' via the data UART line. If the outbound data buffer 57 of the memory subsystem 54''' has data stored therein, such as when the UI processor 60' detects user button press of an On button or buttons or when the UI processor 60' detects, via the ASIC 64' and ME processor 62' a reminder On or automatic On, the wireless communication circuit 52' wakes up to a full power state, turns on its wireless communication circuitry and attempts to cooperatively establish a wireless connection with the wireless communication module 30 of the electronic device 14 as described above. If, on the other hand, the outbound data buffer 57 of the memory subsystem 54''' has no data stored therein, the wireless communication circuit 52' transitions back to the lowest power "deep sleep" state as described above.

Unless the electronic devices 12 and 14 are communicating information, the wireless communication circuit 52' in the electronic circuitry 500 is generally in one of the lower power sleep states or modes. When strip insert is detected, the electronic device 12 performs an analyte determination test as described above. The electronic device 12 does not wirelessly communicate with the electronic device 14 during the analyte determination test, and the wireless communication circuit 52' is either in one of the lower power sleep states or modes when the strip insert is detected, or it enters successively lower power sleep states shortly after strip insert is detected because the UI processor 60' stores a connection termination message in the outbound data buffer 57 of the memory subsystem 54''' when strip insert is detected, or because the UI processor 60' stops storing data in the outbound data buffer 57 of the memory subsystem 54''' when strip insert is detected.

Figure 12:
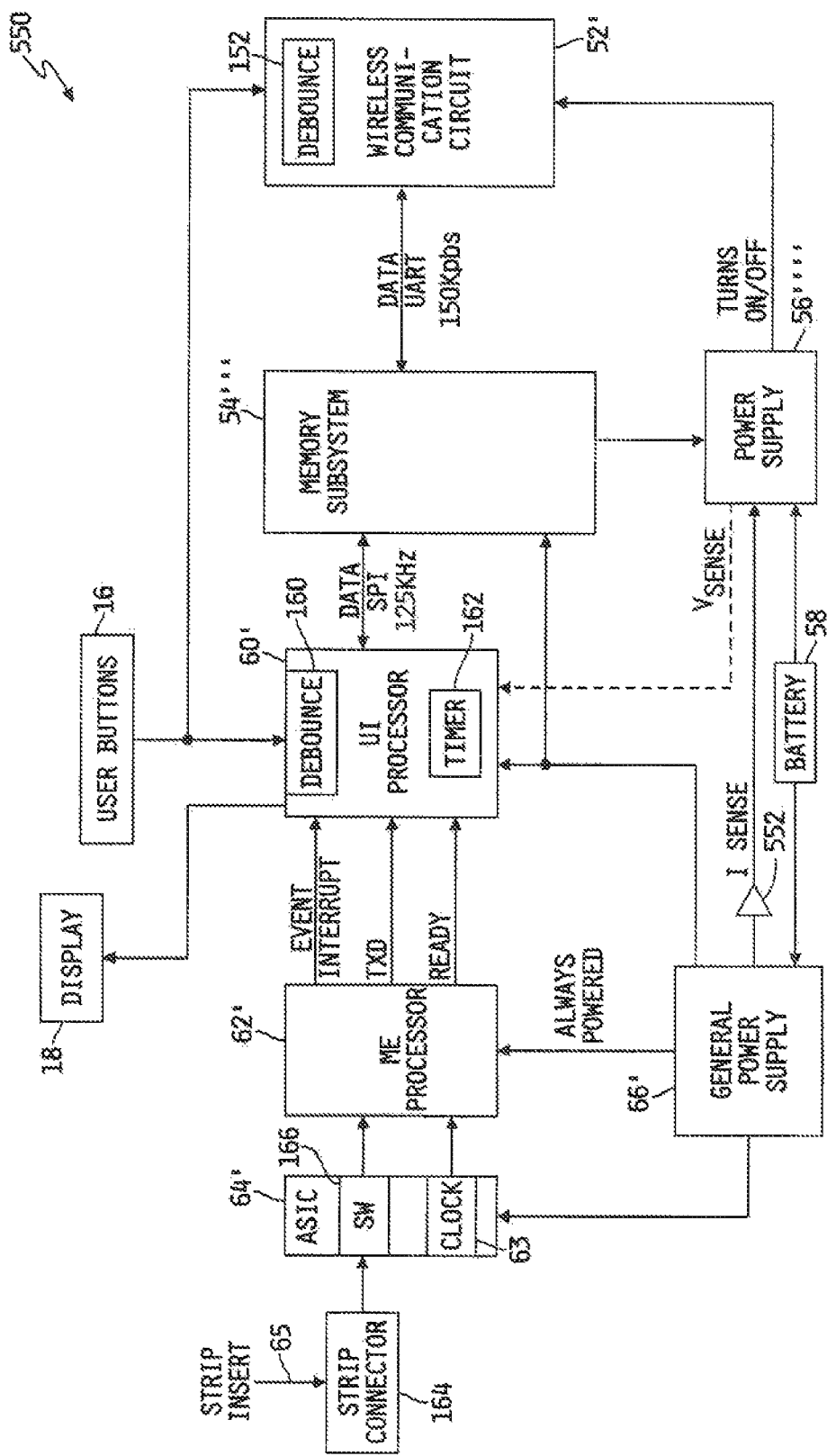
FIG. 12 is a block diagram schematic of still a further illustrative embodiment of an electronic circuit that is carried by, and that controls, one of the electronic devices of FIG. 1.

Referring now to FIG. 12, a block diagram schematic of another illustrative embodiment 550 of the electronic circuit that is carried by, and that controls, the electronic device 12 of FIG. 1 is shown. The electronic circuit 550 is identical in much of its structure and operation to the electronic circuit 500 illustrated in FIG. 11 and described hereinabove. Like numbers are used in FIG. 12 to identify components in common with FIG. 11, and descriptions of these common components and functions will not be repeated here for brevity. The electronic circuit 550 differs from the electronic circuit 500 in that a current sensing circuit 552 is connected between the General Power Supply 66' and the Power Supply 56''''. The $V_{SENSE}$ line may or may not be connected between the Power Supply 56'''' and the UI processor 60', as shown in phantom in FIG. 12.

In the embodiment illustrated in FIG. 12, the current sensing circuit 552 is configured to produce a control signal having a first state if the supply current being drawn from the General Power Supply 66' by all of the remaining circuitry of the electronic circuit 550 is above a first current threshold, and having a second, opposite state if the supply current being drawn from the General Power Supply 66' by all of the remaining circuitry of the electronic circuit 550 drops below a second current threshold. Generally, the first current threshold will be set at a higher current value than the second current threshold to provide for switching hysteresis, although other embodiments are contemplated in which the first and second current thresholds are equal or in which the second current threshold is set at a higher current value than the first current threshold. In one embodiment, the Power Supply 56"" is responsive to a transition of the control signal from the first state to the second state to turn itself off pursuant to a manual or automatic power down event. Likewise, the Power Supply 56"" may be responsive to a transition of the control signal from the second state to the first state to turn itself on pursuant to a manual or automatic power up event.

Figure 13:
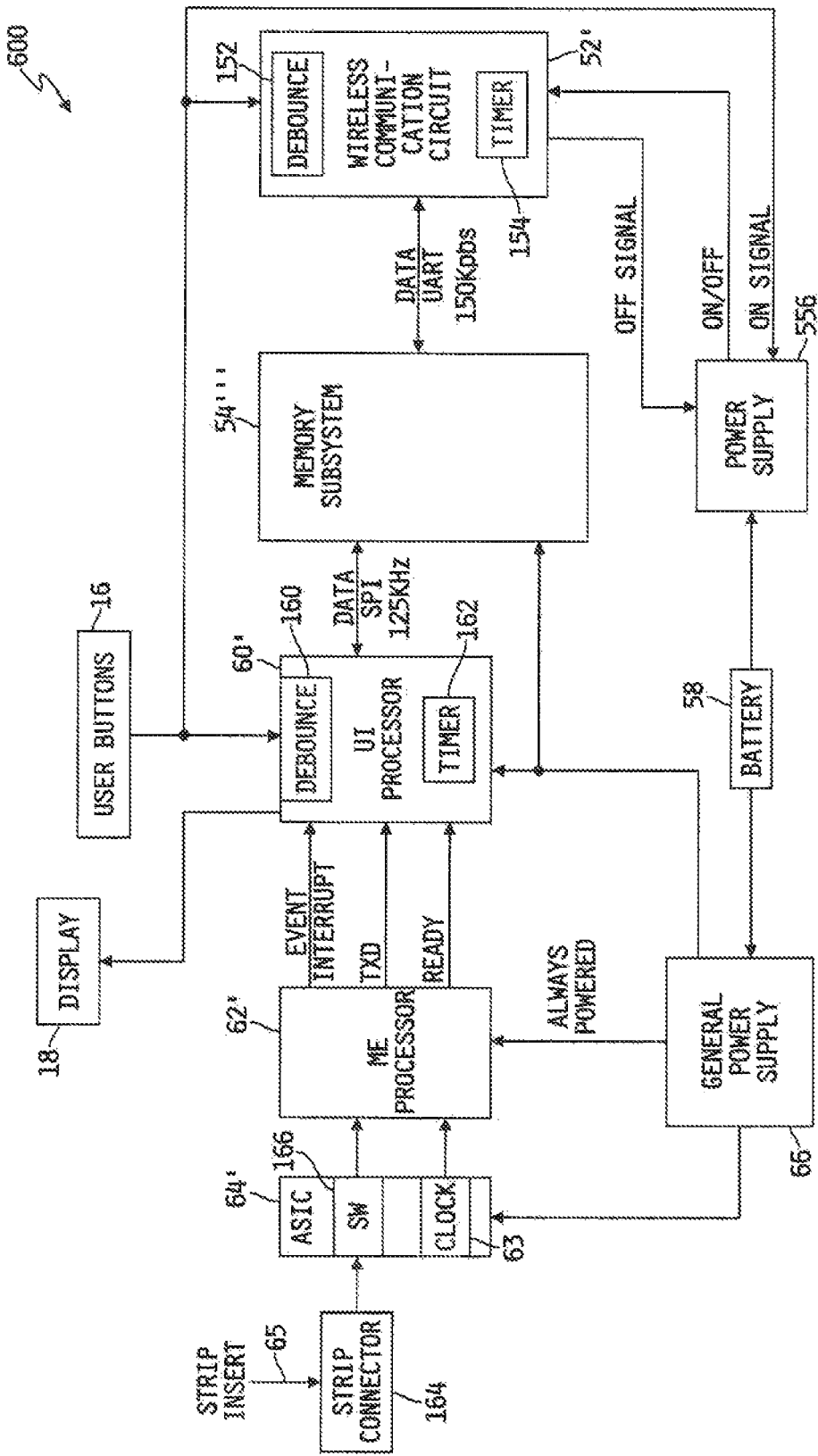
FIG. 13 is a block diagram schematic of still another illustrative embodiment of an electronic circuit that is carried by, and that controls, one of the electronic devices of FIG. 1.

Referring now to FIG. 13, a block diagram schematic of another illustrative embodiment 600 of the electronic circuit that is carried by, and that controls, the electronic device 12 of FIG. 1 is shown. The electronic circuit 600 is identical in much of its structure and operation to the electronic circuit 500 illustrated in FIG. 11 and described hereinabove. Like numbers are used in FIG. 13 to identify components in common with FIG. 11, and descriptions of these common components and functions will not be repeated here for brevity. The electronic circuit 600 differs from the electronic circuit 500 in that the power supply 56''' of FIG. 11 is replaced with a power supply 556 that is electrically connected to the user buttons 16. The power supply 556 is also configured to receive a control signal from the wireless communication circuit 52'.

In the embodiment illustrated in FIG. 13, the power supply 556 may be completely powered down, i.e., turned off, from any state via a simultaneous or sequential user press of a number of the user buttons 16. The power supply 556 is configured to remain in the completely powered down state until the user again presses the simultaneous or sequential number of the user buttons 16 or a different simultaneous or sequential user press of a number of the user buttons. In the illustrated embodiment, the wireless communication circuit 52' may also completely power down, i.e., turn off the power supply 556 by supplying an appropriate control signal in the form of an "off" signal to the power supply 556. The power supply 556 is configured, in this embodiment, to be responsive to such a control signal to completely power down, i.e., turn off. Generally, the wireless communication circuit 52' is configured to be responsive to successively greater time out values of the timer 154 to enter successively lower power, e.g., lower power usage, states as described above. In one illustrative embodiment of the electronic circuit 600, the wireless communication circuit 52' is configured to produce the "off" control signal when the timer 154 reaches a predefined time out value that is greater than the time out value for which the wireless communication circuit 52' enters its lowest power "sleep" state. In this embodiment, the wireless communication circuit 52' thus turns off the power supply 556 after a predefined time duration of inactivity, wherein the predefined time duration is generally longer than that required to cause the wireless communication circuit 52' to enter into its lowest power "sleep" state.

Figure 14:
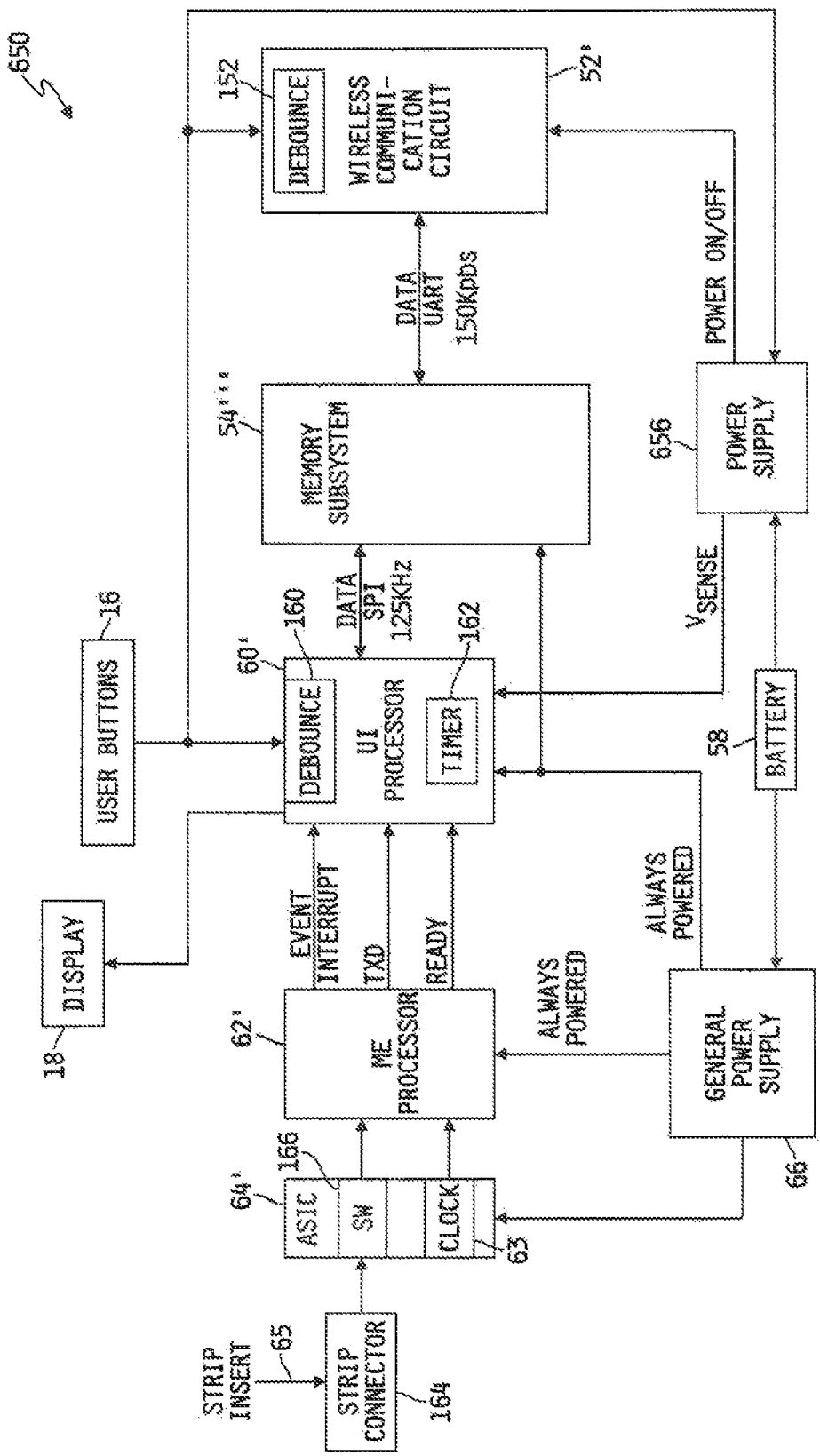
FIG. 14 is a block diagram schematic of yet a further illustrative embodiment of an electronic circuit that is carried by, and that controls, one of the electronic devices of FIG. 1.

Referring now to FIG. 14, a block diagram schematic of another illustrative embodiment 650 of the electronic circuit that is carried by, and that controls, the electronic device 12 of FIG. 1 is shown. The electronic circuit 600 is identical in much of its structure and operation to the electronic circuit 500 illustrated in FIG. 11 and described hereinabove. Like numbers are used in FIG. 14 to identify components in common with FIG. 11, and descriptions of these common components and functions will not be repeated here for brevity. The electronic circuit 650 differs from the electronic circuit 500 in that the power supply 56''' of FIG. 1 is replaced with a power supply 656 that is electrically connected to the user buttons 16. The power supply 556 is also electrically connected to the UI processor 60' via the $V_{SENSE}$ line as described above.

In the embodiment illustrated in FIG. 14, the power supply 656 may be completely powered down, i.e., turned off, from any state via a simultaneous or sequential user press of a number of the user buttons 16. The power supply 656 is configured to remain in the completely powered down state until the user presses any of the user buttons 16, in which case the power supply 656 transitions from its off state to its lowest power deep sleep state. The UI processor 60' is configured, as described in previous embodiments above, to control the state of a power supply on/off indicator on the display via monitoring the state of the power supply 656 via the $V_{SENSE}$ line.

Figure 15:
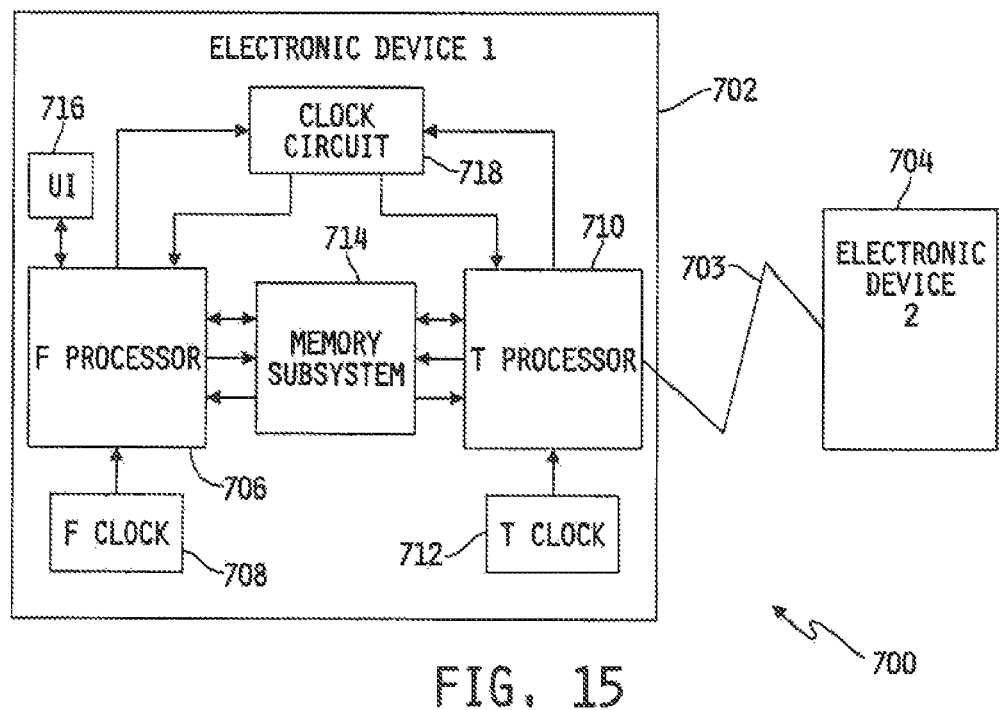
FIG. 15 is a diagram of another illustrative embodiment of a wireless communication system that is configured for wireless communications between two separate electronic devices.

Referring now to FIG. 15, another illustrative embodiment of a wireless communication system 700 is shown that is configured for wireless communications between two separate electronic devices 702 and 704. In one illustrative embodiment, the electronic device 702 is a medical device and the electronic device 704 is a remote electronic device. In this embodiment, the medical device 702 may be, for example, an ambulatory medical device, although the medical device 702 may alternatively be or include a non-ambulatory medical device. Examples of any such ambulatory medical devices illustrated herein may include, but should not be limited to, one or any combination of a medication or drug delivery device such as an infusion pump, a glucose meter, a body fluid analyte sensor system including one or more subcutaneous and/or implanted body fluid analyte sensors, a remote terminal representing a remote infusion pump display on which data from the infusion pump is displayed to a user, or the like. The remote electronic device 704, in this embodiment may be or include, but should not be limited to, a conventional personal data assistant (PDA) device, an application-specific remote electronic device that may be handheld, attachable or mountable to clothing, configured to be worn by a person such as on or about a limb or portion thereof on or about a head or portion thereof, or on or about a body or portion thereof, attachable to a key ring, or the like, a portable electronic communication device with an on-board glucose meter, a smart phone, a personal computer (PC), a laptop, notebook or similar computer, or the like. In one specific embodiment, which should not be considered to be limiting in any way, the electronic device 702 is an insulin infusion pump and the remote electronic device 704 is a hand-held smart phone. In other embodiments, the functionality of the electronic devices 702 and 704 may be reversed, i.e., the electronic device 704 may be a medical device, ambulatory or otherwise, and the electronic device 702 may be a remote electronic device. In one specific alternate embodiment, for example, the electronic device 702 is a remote, hand held electronic device that includes not only the components shown in FIG. 15 but also an on-board glucose meter and other components as illustrated and described herein, and the electronic device 704 is an insulin infusion pump. In any case, in still other embodiments, the electronic devices 702 and 704 may both be medical devices, ambulatory or otherwise, and in further embodiments the electronic devices 702 and 704 may both be non-medical electronic devices.

The electronic device 704 may or may not be configured identically to the electronic device 702, and in any case the electronic devices 702 and 704 are configured to communicate wirelessly with each other via a conventional wireless communication medium 703. Examples of the wireless communication medium 703 may include, but should not be limited to, radio frequency (RF), infrared (IR), microwave, inductive coupling, or the like. In one specific example, which should not be considered limiting in any way, the electronic devices 702 and 704 are each configured to communicate via RF according to a conventional BlueTooth® radio frequency communications protocol.

In the illustrated embodiment, the electronic device 702 includes a device function processor, F PROCESSOR, 706 that is configured to control all functional operations of the device 702 but not including telemetry operations, i.e., wireless communications with the electronic device 704. A clock circuit, F CLOCK, 708 is electrically connected to the device function processor 706, and the timing of operation of the device function processor 706 is controlled by the clock circuit 708. In one embodiment, the device function processor 706 includes two processors; a main processor that handles all of the device functionality of the electronic device 702, and a supervisor processor that continuously checks the main processor and activates an alarm if the main processor malfunctions. The main processor in this embodiment may be, for example, a model V850SA1, 32-bit microcontroller that is commercially available from NEC corporation, although the main processor may alternatively be implemented using other conventional microprocessor-based or non-microprocessor-based circuits. The supervisor processor in this embodiment may be, for example, a model PIC12C509, 8-bit microcontroller that is commercially available from Microchip Technology, Inc., although the supervisor processor may alternatively be implemented using other conventional microprocessor-based or non-microprocessor-based circuits, in some embodiments, such as in embodiments in which the electronic device 12 is not a medical device, the supervisor processor may be omitted. In some embodiments, such as in embodiments in which the electronic device 12 is a medical device, an additional processor may be added between the device function processor, F PROCESSOR, 706 and the memory subsystem 714. This additional processor may be, for example, a model MSP430F1611 16-bit microcontroller that is commercially available from Texas Instruments.

The electronic device 702 further includes a telemetry processor, T PROCESSOR, 710 that is configured to control wireless communication with the electronic device 704, but not device functions, i.e., non-telemetry operations of the electronic device 702. Another clock circuit. T CLOCK, 712 is electrically connected to the telemetry processor 710, and the timing of operation of the telemetry processor 710 is controlled by the clock circuit 712. In one embodiment, the telemetry processor 710 includes two separate processors; a main processor and a dedicated wireless communication processor. The main processor in this embodiment may be, for example, a model MSP430F2471 16-bit microcontroller that is commercially available from Texas Instruments, although the main processor may alternatively be implemented using other conventional microprocessor-based or non-microprocessor-based circuits. In one example of this embodiment in which the wireless communication protocol is a BlueTooth® RF communications protocol, the wireless communication processor may, for example, be a BlueCore 4-ROM Plug-N-Go, single chip radio and baseband circuit that is commercially available from a number of suppliers such as CSR. In this example embodiment, the wireless communication processor handles the BlueTooth® communications, i.e., the lower layer of the BlueTooth® protocol stack, and the main processor handles the upper layer of the BlueTooth® protocol stack and, in some embodiments, an additional security layer. In alternative embodiments, the main processor and the wireless communication processor may be substituted by a single processor, e.g., a single BlueCore 4-ROM Plug-N-Go, single chip radio and baseband circuit. In alternative embodiments, the wireless communication processor handles the Blue-Tooth® communications, i.e., the lower and upper layers of the BlueTooth® protocol stack. The main processor, in this embodiment, handles an additional security layer and communication layers with the memory subsystem 714.

The electronic device 702 further includes a memory subsystem 714 that is electrically connected to the device function processor 706 and also to the telemetry processor 710. The memory subsystem 714 acts as an independently operating storage buffer for information passing between the device function processor 706 and the telemetry processor 710 as will be described in greater detail hereinafter. In some embodiments, as illustrated in FIG. 15, the electronic device 702 further includes a clock circuit 718 that is electrically connected to the device function processor 706 and to the telemetry processor 710. The clock circuit 718 illustratively supplies at the request of the device function processor 706 and or of the telemetry processor 710 timing information used to synchronize information transfer between the device function processor 706 and the memory subsystem 714 and between the telemetry processor 710 and the memory subsystem 714 such that neither the device function processor 706 nor the telemetry processor 710 controls or regulates information transfer between the two processors 706, 710. In any case, control of the functions of the electronic device 702 and of the telemetry operations of the electronic device 702 are thus separate and independent of each other.

During communications between the device function processor 16 an the telemetry processor 18 as just described, the device function processor 16 and the telemetry processor 18 operate separately and independently of each other. The device function processor 16 controls only the functions and operations of the electronic device 12 that are not telemetry related, and the telemetry processor 18 controls only the telemetry operations. In embodiments of the system 700 that include the clock circuit 718 in the form of a real time clock, the device function processor 706 and the telemetry processor 710 both read data from and write data to the memory subsystem 714 according to predefined time slots and their own internal timing. In such embodiments, the device function processor 706 and the telemetry processor 710 each align their internal clocks and optionally their time bases with a time reference supplied by the real time clock 718 at predetermined times that are different from each other during each information packet transfer such that synchronization of the communication process is indirectly accomplished. In embodiments of the system 700 that include the clock circuit 718 in the form of a clock generator configured to produce information packet and data bit clock signals, the device function processor 706 and the telemetry processor 710 both read data from and write data to the memory subsystem 714 under the control of the clock circuit 718 and not under the control of any internal timing mechanism. In another embodiment, the system 700 includes the clock circuit 718 in the form of a clock generator configured to respond in the form of an alarm to a timing request of the device function processor 706 and the telemetry processor 710 over an interrupt signal. The interrupt signal is used in this case to start the communication process between the processors 706 and 710. In either case, there is no interaction between the device function processor 706 and the telemetry processor 710 for time synchronization in such embodiments that include the clock circuit 718.

At all times, information transmitted wirelessly by the electronic device 704 to the electronic device 702 is forwarded unchanged by the telemetry processor 710 to the device function processor 706, and information originated by the device function processor 706 for wireless transmission to the electronic device 704 is likewise forwarded unchanged by the telemetry processor 710 to the electronic device 704. No signals related to polling requests, interrupts, triggers, synchronization or the like are originated by and sent from the device function processor 706 to the telemetry processor 710 or vice versa. Moreover, the device function processor 706 does not control any aspect of when or how the telemetry processor 710 transmits or receives messages or information packets, and the telemetry processor 710 does not control any aspect of when or how the device function processor 706 processes messages or information packets.

The electronic device 702 further includes a user interface 716 that is electrically connected to the device function processor 706. The user interface 716 illustratively includes at least a conventional key pad and a conventional display unit. The device function processor 706 may receives user input via the key pad, and may provide notifications or messages to the user via the display unit. The key pad may be or include one or more special purpose keys or buttons, a conventional full-function key board such as those typically found on a personal, laptop or notebook computer, or some number of keys or buttons between one key or button and a full-function key board. The display unit may be a conventional liquid crystal display (LCD) unit, or may alternatively be or include a conventional vacuum fluorescent display unit, a conventional light emitting diode (LED) display, one or more conventional light emitting diodes or segments, or the like. Alternatively or additionally, the user interface 716 may include one or more additional information input devices for providing information from a user or another electronic system to the electronic device 702. Examples of such one or more additional information input devices include, but should not be limited to, a conventional touch-screen display, conventional voice-activated information input circuitry, a conventional wired or wireless data port configured to communicate with an external electronic system or the like. Alternatively or additionally still, the user interface 716 may include one or more other notification or information transfer devices for providing information to a user or other electronic system. Examples of such one or more other notification or information transfer devices include, but should not be limited to, a conventional audio indication device, one or more conventional speakers, one or more conventional tactile indication devices, a conventional wired or wireless data port configured to communicate with an external electronic system or the like.

In embodiments in which the clock circuit 718 is provided in the form of a real time clock circuit, such a real time clock circuit illustratively includes a read time reference input and a time reference output both of which are electrically connected to the device function processor 706 and also to the telemetry processor 710, e.g., such as via a conventional inter-integrated circuit (I²C), multi-master serial communication bus, although this disclosure contemplates using other conventional electrical connection schemes. The real time clock circuit illustratively includes conventional real time clock circuitry and additional logic that is responsive to a read signal applied to the read time reference input to produce a time reference value at its time reference output. In one embodiment, the real time clock circuit is configured to support an alarm resolution and a time resolution of less than or equal to one second.

As it relates to the device function processor 706 and the telemetry processor 710, the real time clock circuit is generally responsive to a request for a new time reference to set at the requested time an output pulse, e.g., from low to high or vice versa, at its time reference output. Alternatively, the real time clock circuit is responsive to a request for a new time reference to transmit a time output via a standard communication interface, e.g., such as via a conventional inter-integrated circuit (I²C) multi-master serial communication bus. Illustratively, a conventional real time clock alarm function may be used to produce this time reference output. In any case, upon receiving the time reference from the real time clock circuit the device function processor 704 and the telemetry processor 710 are each independently operable to synchronize their internal timers to the received time reference and optionally to also update their individual time bases, e.g., such as by adjusting the frequencies of their internal clocks based on the received time reference or by updating their internal timing information based on the received time reference.

In embodiments in which the clock circuit 718 is a real time clock, the device function processor 706 and the telemetry processor 710 both have assigned times during which data can be transferred to and from the memory subsystem 714. As one example, the telemetry processor 710 may be configured to read from and write to the memory subsystem 714 every second starting a 0.0 seconds, and the device function processor 706 may be configured to also read and write to and from the memory subsystem 714 every second starting at 0.5 seconds. In this manner, communication conflicts between the processors 706 and 710 can be avoided.

In embodiments in which the clock circuit 718 is provided in the form of a clock generator circuit, such a clock generator circuit includes a conventional oscillator circuit that is configured to produce a periodic bit clock signal at a desired frequency and to produce an information packet clock signal at a desired frequency, in one example embodiment, the bit clock frequency may be 32.768 kHz and the information packet clock signal may be 1 Hz. In embodiments in which the clock circuit 718 is provided in the form of a clock generator circuit as just described, the transfer of inbound and outbound information packets between the device function processor 706 and the memory subsystem 714, and also between the telemetry processor 710 and the memory subsystem 714, is regulated solely by the clock signals produced by the clock generator circuit. The information packet clock signal starts the communication for each information packet to be transferred, and the bit clock signal clocks the transferring data bits to their destination. The clock generator circuit thus regulates the actual transfer of inbound and outbound information packets based on the bit clock signal, each transition (e.g., low to high or high to low) of which corresponds to a new bit of data, and the packet clock signal each transition (e.g., low to high or high to low) of which corresponds to a new information packet. Alternatively, the clock generator circuit 718 regulates the actual transfer of inbound and outbound information packets based on the packet clock signal each transition (e.g., low to high or high to low) of which corresponds to a new information packet. The device function processor 706 and the telemetry processor 710 synchronize their own internal clocks with the packet clock signal, and use their synchronized internal clock as a bit clock signal. Each transition of the device function processor's internal clock (e.g., low to high or high to low) or each, e.g., hundreds, or thousands of transitions of the device function processor clock (e.g. low to high or high to low) corresponds to a new bit of data. Each transition of the telemetry processor internal clock (e.g., low to high or high to low) or each, e.g., hundreds or thousands of transitions of the device function processor clock (e.g., low to high or high to low) corresponds to a new bit of data. Illustratively, the bit clock and the packet clock are continuously free running, and the operation of the clock generator circuit is independent of the state and operation of either of the device function processor 706 and the telemetry processor 710. Operation of the telemetry processor 710 is therefore maintained separate and independent from the operation of the device function processor 706.

Figure 16:
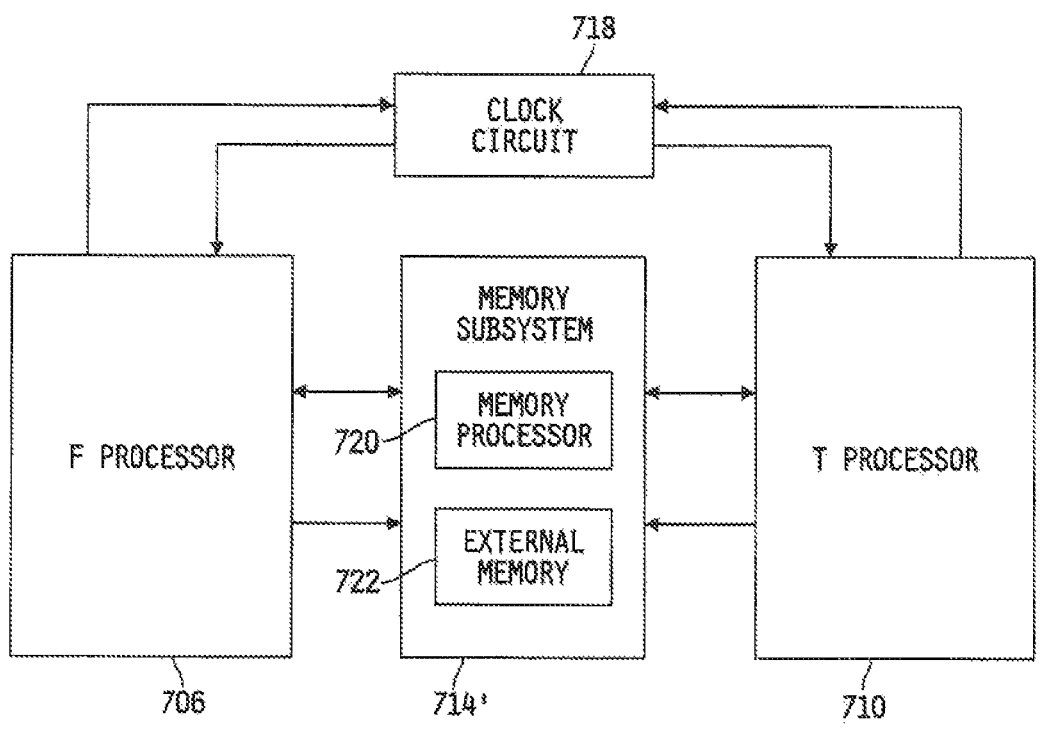
FIG. 16 is a diagram of one illustrative embodiment of the memory subsystem of FIG. 15.

Referring now to FIG. 16, a diagram of one illustrative embodiment 714' of the memory subsystem of FIG. 15 is shown in the context of the device function processor 706, the telemetry processor 710 and the clock circuit 718. In the illustrated embodiment, the memory subsystem 714' includes a memory processor 720 that is electrically connected to an external memory unit 722, i.e., an externally attached memory unit. In the embodiment 714', the memory processor 720 handles the communication between the external memory unit 722 and the device function processor 706 and also between the external memory unit 722 and the telemetry processor 710. The memory processor 720 may further be used to schedule access to the memory unit 722, to mark new data or delete old data, to set or delete flags in the memory, to set or delete electrical outputs (e.g., digital inputs, output lines (or the like. The data is buffered in the external memory unit 722, and the memory processor 720 illustratively includes an interface to the device function processor 706, the telemetry processor 710 and the external memory 722. A serial or a parallel interface may be used to connect the memory processor 720 to the memory unit 722. The memory processor may be, for example, but should not be limited to, a model LPC2210 16-bit microcontroller that is commercially available from NXP, a model HD64F3067 16-bit microcontroller that is commercially available from Renesas, or a model MSP430F2471 16-bit microcontroller that is commercially available from Texas Instruments. The memory unit 722 may be, for example, but should not be limited to, a model FM22L16 4 Mb FRAM that is commercially available from Ramtron or a model CY14B101L 1 MB nvSRAM that is commercially available from Cypress if the memory unit 722 is to be connected via a parallel interface, or a model AT25F1024 1 Mb SPI bus serial Flash that is commercially available from Atmel, a model FM25L512 512 Kb SPI FRAM that is commercially available from Ramtron, a model AT45DB011B 1 Mb SPI Flash that is available from Atmel or a model A25L10P 1 Mb SPI Flash that is commercially available from AMIC Technology if the memory unit 722 is to be connected via a serial interface.

Figure 17:
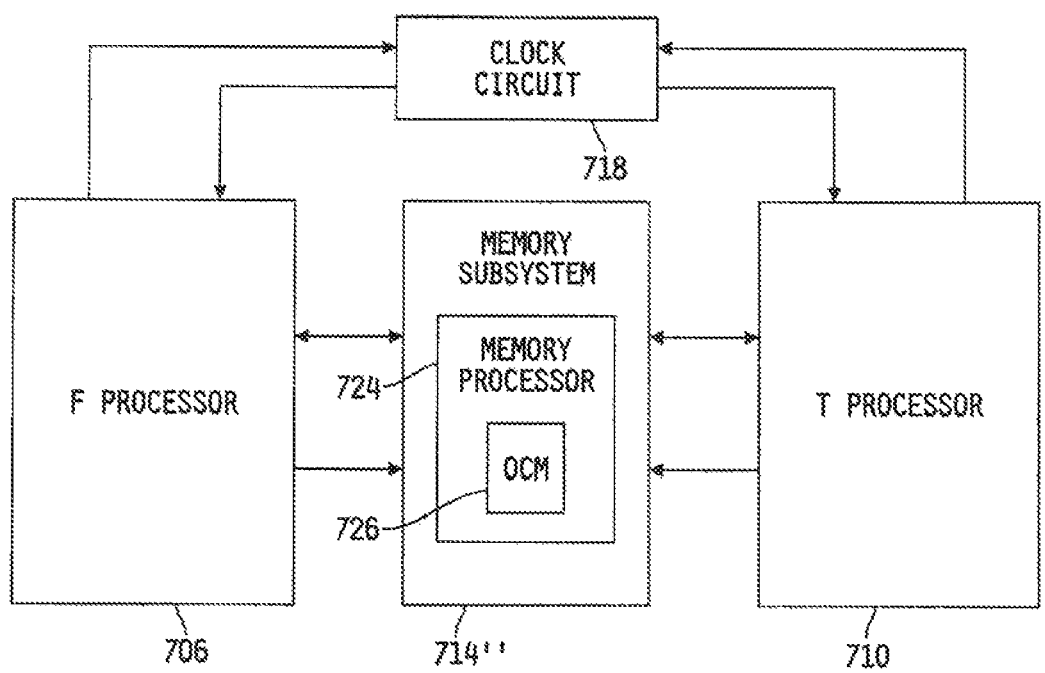
FIG. 17 is a diagram of another illustrative embodiment of the memory subsystem of FIG. 15.

Referring to FIG. 17, a diagram of another illustrative embodiment 714" of the memory subsystem of FIG. 15 is shown in the context of the device function processor 706, the telemetry processor 710 and the clock circuit 718. In the illustrated embodiment, the memory subsystem 714" includes a memory processor 724 that is electrically connected to an on-chip memory (OCM) unit 726. In the embodiment 714', the memory processor 724 handles the communication between the memory unit 726 and the device function processor 706 and also between the memory unit 726 and the telemetry processor 710. All data buffering is done inside the memory processor 724, and the communication scheme may be adjusted to the memory size. The MSP430F1611 16-bit microcontroller that is commercially available from Texas Instruments has 10 kb of SRAM, the uPSD3254A 8032 core microcontroller that is commercially available from STMicroeletronics has 32 kb of SRAM, 256 kb of Flash and 32 kb of $2^{nd}$ Flash, and the ATmega1281 8-bit microcontroller that is commercially available from Atmel has 128 kb of self-programming Flash and 8 kb of SRAM, for example.

Figure 18:
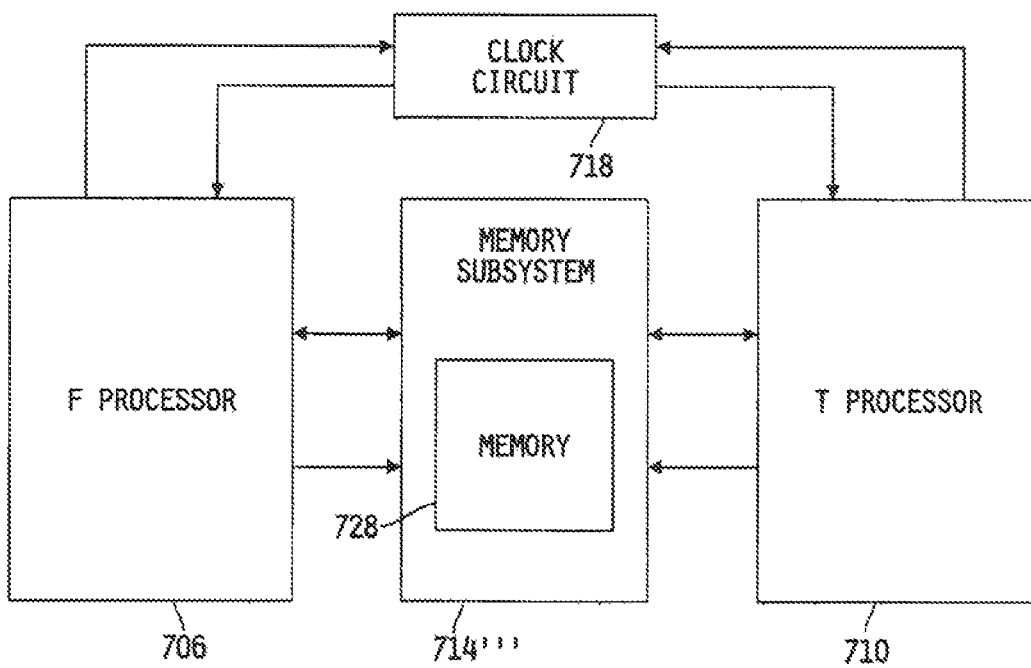
FIG. 18 is a diagram of yet another illustrative embodiment of the memory subsystem of FIG. 15.

Referring now to FIG. 18, a diagram of another illustrative embodiment 714''' of the memory subsystem of FIG. 15 is shown in the context of the device function processor 706, the telemetry processor 710 and the clock circuit 718. In the illustrated embodiment, the memory subsystem 714''' includes only a memory unit 728 that provides for data exchange between the device function processor 706 and the telemetry processor 710 without any data flow control between the two processors 706 and 710. The memory unit 728 serves as a buffer that separates the processors 706 and 710, and has no intelligence or data analysis capabilities. Data are read from locations where they were written to by the device function processor 706 and the telemetry processor 710. The memory unit 728 may be connected to the processor 706 and 710 via a parallel or serial interface. The memory unit 728 may be, for example, but should not be limited to, a model FM22L16 4 Mb FRAM that is commercially available from Ramtron or a model CY14B101L 1 MB nvSRAM that is commercially available from Cypress if the memory unit 728 is to be connected via a parallel interface, or a model AT25F1024 1 Mb SPI bus serial Flash that is commercially available from Atmel, a model FM25L512 512 Kb SPI FRAM that is commercially available from Ramtron, a model AT45DB011B 1 Mb SPI Flash that is available from Atmel or a model A25L10P 1 Mb SPI Flash that is commercially available from AMIC Technology if the memory unit 728 is to be connected via a serial interface.

Figure 19A:
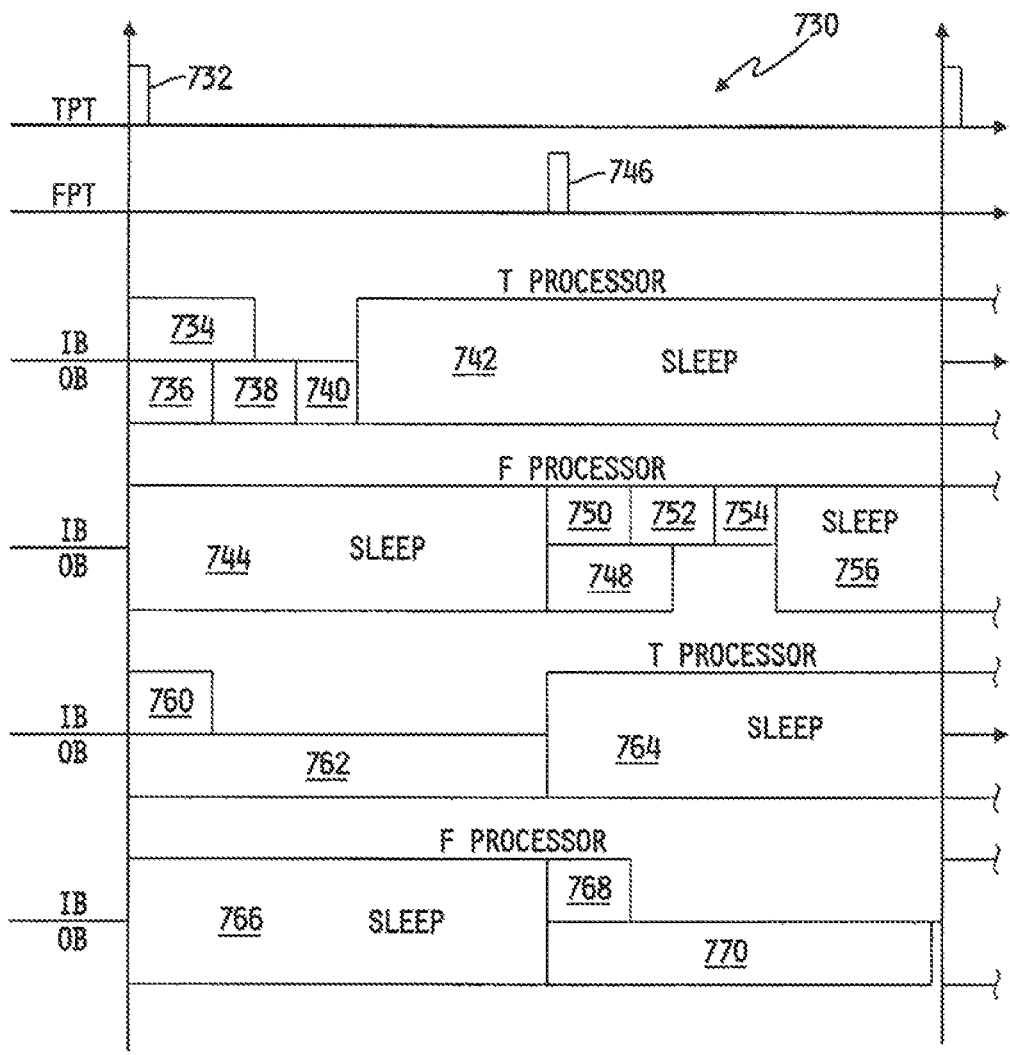
FIG. 19A is a timing diagram illustrating operation of the telemetry processor and the device function processor of FIG. 15 during information exchange at a normal data exchange rate and during information exchange at a speed data exchange rate.

Referring now to FIG. 19A, a timing diagram 730 is shown illustrating operation of the telemetry processor 710 and the device function processor 706, in embodiments of the electronic device 702 of FIG. 15 that include the clock circuit 718 in the form of a real time clock, during information exchange at a normal data exchange rate and during information exchange at a speed data exchange rate. As described in an example hereinabove, the telemetry processor 710 may be configured to read from and write to the memory subsystem 714-714''' every second starting a 0.0 seconds, and the device function processor 706 may be configured to also read from and write to the memory subsystem 714-714''' every second starting at 0.5 seconds. In this manner, communication conflicts between the processors 706 and 710 can be avoided. As illustrated in FIG. 19A, the telemetry processor 710 is responsive to the rising edge of an internally generated timing pulse 732 to write an information packet 734 to the memory subsystem 714-714''' and to read and information packet 736 from the memory subsystem 714-714'''. After the information packet 736 is read from the memory subsystem 714-714''' the telemetry processor 710 is operable to pack the information packet into the wireless communication protocol structure at 738 and to then wirelessly transmit the packed information packet to the electronic device 704 at 740. Thereafter at 742, the telemetry processor 710 transitions to a sleep state.

Figure 19B:
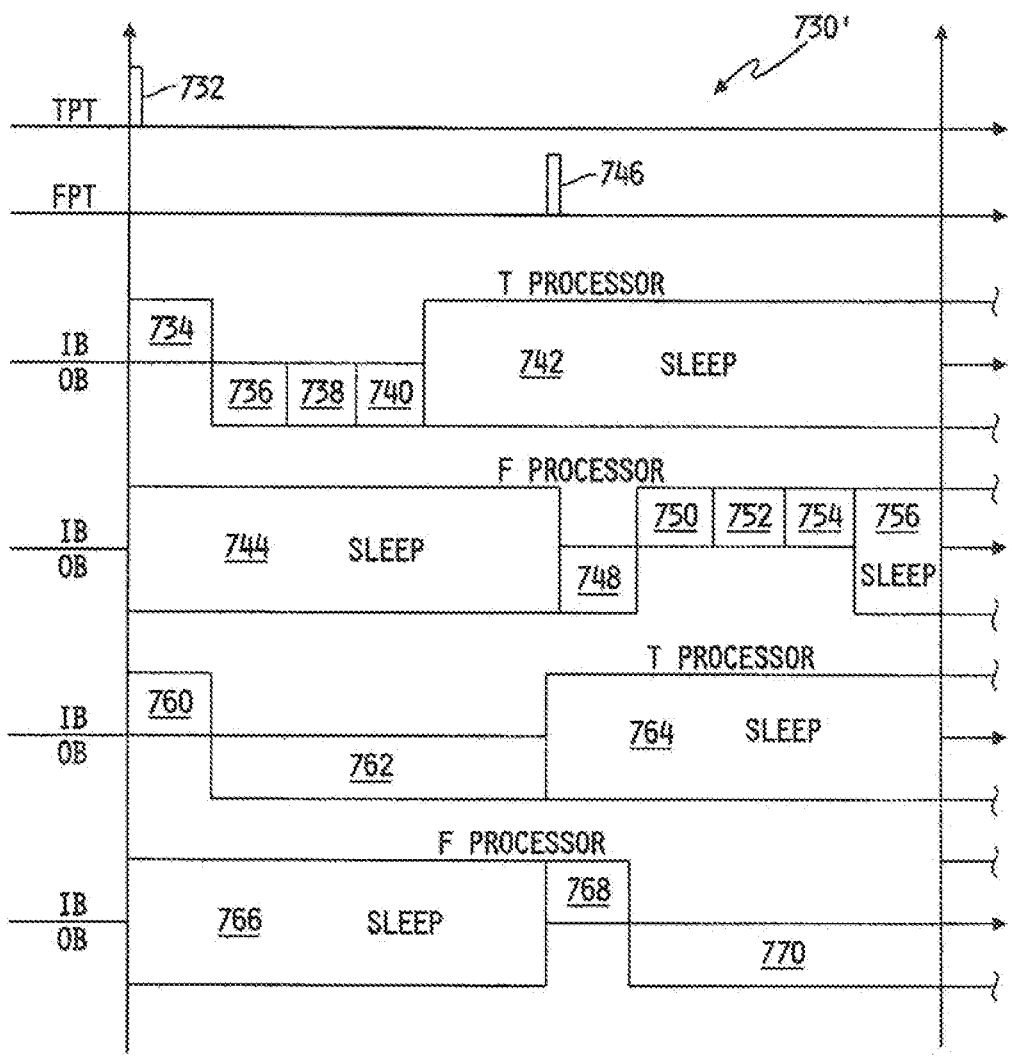
FIG. 19B shows a timing diagram illustrating operation of the telemetry processor and the device function processor of FIG. 15 that include the clock circuit in the form of a real time clock.

While the telemetry processor 710 is active as just described, the device function processor 706 is in a sleep state 744. The device function processor 706 is then responsive to a rising edge of an internally generated timing pulse 746 to write an information packet 748 to the memory subsystem 714-714''' and to read an information packet 750 from the memory subsystem 714-714'''. After the information packet 750 is read from the memory subsystem 714-714''' the device function processor 706 is operable to process the data contained in the information packet at 752 and to then act upon the data at 754. Thereafter at 756, the device function processor 706 transitions back to its sleep state. If as in the example given above, the entire packet transfer process just described is carried out every second, it can be seen that by staggering the operation of the telemetry processor 710 and the operation of the device function processor 706 by approximately 0.5 seconds (e.g. time elapsed between TPT and FPT), communication conflicts between the two processors 706 and 710 are avoided. In the example given above, the telemetry processor accesses the memory during the processes 734 and 736. The device function processor accesses the memory during the processes 748 and 750. It should be clear that communication conflicts between the two processors are avoided if the sum of the duration of the processes 734 and 736 is smaller than 0.5 seconds (e.g., time elapsed between TPT and FPT) and if the sum of the duration of the processes 748 and 750 is smaller than 0.5 seconds (e.g., time elapsed between TPT and FPT). Alternatively to FIG. 19A, FIG. 19B shows a timing diagram 730' illustrating operation of the telemetry processor 710 and the device function processor 706, in embodiments of the electronic device 702 of FIG. 15 that include the clock circuit 718 in the form of a real time clock, during information exchange at a normal data exchange rate and during information exchange at a speed data exchange rate. The timing diagram 730' differs from the liming diagram 730 in the way that the processes 734 and 736 and the processes 748 and 750 are sequential.

Multiple inbound and/or outbound information packets may alternatively be transmitted at higher data rates as also illustrated in FIG. 19. For example, the telemetry processor 710 is responsive to the rising edge of the internally generated timing pulse 732 to write a single information packet 760 to the memory subsystem 714-714''' and to begin continuously reading multiple information packet 762 from the memory subsystem 714-714'''. After the first occurrence of the multiple information packets 762 having been read from the memory subsystem 714-714''' or the rising edge of the internally generated timing pulse 746, the telemetry processor 710 transitions to a sleep state at 764. Thus, in the high data rate mode, only as many information packets as can be read between the pulses 732 and 746 will be read and removed from the memory subsystem 714-714'''. The remaining information packets may be read during the next information packet cycle.

Figure 19C:
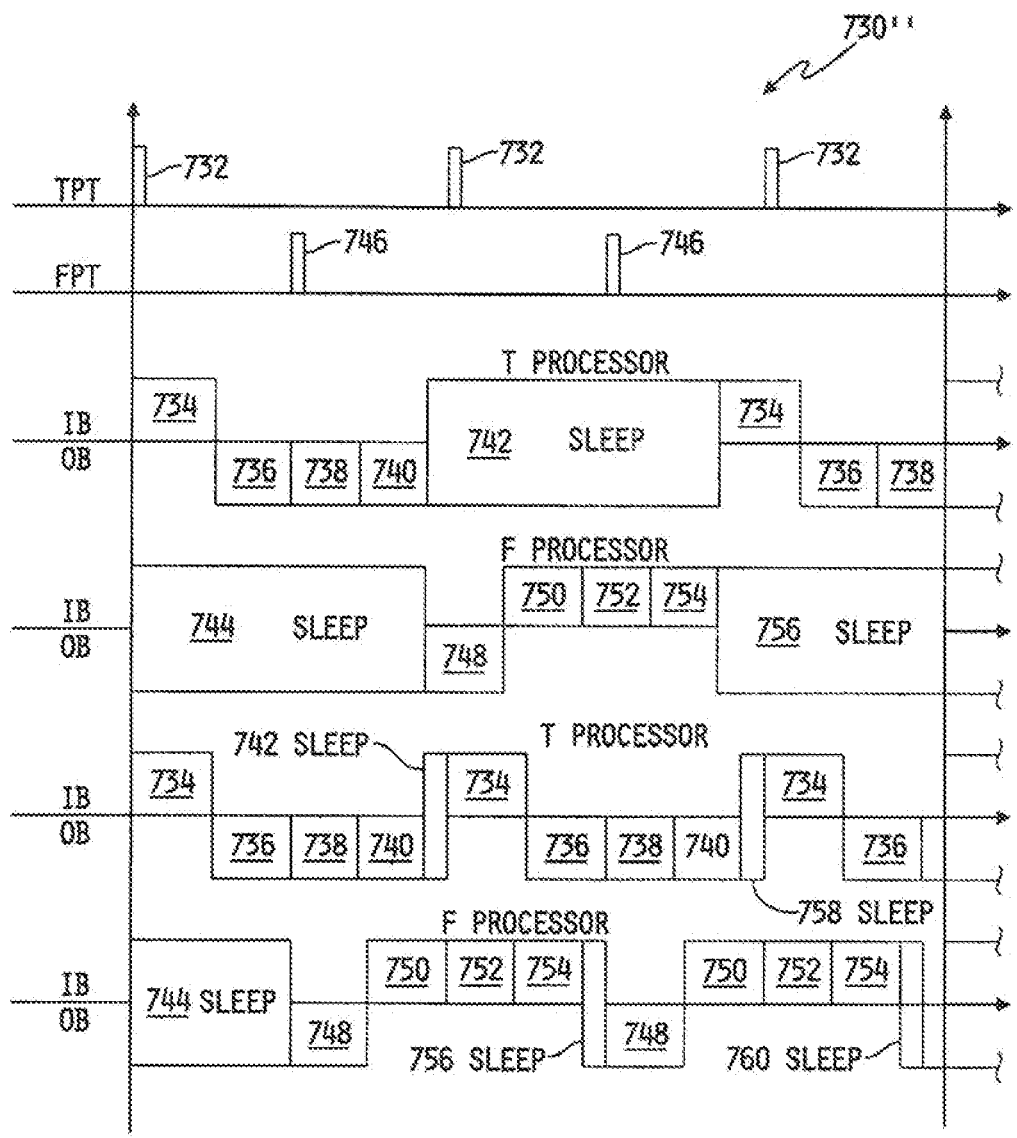
FIG. 19C shows a timing diagram illustrating high data rate operation of the telemetry processor and the device function processor in of FIG. 15 that include the clock circuit in the form of a real time clock.

While the telemetry processor 710 is active as just described, the device function processor 706 is in a sleep state 766. The device function processor 706 is then responsive to the rising edge of the internally generated timing pulse 746 to write multiple information packets 770 to the memory subsystem 714-714''' and to read, a single information packet 768 from the memory subsystem 714-714'''. After the information packet 768 is read from the memory subsystem 714-714''' the telemetry processor 710 is operable to process the data contained in the information packet as described above, in embodiments in which multiple inbound and/or outbound information packets are alternatively transmitted at higher data rates, as illustrated in FIG. 19C for example, the duration between two subsequent rising edges of the internally generated timing pulse 732" to write a single information packet 760" to the memory subsystem 714-714''' and to read a single information packet 762" from the memory subsystem. 714-714''' can be modified in such a way that the sleeping periods 742, 744 and 756 are minimized.

Figure 20:
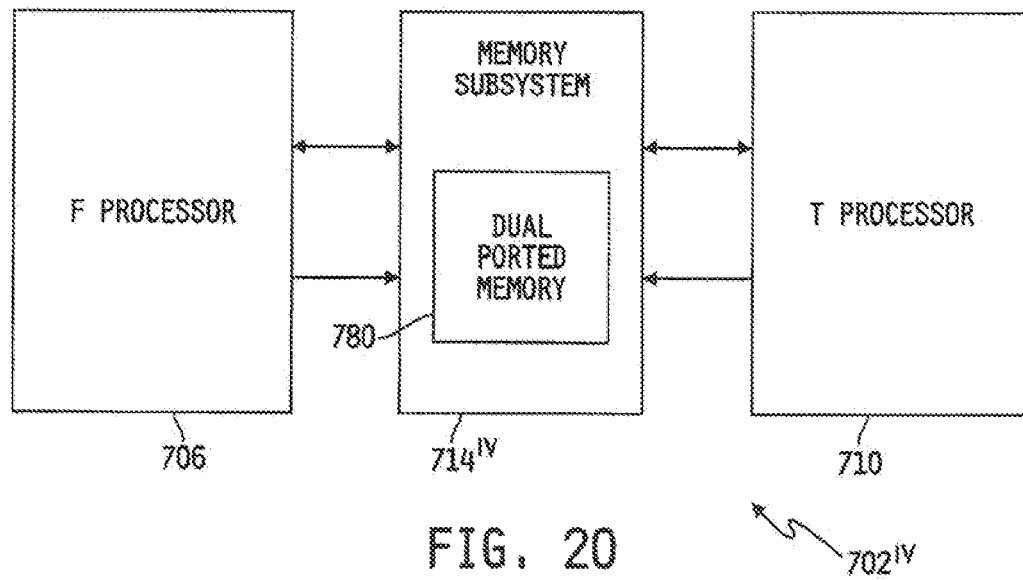
FIG. 20 is a diagram of one illustrative embodiment of the memory subsystem of FIG. 15 in an embodiment of the electronic device that does not include the clock circuit.
Figure 21:
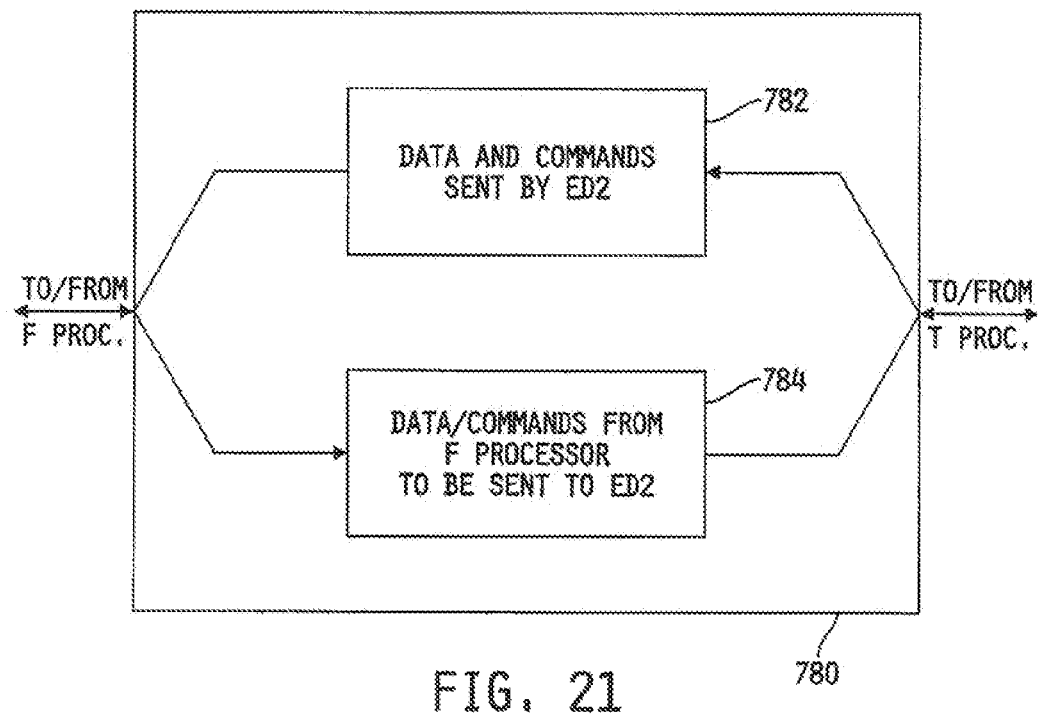
FIG. 21 is a diagram of one illustrative embodiment of the dual ported memory of FIG. 20.

Referring now to FIG. 20, one illustrative variant 714$^{iv}$ of the memory subsystem of FIG. 15 is shown in an embodiment of the electronic device that does not include the clock circuit 718. In the illustrated embodiment, the memory subsystem 714$^{iv}$ includes only a dual ported memory device 780. Without a clock circuit 718, a stand alone memory unit has to support two ports concurrently, i.e., one from which to read data and one to which to write data. As illustrated in FIG. 21, the dual ported memory device 780 illustratively includes two separate and dedicated memory buffers 782 and 784. The memory buffer 782 is electrically connected to both the telemetry processor 710 and to the device function processor 706, and is configured to store data and commands written thereto by the telemetry processor 710 for subsequent reading by the device function processor 706. The memory buffer 784 is also electrically connected to both the telemetry processor 710 and to the device function processor 706, and is configured to store data and commands written thereto by the device function processor 706 for subsequent reading by the device telemetry processor 710. The dual ported memory device 780 thus stores data packets sent by either of the processors 706 and 710 while maintaining the operation of each of the processors 706 and 710 separate from each other. Both of the processors 706 and 710 can access the memory device 780 at the same time, which is necessary since the present embodiment does not include the clock circuit 718, since the two processors 706 and 710 operate autonomously and independently of each other. While dual ported memory devices having serial interfaces may be desirable in some embodiments, none are believed to be currently available. Dual ported RAM devices having parallel bus interfaces are available commercially, such as, but not limited to, the CV7009V dual port RAM that is available from Cypress and the IDT70T631 256 kb dual-port RAM available from Integrated Device Technology (IDT).

Figure 22:
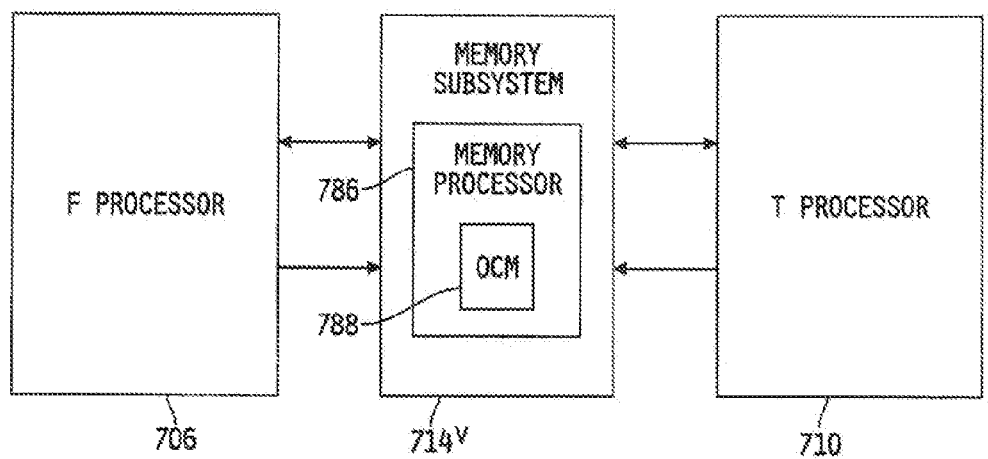
FIG. 22 is a diagram of another illustrative embodiment of the memory subsystem of FIG. 15 in an embodiment of the electronic device that does not include the clock circuit.
Figure 23:
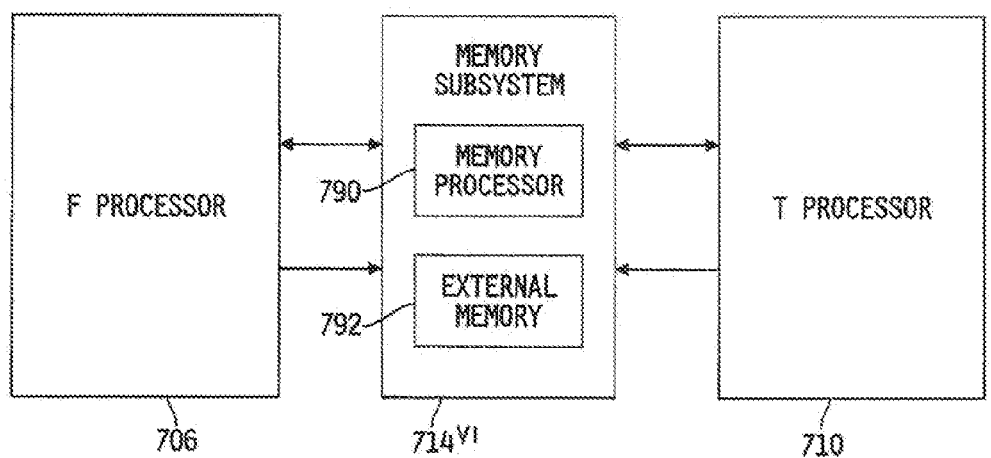
FIG. 23 is a diagram of yet another illustrative embodiment of the memory subsystem of FIG. 15 in an embodiment of the electronic device that does not include the clock circuit.

Referring now to FIG. 22 a diagram is shown of another illustrative embodiment 714$^v$ of the memory subsystem of FIG. 15 in an embodiment of the electronic device 702 that does not include the clock circuit 718. In this embodiment, the memory subsystem 714$^v$ includes a memory processor 786 and an on-chip memory unit 788. In still another illustrative embodiment as shown in FIG. 23, a memory subsystem 714$^{vi}$ includes a memory processor 790 and an external memory unit 792. In either case, the data is sent by either processor 706 and 710 to the memory processor 786, 790, and the memory processor 786, 790 then stores the data in the memory unit 788, 792. Data is also read from the memory unit 788, 792 by the memory processor 786, 790 and then sent to an appropriate one of the device function processor 706 and the telemetry processor 710. The memory processor 786, 790 determines, based on the received data and on internal status, if and where the data is written in the memory unit 788, 792. Depending upon the communication scheme, information about new and old data can be sent to the device function processor 706 or the telemetry processor 710 or can be added to the stored data. Examples of the memory processor 786 and the memory 788 are as given above in reference to FIG. 17, and examples of the memory processor 790 and the memory 792 are as given above in reference to FIG. 16.

Figure 24:
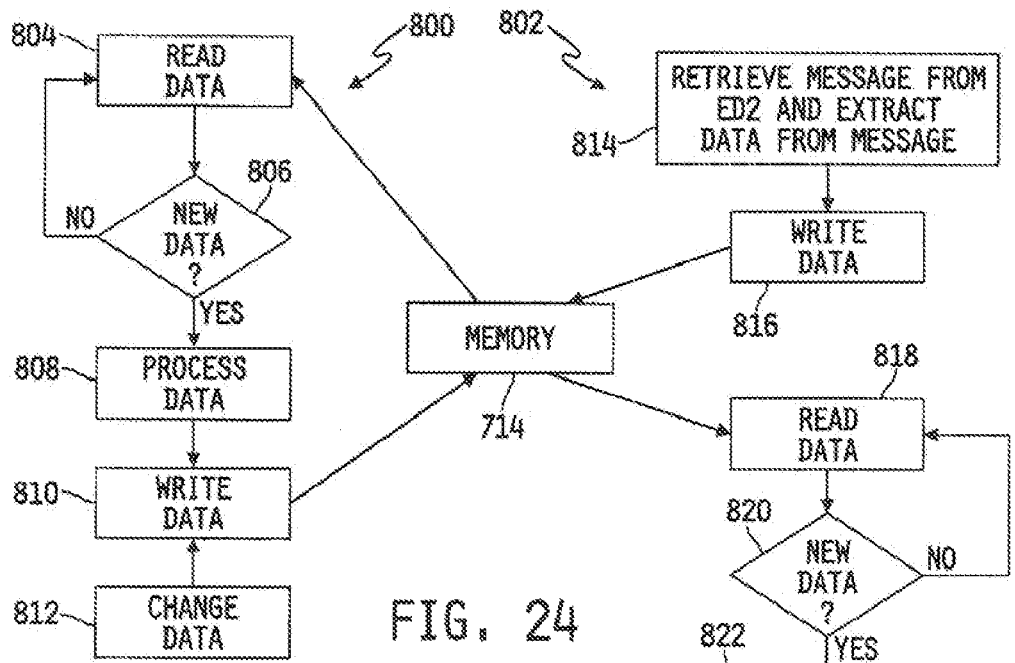
FIG. 24 is a flowchart of one illustrative embodiment of a process for managing the communication of information between the device function processor and the telemetry processor in any of the embodiments illustrated in FIGS. 15-23.

Referring now to FIG. 24, a flowchart is shown of one illustrative embodiment of a process for managing the communication of information between the device function processor 706 and the telemetry processor 710 in any of the embodiments illustrated in FIGS. 15-23. The illustrated process comprises two sub-processes 800 and 802 that are carried out within the device function processor 706 and the telemetry processor 710 respectively. The process illustrated in FIG. 2-4 manages information exchange between the device function processor 706 and the memory subsystem 714 and between the telemetry processor 710 and the memory subsystem 714. The process illustrated in FIG. 24 presumes that the memory subsystem 714 cannot or does not provide any indication of its write status and that neither the device function processor 706 nor the telemetry module 710 can or does determine the write status of the memory subsystem 714.

Via the memory subsystem 714, information packet exchange takes place between the device function processor 706 and the telemetry processor 710. The sub-process 800 for managing by the device function processor 706 of information exchange with the memory subsystem 714 begins at step 804 where the device function processor 706 reads data in the form of an information packet from the memory subsystem 714. Thereafter at step 806, the device function processor 706 conducts an analysis of the data read at step 804 to determine whether the data is new, i.e., whether the device function processor 706 has previously read the data contained in the information packet. If not, the device function processor 706 may or may not write data, e.g., status data to the memory subsystem 714, and the sub-process 800 loops back to step 804. If instead the device function processor 706 determines that the information packet read at step 804 contains new data, it is processed by the device function processor 706 at step 808 and any results, e.g., commands or data, generated by the processing of the new data and/or any changed data from step 812 are written by the device function processor 706 to the memory subsystem 714 at step 810. Alternatively, any results of a previous packet read, or any results of the device function processor functions, or no results, are written or respectively not written at step 810 to the memory subsystem 714. The device function processor 706 periodically executes the sub-process 800 independently of the timing of operation of the memory subsystem 714 and also independently of the timing of operation of the telemetry processor 710.

The sub-process 802 for managing by the telemetry processor 710 of information exchange with the device function processor 706 via the memory subsystem 714 begins at step 814 where the telemetry processor 710 wirelessly receives a message from the electronic device 704 via the communication link 703 and extracts the information packet from the wireless communication protocol structure. Thereafter at step 816, the telemetry processor 710 writes the extracted information packet to the memory subsystem 714. In carrying out steps 814 and 816, the telemetry processor 710 does not read, interpret or act upon any substantive data contained in the information packet, but rather only extracts the information packet from the communication protocol structure, e.g., unpacks it from the BlueTooth® communication protocol structure, and writes the packet to the memory subsystem 714.

At step 818, the telemetry processor 710 reads data in the form of an information packet from the memory subsystem 714. Thereafter at step 820, the telemetry processor 710 conducts an analysis of the data read from the memory subsystem 714 at step 818 to determine whether the data is new, i.e., whether the telemetry processor 710 has previously read the data contained in the information packet. It will be understood that at step 820, the analysis undertaken by the telemetry processor 710 determines only whether the data contained in the information packet is new, i.e., has not been read by the telemetry processor 710 before, and does not interpret or act upon any instructions or information contained in the data. If the telemetry processor 710 determines at step 820 that the data is not new, the telemetry processor 710 does not wirelessly transmit anything to the electronic device 704. On the other hand, if the telemetry processor 710 determines at step 820 that the information packet read from the memory subsystem 714 at step 818 contains new data, the telemetry processor 710 packs the information packet into the wireless communication protocol structure and wirelessly transmits the information packet to the electronic device 704 at step 822.

At steps 806 and 820, the device function processor 706 and the telemetry processor 710 respectively analyze data contained in the information packet read from the memory subsystem 714 to determine whether the information packet contains new data. In one embodiment, this is accomplished by implementing a bitwise comparison with the previously read information packet and, if at least one bit of the compared packets differs, the information packet is considered new. In one alternative embodiment, the header of the information packet may contain a count value, a set of random bits or a flag, and the modules 706, 710 may be configured in this embodiment to determine whether an information packet contains new data by analyzing the header to determine whether the count value or set of random bits differs from that or those of the previous information packet or if the flag has been set or cleared. Those skilled in the art will recognize other conventional techniques for determining whether an information packet contains new data, and any such other techniques are contemplated by this disclosure. In any case it will be understood that any references to the memory subsystem 714 in the description of the process of FIG. 24 may refer to the memory subsystem 714 generally and/or to any one or more of the memory subsystem embodiments 714'-714$^{vi}$ illustrated and described herein.

Figure 25:
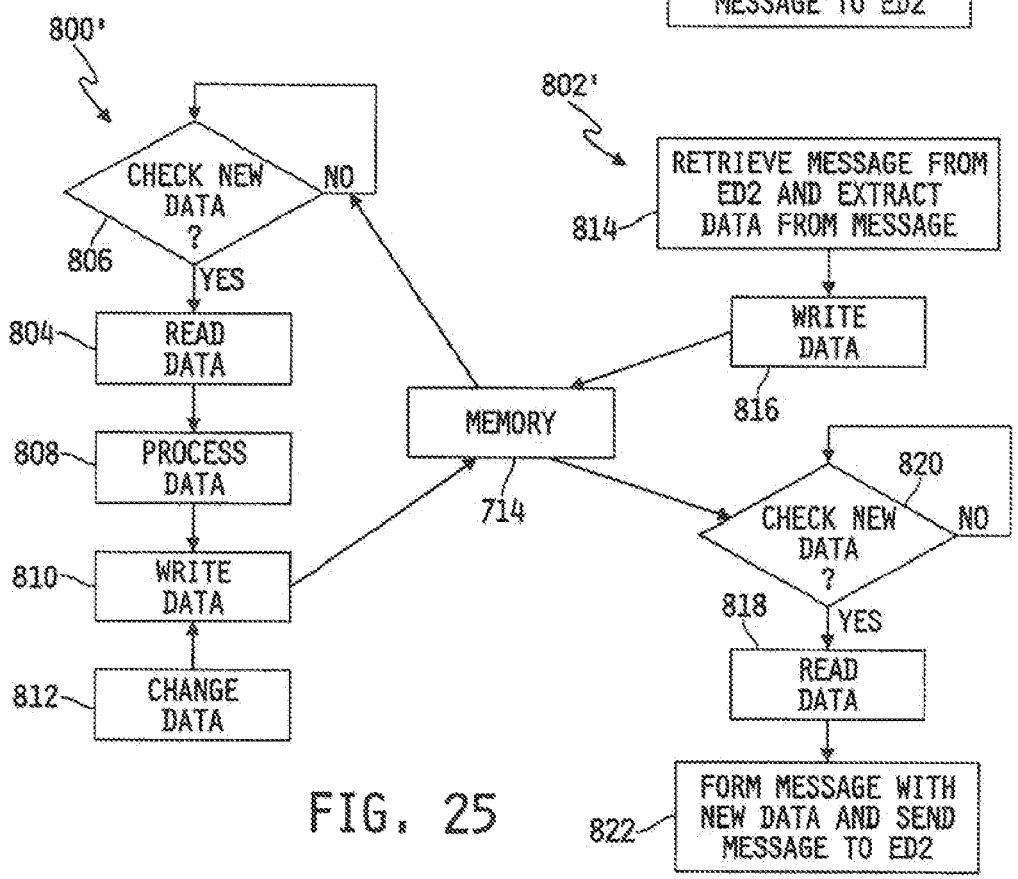
FIG. 25 is a flowchart of another illustrative embodiment of a process for managing the communication of information between the device function processor and the telemetry processor in any of the embodiments illustrated in FIGS. 15-23.

Referring now to FIG. 25, a flowchart is shown of another illustrative embodiment of a process for managing the communication of information between the device function processor 706 and the telemetry processor 710 in any of the embodiments illustrated in FIGS. 15-23. The illustrated process comprises two sub-processes 800' and 802' that are carried out within the device function processor 706 and the telemetry processor 710 respectively. As with the process illustrated in FIG. 24, the process illustrated in FIG. 25 manages information exchange between the device function processor 706 and the memory subsystem 714 and between the telemetry processor 710 and the memory subsystem 714. However, unlike the process illustrated in FIG. 24, the process illustrated in FIG. 25 presumes that the memory subsystem 714 can and does provide a indication of its write status and/or that either the device function processor 706 or the telemetry module 710 can and does determine the write status of the memory subsystem 714. The various steps of the sub-processes 800' and 802' are identical to those of the sub-processes 800 and 802 except that in the sub-processes 800' and 802' the steps of the sub-processes 800 and 802 are somewhat rearranged in any case, like numbers are used in the sub-processes 800' and 802' to identify like steps of the sub-processes 800 and 802.

The sub-process 800' for managing by the device function processor 706 of information exchange with the memory subsystem 714 begins at step 806 where the device function processor 706 checks the write status of the memory subsystem 714. If the write status checked at step 806 indicates that no new data has been written to the memory subsystem 714 since last executing step 806, the sub-process 800' loops back to re-execute step 806 until the write status changes. If and when the write status checked at step 806 indicates that new data has been written by the telemetry processor 710 to the memory subsystem 714, the sub-process 800' advances to step 804 where the device function processor 706 reads the data in the form of an information packet from the memory subsystem 714. Thereafter at step 808, the read data is processed by the device function processor 706 and any results, e.g., commands or data, generated by the processing of the new data and/or any changed data from step 812 are written by the device function processor 706 to the memory subsystem 714 at step 810. The device function processor 706 periodically executes the sub-process 800 independently of the timing of operation of the memory subsystem 714 and also independently of the timing of operation of the telemetry processor 710.

The sub-process 802' for managing by the telemetry processor 710 of information exchange with the device function processor 706 via the memory subsystem 714 begins at step 814 where the telemetry processor 710 wirelessly receives a message from the electronic device 704 via the communication link 703 and extracts the information packet from the wireless communication protocol structure. Thereafter at step 816, the telemetry processor 710 writes the extracted information packet to the memory subsystem 714. Again, in carrying out steps 814 and 816, the telemetry processor 710 does not read, interpret or act upon any substantive data contained in the information packet, but rather only extracts the information packet from the communication protocol structure, e.g., unpacks it from the BlueTooth® communication protocol structure, and writes the packet to the memory subsystem 714.

At step 820, the telemetry processor 710 checks the write status of the memory subsystem 714. If the write status checked at step 820 indicates that no new data has been written to the memory subsystem 714 since last executing step 820, the sub-process 802' loops back to re-execute step 820 until the write status changes. If and when the write status checked at step 820 indicates that new data has been written by the device function processor 706 to the memory subsystem 714, the sub-process 802' advances to step 818 to read data in the form of an information packet from the memory subsystem 714. Thereafter at step 822, the telemetry processor 710 packs the information packet into the wireless communication protocol structure and wirelessly transmits the information packet to the electronic device 704. It will be understood that any references to the memory subsystem 714 in the description of the process of FIG. 25 may refer to the memory subsystem 714 generally and/or to any one or more of the memory subsystem embodiments 714'-714$^{vi}$ illustrated and described herein.

Figure 26:
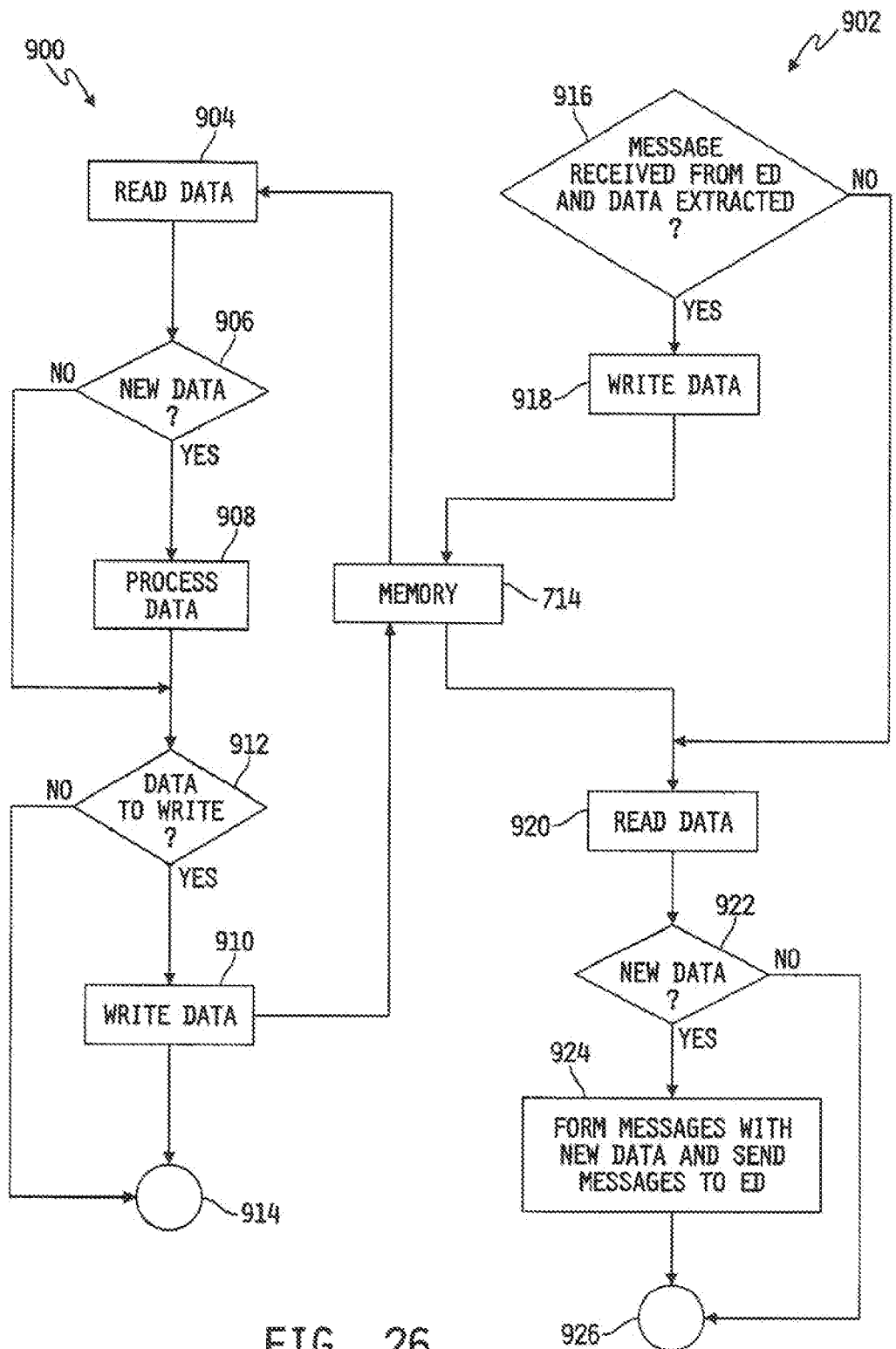
FIG. 26 is a flowchart of yet another illustrative embodiment of a process for managing the communication of information between the device function processor and the telemetry processor in any of the embodiments illustrated in FIGS. 15-23.

Referring now to FIG. 26, a flow chart is shown in another illustrative embodiment of a process for managing the communication of information between the device function processor 706 and the telemetry processor 710 in any of the embodiments illustrated in FIGS. 15-23. The illustrated process comprises two subprocesses 900 and 902 that are carried out within the device function processor 706 and the telemetry processor 710 respectively. As with the process illustrated in FIG. 24, the process illustrated in FIG. 26 manages information exchange between the device function processor 706 and the memory subsystem 714 and between the telemetry processor 710 and the memory subsystem 714. The various steps of the sub-processes 900 and 902 are nearly identical to those of the sub-processes 800 and 802 except that in the sub-processes 900 and 902 the steps of the sub-processes 800 and 802 are somewhat rearranged and that the step of change data 812 has been replaced by the data to write 912. However, unlike the process illustrated in FIG. 24, the process illustrated in FIG. 26 does not loop back if the write status check at step 806, 906 indicates that no new data has been written to the memory subsystem 714 since last executing step 806, 906. The subprocess 900 advances to the step 912. At step 912, the process 900 checks if data are to be written to the memory subsystem 714. If and when data are to be written to the memory subsystem 714, the subprocess 900 advances to step 910 and writes the information in the memory subsystem 714 and then advance to step 914. If and when no information is to be written to the memory subsystem 714, the subprocess 900 advances to step 914. At step 914 the subprocess 900 is stopped.

The sub-process 902 for managing by the telemetry processor 710 of information exchange with the device function processor 706 via the memory subsystem 714 begins at step 916 where the telemetry processor 710 checks if an information packet of a wirelessly received message from the electronic device 704 via the communication link 703 and extracted from the wireless communication protocol structure is to be exchanged with the device function processor. When and if information is to be exchanged, the process 902 advances to the step 918. Thereafter at step 918, the telemetry processor 710 writes the extracted information packet to the memory subsystem 714. Again, in carrying out steps 916 and 918, the telemetry processor 710 does not read, interpret or act upon any substantive data contained in the information packet, but rather only extracts the information packet from the communication protocol structure, e.g., unpacks it from the BlueTooth® communication protocol structure, and writes the packet to the memory subsystem 714.

At step 920, the telemetry processor 710 reads data in the form of an information packet from the memory subsystem 714. Thereafter at step 922, the telemetry processor 710 conducts an analysis of the data read from the memory subsystem 714 at step 920 to determine whether the data is new, i.e., whether the telemetry processor 710 has previously read the data contained in the information packet. It will be understood that at step 922, the analysis undertaken by the telemetry processor 710 determines only whether the data contained in the information packet is new, i.e., has not been read by the telemetry processor 710 before, and does not interpret or act upon any instructions or information contained in the data. If the telemetry processor 710 determines at step 922 that the data is not new, the telemetry processor 710 does not wirelessly transmit anything to the electronic device 704 and the process 902 advances to step 926. On the other hand, if the telemetry processor 710 determines at step 922 that the information packet read from the memory subsystem 714 at step 920 contains new data, the telemetry processor 710 packs the information packet into the wireless communication protocol structure and wirelessly transmits the information packet to the electronic device 704 at step 924. Thereafter, the process 902 advances to step 926. At step 926 the subprocess 902 is stopped.

Figure 27:
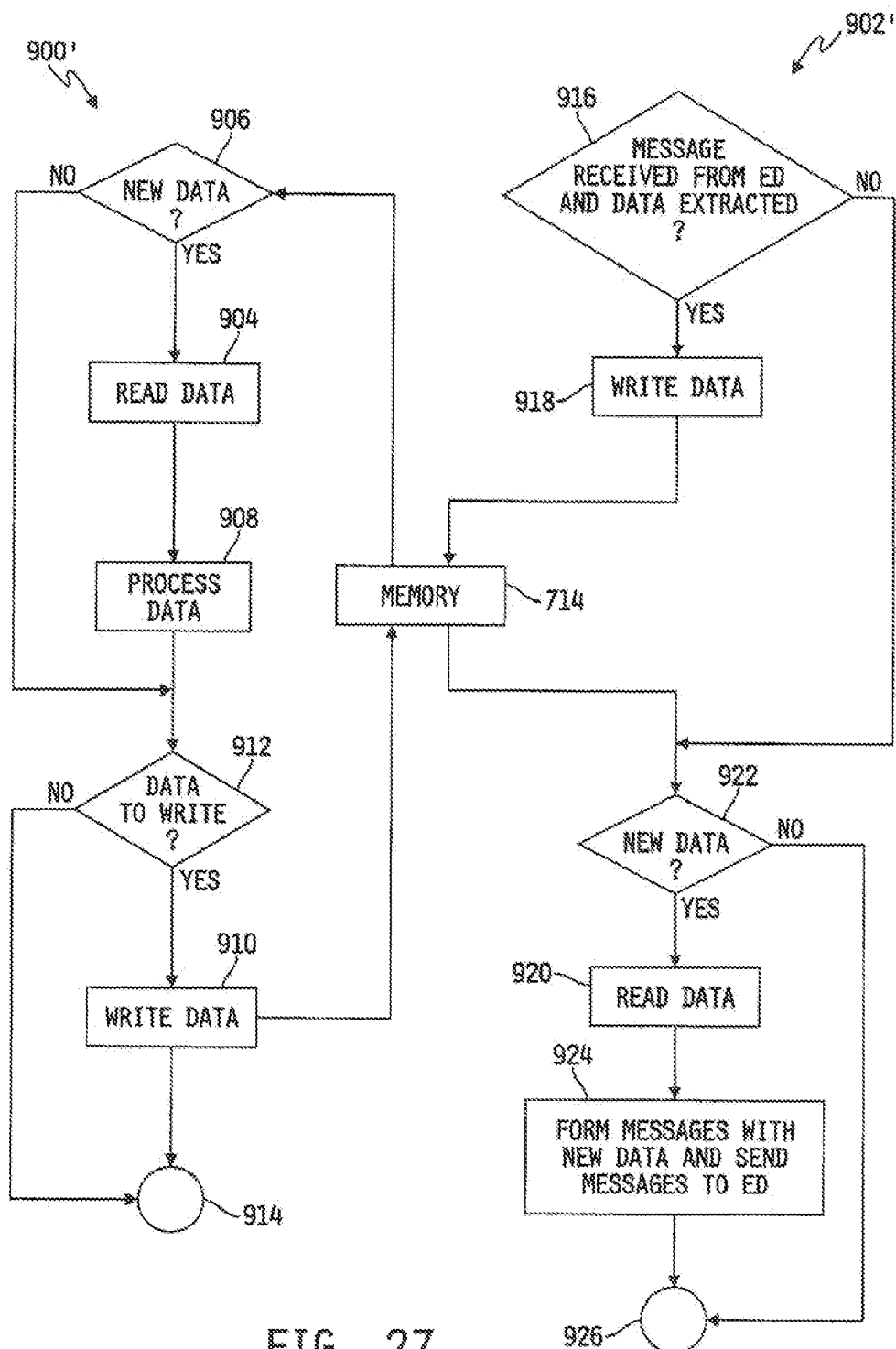
FIG. 27 is a flowchart of still another illustrative embodiment of a process for managing the communication of information between the device function processor and the telemetry processor in any of the embodiments illustrated in FIGS. 15-23.

Referring now to FIG. 27, a flowchart is shown of another illustrative embodiment of a process for managing the communication of information between the device function processor 706 and the telemetry processor 710 in any of the embodiments illustrated in FIGS. 15-23. The illustrated process comprises two sub-processes 900' and 902' that are carried out within the device function processor 706 and the telemetry processor 710 respectively. As with the process illustrated in FIG. 26, the process illustrated in FIG. 27 manages information exchange between the device function processor 706 and the memory subsystem 714 and between the telemetry processor 710 and the memory subsystem 714. However, unlike the process illustrated in FIG. 26, the process illustrated in FIG. 27 presumes that the memory subsystem 714 can and does provide an indication of its write status and/or that either the device function processor 706 or the telemetry module 710 can and does determine the write status of the memory subsystem 714. The various steps of the sub-processes 900' and 902' are identical to those of the sub-processes 900 and 902 except that in the sub processes 900' and 902' the steps of the sub-processes 900 and 902 are somewhat rearranged. In any case, like numbers are used in the sub-processes 900' and 902' to identify like steps of the sub-processes 900 and 902.

The sub-process 900' for managing by the device function processor 706 of information exchange with the memory subsystem 714 begins at step 906 where the device function processor 706 checks the write status of the memory subsystem 714. If the write status checked at step 906 indicates that no new data has been written to the memory subsystem 714 since last executing step 906, the sub-process 900' advances to step 912. If and when the write status checked at step 906 indicates that new data has been written by the telemetry processor 710 to the memory subsystem 714, the sub-process 900' advances to step 904 where the device function processor 706 reads the data in the form of an information packet from the memory subsystem 714. Thereafter at step 908, the read data is processed by the device function processor 706 and any results, e.g., commands or data, generated by the processing of the new data and/or any changed data from step 908 are written by the device function processor 706 to the memory subsystem 714 at step 910. The device function processor 706 periodically executes the sub-process 900' independently of the timing of operation of the memory subsystem 714 and also independently of the timing of operation of the telemetry processor 710.

The sub-process 902' for managing by the telemetry processor 710 of information exchange with the device function processor 706 via the memory subsystem 714 begins at step 916 where the telemetry processor 710 checks if an information packet of a wirelessly received message from the electronic device 704 via the communication link 703 and extracted from the wireless communication protocol structure is to be exchanged with the device function processor. When and if information is to be exchanged, the process 902' advances to the step 918. Thereafter at step 918, the telemetry processor 710 writes the extracted information packet to the memory subsystem 714. Again, in carrying out steps 916 and 918, the telemetry processor 710 does not read, interpret or act upon any substantive data contained in the information packet, but rather only extracts the information packet from the communication protocol structure, e.g., unpacks it from the BlueTooth® communication protocol structure, and writes the packet to the memory subsystem 714.

At step 922, the telemetry processor 710 checks the write status of the memory subsystem 714. If the write status checked at step 922 indicates that no new data has been written to the memory subsystem 714 since last executing step 922, the sub-process 902' advance to step 926. If and when the write status checked at step 922 indicates that new data has been written by the device function processor 706 to the memory subsystem 714, the sub-process 902' advances to step 920 to read data in the form of an information packet from the memory subsystem 714. Thereafter at step 924, the telemetry processor 710 packs the information packet into the wireless communication protocol structure and wirelessly transmits the information packet to the electronic device 704. It will be understood that any references to the memory subsystem 714 in the description of the process of FIG. 27 may refer to the memory subsystem 714 generally and/or to any one or more of the memory subsystem embodiments 714'-714$^{vi}$ illustrated and described herein.

In one illustrative embodiment, the write status of the memory subsystem 714 may be generated by including a header in each information packet that is written to the memory subsystem 714 and by including in the header a write status flag, e.g., one or more bits of the header. At the writing of a new information packet into the memory subsystem 74, the write status flag or bit is set or reset by the one of the device function processor 706 or the telemetry processor 710 that writes the new information packet to the memory subsystem 714. To subsequently check if the information packet in the memory subsystem 714 is new, the processor 706 or 710 need only check the write flag or bit of the header of the information packet residing in the memory subsystem 714. When the processor 706 or 710 reads an information packet in the memory subsystem 714, the processor 706 or 710 changes the status of, e.g., resets or sets, the write flag or bit, to thereby mark the information packet as having been read.

In another illustrative embodiment, the write status of the memory subsystem 714 may be generated by deleting the information packet from the memory subsystem 714 after reading it. This may be accomplished by setting, resetting or changing the status of a delete flag or bit contained in the header of the information packet, or by setting all header bits and/or all data bits to a predefined code, e.g., all zeros, all ones, or the like.

In yet another illustrative embodiment, the write status of the memory subsystem 714 may be generated by storing a flag table at a specified location within the memory subsystem 714. When a new information packet is written to the memory subsystem 714 by either processor 706 or 710, that processor sets a new data flag in the flag table to new. After reading the information packet, the processor 706 or 710 then sets the new data flag to read. Thus to check if the memory subsystem 714 contains a new information packet, the processor 706 or 710 need look not at the packet but only at the flag table. The information packet is accessed only if the flag table indicates that the information packet is new. In embodiments of the memory subsystem 714 that include a memory processor, the flag table may be stored in the memory of the memory processor, an on-chip memory or an external memory, and in any case the flag table may be set and cleared by the memory processor.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

What is claimed is:

1. An electronic device for communicating wirelessly with another electronic device, the electronic device comprising:
   a first processor configured to control only wireless communications with the another device but not operations associated only with the electronic device,
   a second processor configured to control the operations associated only with the electronic device but not the wireless communications with the another device,
   a memory device connected between the first and second processors, the first and second processors each configured to exchange information with the memory device separately and independently of the exchange of information by the other of the first and second processors with the memory device,
   wherein the memory device comprises a third processor;
   a first power supply configured to produce a first supply voltage derived from the one or more batteries and provide the first supply voltage to the first second processor and to the memory unit,
   a second power supply configured to produce a second supply voltage derived from the one or more batteries and to provide the second supply voltage to the first processor,
   a test element receiving port configured to receive a test element,
   electronic circuitry configured to detect insertion of the test element into the test element receiving port and to produce a corresponding strip insert signal, a fourth processor configured to analyze a liquid sample provided on the test element to determine a concentration of an analyte in the liquid sample, the fourth processor configured to be responsive to the strip insert signal to provide a strip insertion message to the memory device, and wherein the memory device configured to be responsive to the strip insertion message to command orderly shutdown of the first processor and to then disable the second power supply such that the second power supply no longer produces the second supply voltage.

2. The electronic device of claim 1 further comprising a first one of a synchronous and an asynchronous interface electrically connected between the first processor and the memory device, and wherein the first processor is configured to send information wirelessly received from the another electronic device to the memory device via the first one of the synchronous and asynchronous interface, and to retrieve information to be communicated wirelessly to the another electronic device from the memory device via the first one of the synchronous and asynchronous interface.

3. The electronic device of claim 2 further comprising a second one of a synchronous and an asynchronous interface electrically connected between the second processor and the memory device and wherein the second processor is configured to retrieve from the memory device via the second one of the synchronous and asynchronous interface the information wirelessly received from the another electric device and sent to the memory device by the first processor, and to send to the memory device via the second one of the synchronous and asynchronous interface the information to be communicated wirelessly to the another electronic device by the first processor.

4. The electronic device of claim 3 wherein the memory device comprises an outbound buffer that is configured to store therein the information sent to the memory device by the second processor and that is to be communicated wirelessly to the another electronic device by the first processor, the outbound buffer being in data communication with the first and second ones of the synchronous and asynchronous interfaces.

5. The electronic device of claim 4 wherein the memory device comprises an inbound buffer that is configured to store therein the information wirelessly received from the another electric device and sent to the memory device by the first processor and that is to be retrieved from the memory device by the second processor, the inbound buffer being in data communication with the first and second ones of the synchronous and asynchronous interfaces.

6. The electronic device of claim 5 wherein the first processor is configured to incorporate the information retrieved from the outbound buffer into a wireless communications protocol structure, and to then wirelessly transmit the incorporated information to the another electronic device using the wireless communication protocol.

7. The electronic device of claim 6 wherein the wireless communication protocol is a radio frequency communication protocol.

8. The electronic device of claim 5 wherein the first processor is configured to wirelessly receive information incorporated into a wireless communication protocol structure from the another electronic device, to isolate the information from the wireless communication protocol structure and to then send the isolated information to the inbound buffer of the memory device.

9. The electronic device of claim 8 wherein the wireless communication protocol is a radio frequency communication protocol.

10. The electronic device of claim 5 wherein the second processor is configured to send the information to the memory device by requesting, asynchronously with respect to operation of the first processor, the state of the outbound buffer of the memory device and to send the information to the memory device only if the memory device indicates that the outbound buffer is not full, and to otherwise wait for a time period before again requesting, asynchronously with respect to operation of the first processor, the state of the outbound data buffer of the memory device.

11. The electronic device of claim 5 wherein the second processor is configured to retrieve from the memory device the information wirelessly received from the another electric device and sent to the memory device by the first processor by periodically, and asynchronously with respect to operation of the first processor, requesting the state of the inbound buffer of the memory device, the second processor configured to retrieve the information from the inbound buffer of the memory device only if the memory device indicates that the inbound buffer contains information, and to otherwise continue to periodically, and asynchronously with respect to operation of the second processor, request the state of the inbound data buffer.

12. The electronic device of claim 5 wherein the first one of the synchronous and asynchronous interface is an asynchronous interface that includes a clear to send (CTS) signal line, and wherein the first processor is configured to activate the CTS signal line whenever the first processor is requesting data and to otherwise deactivate the CTS signal line.

13. The electronic device of claim 12 wherein the first processor is configured to request the information to be communicated to the another electronic device from the memory device by periodically, and asynchronously with respect to operation of the second processor and operation of the memory device, activating the CTS signal line and retrieving the information to be wirelessly communicated to the another electronic device from the outbound buffer only if the outbound buffer contains data, and to otherwise continue to periodically, and asynchronously with respect to operation of the second processor and operation of the memory device, activate the CTS signal line.

14. The electronic device of claim 5 wherein the first one of the synchronous and asynchronous interface is an asynchronous interface that includes a ready to send (RTS) signal line, and wherein the memory device is configured to activate the RTS signal line whenever the inbound data buffer is not full and to otherwise deactivate the RTS signal line.

15. The electronic device of claim 13 wherein the first processor is configured to send the information wirelessly received from the another electronic device to the memory device by periodically, and asynchronously with respect to operation of the second processor and operation of the memory device, monitoring the RTS signal line and sending the information wirelessly received from the another electronic device to the inbound buffer of the memory device only if the RTS signal line is activated, and to otherwise continue to periodically, and asynchronously with respect to operation of the second processor and operation of the memory device, monitor the RTS signal line.

16. The electronic device of claim 1 further comprising an on/off switch, wherein the memory device is configured to be responsive to an on signal produced by the on/off switch to enable the second power supply to produce the second supply voltage, and to an off signal produced by the on/off switch to command orderly shutdown of the first processor and to then disable the second power supply such that the second power supply no longer produces the second supply voltage.

17. The electronic device of claim 1 wherein the fourth processor is configured to provide a test complete message to the memory device when the concentration of the analyte is determined by the fourth processor, and wherein the memory device is configured to be responsive to the test complete message to enable the second power supply such that the second power supply produces the second supply voltage.

18. The electronic device of claim 1 further comprising a plurality of user activated buttons or keys, wherein if the first power supply is producing the first supply voltage and the second power supply is producing the second supply voltage, the memory device is responsive to one of a simultaneous activation of predefined combination of two or more of the plurality of user activated buttons or keys, activation of a predefined sequence of two or more of the plurality of user activated buttons or keys and a dedicated one of the plurality of user activated buttons or keys to command orderly shutdown of the first processor and to then disable the second power supply such that the second power supply no longer produces the second supply voltage.

19. The electronic device of claim 1 further comprising a plurality of user activated buttons or keys, wherein if the first power supply is producing the first supply voltage and the second power supply is disabled so that it is not producing the second supply voltage, the memory device is responsive to simultaneous activation of a predefined combination of two or more of the plurality of user activated buttons or keys to enable the second supply voltage so that it produces the second supply voltage.

20. The electronic device of claim 1 further comprising an on/off switch, wherein the first power supply is enabled by an on signal produced by the on/off switch to produce the first supply voltage, and is disabled by an off signal produced by the on/off switch such that the first power supply does not produce the first supply voltage.

21. The electronic device of claim 20 further comprising a display unit,
wherein the second processor is configured, when the first power supply is enabled, to control the display unit to display an indication that a wireless connection between the electronic device and the another electronic device is not established.

22. The electronic device of claim 1 further comprising a voltage sense line electrically connected between the second power supply and the second processor, the voltage sense line carrying a sense voltage that is indicative of the supply voltage produced by the second power supply, wherein the second processor is configured to be responsive to the sense voltage to store, asynchronously with respect to operation of the first processor, an acknowledgement response command in the memory device when the sense voltage indicates that the second power supply has been enabled to produce the second supply voltage after having been disabled such that the second power supply did not produce the second supply voltage.

23. The electronic device of claim 22 wherein the first processor is configured to retrieve, asynchronously with respect to operation of the second processor, the acknowledgment response command from the memory device, and to wirelessly transmit the acknowledgement transmit command.

24. The electronic device of claim 23 wherein the first processor is configured, if the another electronic device wirelessly transmits an acknowledgement response in response to receipt of the acknowledgement response command and the transmitted acknowledgement response is received by the first processor, to isolate the acknowledgement response from a wireless communication protocol structure used by the another electronic device to wirelessly transmit the acknowledgment response, and to then store the acknowledgement response in the memory unit asynchronously with respect to operation of the memory unit and operation of the second processor.

25. The electronic device of claim 24 further comprising a display unit,
wherein the second processor is configured to, asynchronously with respect to operation of the first processor, retrieve the acknowledgement response from the memory unit and to then control the display unit to display an indication that a wireless connection exists between the electronic device and the another electronic device.

26. The electronic device of claim 25 wherein the second processor is configured to periodically store the acknowledgement response command in the memory device asynchronously with respect to operation of the first processor, to then periodically check the memory device, asynchronously with respect to operation of the first processor, and to continue to control the display unit to display the indication that the wireless connection exists between the electronic device and the another electronic device as long as the second processor retrieves the acknowledgement response from the memory unit within a predefined time period following storage of the acknowledgement response command in the memory device.

27. The electronic device of claim 26 wherein the second processor is configured to control the display unit to display the indication that the wireless connection does not exist between the electronic device and the another electronic device if second processor does not retrieves the acknowledgement response from the memory unit within the predefined time period following storage of the acknowledgement response command in the memory device.

28. The electronic device of claim 1 further comprising: a display unit, and a voltage sense line electrically connected between the second power supply and the second processor, the voltage sense line carrying a sense voltage that is indicative of the supply voltage produced by the second power supply, wherein the second processor is configured to be responsive to the sense voltage to control the display unit to display an indication that the second processor is producing the second supply voltage if the sense voltage indicates that the second processor is producing the second supply voltage.

29. The electronic device of claim 1 further comprising: a display unit, and a voltage sense line electrically connected between the second power supply and the second processor, the voltage sense line carrying a sense voltage that is indicative of the supply voltage produced by the second power supply, wherein the second processor is configured to be responsive to the sense voltage to control the display unit to display an indication that the second processor is not producing the second supply voltage if the sense voltage indicates that the second processor is not producing the second supply voltage.

30. The electronic device of claim 1 further comprising: an on/off switch, a display unit, a fourth processor configured to analyze a liquid sample provided on a test element to determine a concentration of an analyte in the liquid sample, the fourth processor configured to provide a test complete message to the second processor when the concentration of the analyte is determined by the fourth processor, wherein the second power supply is disabled such that it does not produce the second supply voltage when the fourth processor is determining the concentration of the analyte in the liquid sample, the second power supply configured to be responsive to an on signal produced by the on/off switch to become enabled and produce the second supply voltage, and wherein the second processor is configured to the responsive to the test complete message produced by the fourth processor to control the display unit to display a message that instructs the user to active the on/off switch to produce the on signal in order to communication wirelessly with the another electronic device.

31. The electronic device of claim 1 wherein the memory device comprises an outbound buffer that is configured to store therein information sent to the memory device by the second processor that is to be communicated wirelessly to the another electronic device by the first processor, the outbound buffer being in data communication with the first and second processors, and wherein the memory device is configured to monitor a status of the outbound buffer and to control operation of the second power supply based on the status of the outbound buffer.

32. The electronic device of claim 31 wherein the memory device comprises a timer circuit,
and wherein the memory device is configured to reset the timer circuit each time the second processor stores information in the outbound buffer of the memory device,
and wherein the memory device is configured to maintain the second power supply enabled such that the second power supply produces the second supply voltage as long as the memory device resets the timer circuit when a predefined time period elapses since last resetting the timer circuit.

33. The electronic device of claim 32 wherein the memory device is configured to disable the second power supply such that the second power supply does not produce the second supply voltage if the memory device does not reset the timer circuit before the predefined time period elapses since last resetting the timer circuit.

34. The electronic device of claim 33 wherein the memory device is configured to reset the timer circuit when second processor stores information in the outbound buffer of the memory device while the second power supply is disabled,
and wherein the memory device is configured to enable the second power supply such that the second power supply produces the second supply voltage when the timer circuit is reset while the second power supply is disabled.

35. The electronic device of claim 33 further comprising:
a test element receiving port configured to receive a test element,
electronic circuitry configured to detect insertion of the test element into the test element receiving port and to produce a corresponding strip insert signal,
a fourth processor configured to analyze a liquid sample provided on the test element to determine a concentration of an analyte in the liquid sample, the fourth processor configured to be responsive to the strip insert signal to provide a strip insertion message to the second processor,
wherein the second processor is configured to cease storing information in the outbound buffer of the memory device when the fourth processor produces the strip insert message so that the memory device does not reset the timer circuit before the predefined time period elapses since last resetting the timer circuit and the memory device then disables the second power supply such that the second power supply does not produce the second supply voltage.

36. The electronic device of claim 35 wherein the fourth processor is configured to provide a test complete message to the second processor when the concentration of the analyte is determined by the fourth processor,
and wherein the second processor is configured to resume storing information in the outbound buffer of the memory device when the fourth processor produces the test complete message so that the memory device resets the timer circuit and the memory device then enables the second power supply such that the second power supply produces the second supply voltage.

37. The electronic device of claim 33 further comprising:
a test element receiving port configured to receive a test element,
a fourth processor configured to analyze a liquid sample provided on the test element to determine a concentration of an analyte in the liquid sample, the fourth processor configured to be responsive to a request to disable the second power supply to provide a corresponding message to the second processor,
wherein the second processor is configured to cease storing information in the outbound buffer of the memory device when the fourth processor produces the corresponding message so that the memory device does not reset the timer circuit before the predefined time period elapses since last resetting the timer circuit and the memory device then disables the second power supply such that the second power supply does not produce the second supply voltage.

38. The electronic device of claim 1 wherein the second power supply is always enabled such that the second power supply always produces the second supply voltage, and wherein the first processor is configured to be responsive to a number of different events to transition into, and out of, a number of different low power states.

39. The electronic device of claim 38 wherein the first processor further comprises a timer circuit,
and wherein the first processor is configured to remain in a fully powered awake state as long as a first predefined time period does not elapse since last resetting the timer circuit.

40. The electronic device of claim 39 wherein the memory device comprises an outbound buffer that is configured to store therein information sent to the memory device by the second processor that is to be communicated wirelessly to the another electronic device by the first processor, the outbound buffer being in data communication with the first and second processors,
wherein the first processor is configured to periodically check a status of the outbound buffer and to reset the timer circuit only if the outbound buffer contains information to be wirelessly communicated to the another electronic device,
and wherein the first processor is configured to transition to a first low power state if the first predefined time period elapses since last resetting the timer circuit, the first processor consuming less electrical power in the first low power state than when in the fully powered awake state.

41. The electronic device of claim 40 wherein the first processor is configured to transition to a second low power state, in which the first processor consumes less electrical power than when in the first low power state, if a second predefined time period elapses since last resetting the timer circuit, the second predefined time period being greater than the first predefined time period.

42. The electronic device of claim 40 wherein the first processor is configured to transition to successively lower power states, in which the first processor consumes successively less power than in the previous low power state, as the time period that elapses since resetting the timer circuit successively increases beyond the first predefined time period.

43. The electronic device of claim 42 wherein the first processor is configured in a lowest power state only to periodically wake up to check the status of the outbound buffer of the memory device, and to wake up to the fully powered awake state if the outbound buffer of the memory device has information stored therein, the first processor otherwise configured to transition back to the lowest power state.

44. The electronic device of claim 38 further comprising an on/off switch,
wherein the first processor is configured to transition from any of the number of different low power states to a fully powered awake state when the on/off switch is switched to an on position.

45. The electronic device of claim 44 wherein the first processor is configured to transition from the fully powered awake state and any of the number of different low power states to a lowest power sleep state when the on/off switch is switched to an off position.

46. The electronic device of claim 44 wherein the memory device has a sleep state and an awake state,
and wherein the memory device is configured to transition from the sleep state of the memory device to the awake state of the memory device when the on/off switch is switched to the on position.

47. The electronic device of claim 43 further comprising:
a test element receiving port configured to receive a test element,
electronic circuitry configured to detect insertion of the test element into the test element receiving port and to produce a corresponding strip insert signal,
a fourth processor configured to analyze a liquid sample provided on the test element to determine a concentration of an analyte in the liquid sample, the fourth processor configured to be responsive to the strip insert signal to provide a corresponding strip insert message to the second processor,
wherein the second processor is configured to cease storing information in the outbound buffer of the memory device when the fourth processor produces the strip insert message so that the first processor then successively transitions to lower power states as successively longer time periods elapse since last resetting the timer circuit.

48. The electronic device of claim 47 wherein the fourth processor is configured to provide a test complete message when the fourth processor has determined the concentration of an analyte in the liquid sample,
and wherein the second processor is configured to resume storing information in the outbound buffer of the memory device when the fourth processor produces the test complete message so that the first processor then transitions to the fully powered awake state to service the information stored in the outbound buffer of the memory device.

49. The electronic device of claim 38 further comprising a plurality of user activated buttons or keys,
wherein the first processor is configured to transition from any of the number of different low power states to a fully powered awake state upon detection of one of a simultaneous activation of a predefined combination of two or more of the plurality of user activated buttons or keys, activation of a predefined sequence of two or more of the plurality of user activated buttons or keys and a dedicated one of the plurality of user activated buttons or keys.

50. The electronic device of claim 38 further comprising a plurality of user activated buttons or keys,
wherein the first processor is configured to transition from the fully powered awake state and any of the number of different low power states to an un-powered off state upon detection of one of a simultaneous activation of a predefined combination of two or more of the plurality of user activated buttons or keys, activation of a predefined sequence of two or more of the plurality of user activated buttons or keys and a dedicated one of the plurality of user activated buttons or keys.

51. The electronic device of claim 1 further comprising a clock circuit having a programming input that is electrically connected to the second processor and an output that is electrically connected to the memory device, wherein the clock circuit is programmable via the second processor with at least one automatic on time or reminder, and the clock circuit is configured to produce a trigger signal upon occurrence of the at least one automatic on time or reminder, and wherein the memory device is responsive to the trigger signal, when the second power supply is disabled, to enable the second power supply such that the second power supply produces the second supply voltage.

52. The electronic device of claim 1 further comprising: a test element receiving port configured to receive a test element, a fourth processor that is electrically connected to the second processor and that is configured to analyze a liquid sample provided on the test element to determine a concentration of an analyte in the liquid sample, the fourth processor configured to provide a value of the concentration of the analyte in the liquid sample to the second processor, and an electronic switch configured to produce a first signal upon detection of insertion of the test element into the test element receiving port and to produce a second signal upon detection of removal of the test element from the test element receiving port, the electronic switch having an output that is electrically connected to the fourth processor and to the memory device such that the first and second signals produced by the switch are provided to the fourth processor and to the memory device, wherein the memory device configured to be responsive to the first signal produced by the electronic switch to command orderly shutdown of the first processor and to then disable the second power supply such that the second power supply does not produce the second supply voltage.

53. The electronic device of claim 52 wherein the memory device is configured to be responsive to the second signal produced by the electronic switch, if the second power supply is disabled, to enable the second power supply such that the second power supply produces the second supply voltage.

54. The electronic device of claim 1 further comprising: a test element receiving port configured to receive a test element, and a switch configured to produce a first signal upon detection of insertion of the test element into the test element receiving port and to produce a second signal upon detection of removal of the test element from the test element receiving port, the switch having an output that is electrically connected only to the memory device such that the first and second signals produced by the switch are provided to the memory device, wherein the memory device configured to be responsive to the first signal produced by the switch to command orderly shutdown of the first processor and to then disable the second power supply such that the second power supply does not produce the second supply voltage.

55. The electronic device of claim 53 wherein the memory device is configured to be responsive to the second signal produced by the switch, if the second power supply is disabled, to enable the second power supply such that the second power supply produces the second supply voltage.

56. The electronic device of claim 1 further comprising a current sensing circuit having at least one input that is electrically connected to the first power supply and an output that is electrically connected to the second power supply, the current sensing circuit configured to produce a control signal having a first state and a second state based on a magnitude of a supply current produced by the first power supply, wherein the first state of the control signal produced by the current sensing circuit disables the second power supply such that the second power supply does not produce the second supply voltage and the second state of the control signal produced by the current sensing circuit enables the second power supply such that the second power supply produces the second supply voltage.

57. The electronic device of claim 56 wherein the current sensing circuit is configured to produce the second state of the control signal when the second processor is fully activated for operation such that the magnitude of the supply current produced by the first power supply is greater than when the second processor is not fully activated for operation.

58. The electronic device of claim 57 wherein the second processor includes a timer circuit that the second processor resets periodically when the second processor is actively operating,
and wherein the second processor is configured to transition to a low power sleep state if the second processor is inactive for a predefined time period following a last reset of the timer circuit,
and wherein the current sensing circuit is configured to produce the first state of the control signal when the second processor transitions to the low power sleep state such that the magnitude of the supply current produced by the first power supply is greater than when the second processor is actively operating.

59. The electronic device of claim 56 further comprising:
a test element receiving port configured to receive a test element,
electronic circuitry, and
a fourth processor electrically connected to the electronic circuitry and to the second processor,
wherein the first power supply provides the first supply voltage to the electronic circuitry and to the fourth processor,
and wherein the electronic circuitry and the fourth processor are each normally in a low power sleep state such that the magnitude of the supply current produced by the first power supply is less than when the electronic circuitry and the fourth processor are both actively operating,
and wherein the current sensing circuit normally produces the second state of the control signal, such that the second power supply is normally enabled and producing the second supply voltage, when the electronic circuitry and the fourth processor are each in the low power sleep states.

60. The electronic device of claim 59 wherein the electronic circuitry is configured to be responsive to insertion of the test element into the test element receiving port to transition from the low power sleep state thereof to an actively operating state and produce a corresponding strip insert signal,
and wherein the fourth processor is configured to be responsive to the strip insert signal to transition from the low power operating state thereof to an actively operating state and analyze a liquid sample provided on the test element to determine a concentration of an analyte in the liquid sample,
and wherein the magnitude of the supply current produced by the first power supply when the electronic circuitry and the fourth processor are both actively operating is greater than when the electronic circuitry and the fourth processor are in their low power sleep states,
and wherein the current sensing circuit is configured to transition the control signal from the first state thereof to the second state thereof when the electronic circuitry and the fourth processor each transition from the low power sleep state to the actively operating state.

61. The electronic device of claim 60 wherein the electronic circuitry and the fourth processor are each configured to transition from the actively operating state to the low power sleep state after the fourth processor determines the concentration of the analyte in the liquid sample,
and wherein the current sensing circuit is configured to transition the control signal from the second state thereof to the first state thereof when the electronic circuitry and the fourth processor each transition from the actively operating state to the low power sleep state after the fourth processor determines the concentration of the analyte in the liquid sample.

62. The electronic device of claim 59 wherein the electronic circuitry comprises a timer circuit that is programmed with at least one automatic on time or reminder, and the clock circuit is configured to produce a trigger signal upon occurrence of the at least one automatic on time or reminder, and the electronic circuitry is configured to be responsive to the trigger signal to transition from the low power operating state thereof to an actively operating state and to pass the trigger signal to the fourth processor,
and wherein the fourth processor is configured to be responsive to the trigger signal to transition from the low power operating state thereof to an actively operating state and to pass the trigger signal to the second processor,
and wherein the magnitude of the supply current produced by the first power supply when the electronic circuitry and the fourth processor are both actively operating is greater than when the electronic circuitry and the fourth processor are in their low power sleep states,
and wherein the current sensing circuit is configured to transition the control signal from the first state thereof to the second state thereof when the electronic circuitry and the fourth processor each transition from the low power sleep state to the actively operating state.

63. The electronic device of claim 1 further comprising a current sensing circuit having at least one input that is electrically connected to the first power supply and an output that is electrically connected to the memory device, the current sensing circuit configured to produce a control signal having a first state and a second state based on a magnitude of a supply current produced by the first power supply, wherein the memory device is responsive to the first state of the control signal produced by the current sensing circuit to disable the second power supply such that the second power supply does not produce the second supply voltage, and to the second state of the control signal produced by the current sensing circuit to enable the second power supply such that the second power supply produces the second supply voltage.

64. The electronic device of claim 63 wherein the current sensing circuit is configured to produce the second state of the control signal when the second processor is fully activated for operation such that the magnitude of the supply current produced by the first power supply is greater than when the second processor is not fully activated for operation.

65. The electronic device of claim 64 wherein the second processor includes a timer circuit that the second processor resets periodically when the second processor is actively operating,
and wherein the second processor is configured to transition to a low power sleep state if the second processor is inactive for a predefined time period following a last reset of the timer circuit,
and wherein the current sensing circuit is configured to produce the first state of the control signal when the second processor transitions to the low power sleep state such that the magnitude of the supply current produced by the first power supply is greater than when the second processor is actively operating.

66. The electronic device of claim 63 further comprising:
a test element receiving port configured to receive a test element,
electronic circuitry, and
a fourth processor electrically connected to the electronic circuitry and to the second processor,
wherein the first power supply provides the first supply voltage to the electronic circuitry and to the fourth processor,
and wherein the electronic circuitry and the fourth processor are each normally in a low power sleep state such that the magnitude of the supply current produced by the first power supply is less than when the electronic circuitry and the fourth processor are both actively operating,
and wherein the current sensing circuit normally produces the second state of the control signal, such that the second power supply is normally enabled and producing the second supply voltage, when the electronic circuitry and the fourth processor are each in the low power sleep states.

67. The electronic device of claim 66 wherein the electronic circuitry is configured to be responsive to insertion of the test element into the test element receiving port to transition from the low power sleep state thereof to an actively operating state and produce a corresponding strip insert signal,
and wherein the fourth processor is configured to be responsive to the strip insert signal to transition from the low power operating state thereof to an actively operating state and analyze a liquid sample provided on the test element to determine a concentration of an analyte in the liquid sample,
and wherein the magnitude of the supply current produced by the first power supply when the electronic circuitry and the fourth processor are both actively operating is greater than when the electronic circuitry and the fourth processor are in their low power sleep states,
and wherein the current sensing circuit is configured to transition the control signal from the first state thereof to the second state thereof when the electronic circuitry and the fourth processor each transition from the low power sleep state to the actively operating state.

68. The electronic device of claim 67 wherein the electronic circuitry and the fourth processor are each configured to transition from the actively operating state to the low power sleep state after the fourth processor determines the concentration of the analyte in the liquid sample,
and wherein the current sensing circuit is configured to transition the control signal from the second state thereof to the first state thereof when the electronic circuitry and the fourth processor each transition from the actively operating state to the low power sleep state after the fourth processor determines the concentration of the analyte in the liquid sample.

69. The electronic device of claim 66 wherein the electronic circuitry comprises a timer circuit that is programmed with at least one automatic on time or reminder, and the clock circuit is configured to produce a trigger signal upon occurrence of the at least one automatic on time or reminder, and the electronic circuitry is configured to be responsive to the trigger signal to transition from the low power operating state thereof to an actively operating state and to pass the trigger signal to the fourth processor,
and wherein the fourth processor is configured to be responsive to the trigger signal to transition from the low power operating state thereof to an actively operating state and to pass the trigger signal to the second processor,
and wherein the magnitude of the supply current produced by the first power supply when the electronic circuitry and the fourth processor are both actively operating is greater than when the electronic circuitry and the fourth processor are in their low power sleep states,
and wherein the current sensing circuit is configured to transition the control signal from the first state thereof to the second state thereof when the electronic circuitry and the fourth processor each transition from the low power sleep state to the actively operating state.

70. The electronic device of claim 40 wherein, if a wireless connection between the electronic device and the another electronic device is terminated or lost and the second processor sends information to the outbound buffer, one of the first processor and the second processor is configured to clear the outbound buffer after a predefined number of failed attempts by the first processor to reestablish a wireless connection between the electronic device and the another electronic device.

71. The electronic device of claim 70 wherein the first processor is configured to transition to successively lower power states, in which the first processor consumes successively less power than in the previous low power state, as the time period that elapses since resetting the timer circuit successively increases beyond the first predefined time period following the predefined number of failed attempts by the first processor to reestablish a wireless connection between the electronic device and the another electronic device.

72. The electronic device of claim 71 wherein the first processor is configured in a lowest power state only to periodically wake up to check the status of the outbound buffer of the memory device, and to wake up to the fully powered awake state if the outbound buffer of the memory device has information stored therein, the first processor otherwise configured to transition back to the lowest power state.

73. The electronic device of claim 72 wherein the first processor is configured in the lowest power state to produce a power supply control signal if the time period that elapses since resetting the timer circuit reaches a predefined time out value that is greater than the time period for which the first processor enters the lowest power sleep state,
and wherein the second power supply is configured to become disabled such that the second power supply does not produce the second supply voltage when the first processor produces the power supply control signal.

74. The electronic device of claim 73 further comprising a plurality of user activated buttons or keys,
   wherein the second power supply is configured to be responsive to one of a simultaneous activation of a predefined combination of two or more of the plurality of user activated buttons or keys, activation of a predefined sequence of two or more of the plurality of user activated buttons or keys and a dedicated one of the plurality of user activated buttons or keys to become enabled such that the second power supply produces the second supply voltage,
   and wherein the first processor is configured to enter the lowest power sleep state when the second power supply is via the one of the predefined combination of two or more of the plurality of user activated buttons or keys, activation of a predefined sequence of two or more of the plurality of user activated buttons or keys and a dedicated one of the plurality of user activated buttons or keys.

75. The electronic device of claim 42 wherein the first processor is configured in the lowest power state to produce a power supply control signal if the time period that elapses since resetting the timer circuit reaches a predefined time out value that is greater than the time period for which the first processor enters the lowest power sleep state,
   and wherein the second power supply is configured to become disabled such that the second power supply does not produce the second supply voltage when the first processor produces the power supply control signal.

76. The electronic device of claim 75 further comprising a plurality of user activated buttons or keys,
   wherein the second power supply is configured to be responsive to one of a simultaneous activation of a predefined combination of two or more of the plurality of user activated buttons or keys, activation of a predefined sequence of two or more of the plurality of user activated buttons or keys and a dedicated one of the plurality of user activated buttons or keys to become enabled such that the second power supply produces the second supply voltage,
   and wherein the first processor is configured to enter the lowest power sleep state when the second power supply is via the one of the predefined combination of two or more of the plurality of user activated buttons or keys, activation of a predefined sequence of two or more of the plurality of user activated buttons or keys and a dedicated one of the plurality of user activated buttons or keys.

77. An electronic device for communicating wirelessly with another electronic device, the electronic device comprising:
   a first processor that controls only wireless communications with the another device and excluding operations associated only with the electronic device,
   a second processor that controls the operations associated only with the electronic device and excluding the wireless communications with the another device,
   a memory device connected between the first and second processors, the first and second processors each operate autonomously with respect to each other and each exchange information with the memory device independently of each other,
   wherein the memory device comprises a third processor;
   a first power supply configured to produce a first supply voltage derived from the one or more batteries and provide the first supply voltage to the first second processor and to the memory unit,
   a second power supply configured to produce a second supply voltage derived from the one or more batteries and to provide the second supply voltage to the first processor,
   a test element receiving port configured to receive a test element,
   electronic circuitry configured to detect insertion of the test element into the test element receiving port and to produce a corresponding strip insert signal,
   a fourth processor configured to analyze a liquid sample provided on the test element to determine a concentration of an analyte in the liquid sample, the fourth processor configured to be responsive to the strip insert signal to provide a strip insertion message to the memory device, and
   wherein the memory device configured to be responsive to the strip insertion message to command orderly shutdown of the first processor and to then disable the second power supply such that the second power supply no longer produces the second supply voltage.

78. An electronic device for communicating wirelessly with another electronic device, the electronic device comprising:
   a first processor that controls only wireless communications with the another device and excluding operations associated only with the electronic device,
   a second processor that controls the operations associated only with the electronic device and excluding the wireless communications with the another device,
   a memory device connected between the first and second processors, the first and second processors each operate independently of each other and each operate asynchronously with respect to each other when exchanging information with the memory device,
   wherein the memory device comprises a third processor;
   a first power supply configured to produce a first supply voltage derived from the one or more batteries and provide the first supply voltage to the first second processor and to the memory unit,
   a second power supply configured to produce a second supply voltage derived from the one or more batteries and to provide the second supply voltage to the first processor,
   a test element receiving port configured to receive a test element,
   electronic circuitry configured to detect insertion of the test element into the test element receiving port and to produce a corresponding strip insert signal,
   a fourth processor configured to analyze a liquid sample provided on the test element to determine a concentration of an analyte in the liquid sample, the fourth processor configured to be responsive to the strip insert signal to provide a strip insertion message to the memory device, and
   wherein the memory device configured to be responsive to the strip insertion message to command orderly shutdown of the first processor and to then disable the second power supply such that the second power supply no longer produces the second supply voltage.

\* \* \* \* \*